US009651563B2

(12) United States Patent
Jacobs et al.

(10) Patent No.: US 9,651,563 B2
(45) Date of Patent: *May 16, 2017

(54) BIOMARKERS FOR LIVER FIBROSIS

(71) Applicant: Battelle Memorial Institute, Richland, WA (US)

(72) Inventors: Jon M. Jacobs, Pasco, WA (US); Kristin E. Burnum-Johnson, Richland, WA (US); Erin M. Baker, West Richland, WA (US); Richard D. Smith, Richland, WA (US); Marina A. Gritsenko, Richland, WA (US); Daniel Orton, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 23 days.

This patent is subject to a terminal disclaimer.

(21) Appl. No.: 14/799,405

(22) Filed: Jul. 14, 2015

(65) Prior Publication Data
US 2015/0323551 A1 Nov. 12, 2015

Related U.S. Application Data

(62) Division of application No. 14/209,860, filed on Mar. 13, 2014, now Pat. No. 9,134,326.

(60) Provisional application No. 61/785,225, filed on Mar. 14, 2013.

(51) Int. Cl.
*G01N 31/00* (2006.01)
*G01N 33/53* (2006.01)
*G01N 33/68* (2006.01)

(52) U.S. Cl.
CPC ... *G01N 33/6893* (2013.01); *G01N 2800/085* (2013.01)

(58) Field of Classification Search
None
See application file for complete search history.

(56) References Cited

U.S. PATENT DOCUMENTS 4,444,879 A * 4/1984 Foster ............... G01N 33/545 422/400
9,134,326 B2 * 9/2015 Jacobs ............... G01N 33/6893

FOREIGN PATENT DOCUMENTS

WO WO 2007/130636 A2 11/2007

OTHER PUBLICATIONS

Lewis et al. Freseniu J. Anal. Chem. Mar.-Apr. 2000; 36 (6-7) pp. 760-768.*
Chokkathukalam et al. (Bioanalysis, Feb. 2014, 6(4), pp. 511-524).*
Baker et al., "Utilizing High Throughput LC-IMS-QTOF MS Separations to Increase Proteome Coverage for Complex Biological and Environmental Samples," ASMS, Abstract, May 2012.
Baker et al., "Advancing the High Throughput Identification of Liver Fibrosis Protein Signatures Using Multiplexed Ion Mobility Spectrometry," *Mol Cell Proteomics* 13:1119-1127, 2014.
Bell et al., "Serum Proteomics and Biomarker Discovery Across the Spectrum of Nonalcoholic Fatty Liver Disease," *Hepatology* 51:111-120, 2010.
Cheung et al., "Usefulness of a Novel Serum Proteome-Derived Index FI-PRO (Fibrosis-Protein) in the Prediction of Fibrosis in Chronic Hepatitis C.," *Eur J Gastroenterol Hepatol.* 23:701-710, 2011.
Christensen et al., "Diagnostic Accuracy of Fibrosis Serum Panel (FIBROSpect II) Compared with Knodell and Ishak Liver Biopsy Scores in Chronic Hepatitis C Patients," *J. Viral Hepatitis* 13:652-658, 2006.
Diamond et al., "HepatoProteomics: Applying Proteomic Technologies to the Study of Liver Function and Disease," *Hepatology* 44:299-308, 2006.
Mukherjee and Sorrell, "Noninvasive Tests for Liver Fibrosis," *Semin Liver Dis.* 26:337-347, 2006.
Plebani and Basso, "Non-Invasive Assessment of Chronic Liver and Gastric Diseases," *Clin Chim. Acta* 381:39-49, 2007.
Rockey and Bissell, "Noninvasive Measures of Liver Fibrosis," *Hepatology* 43:S113-S120, 2006.
Shaheen et al., "Fibrotest and FibroScan for the Prediction of Hepatitis C-Related Fibrogenesis: A Systematic Review of Diagnostic Test Accuracy," *Am J Gasteroenterol.* 102:2589-2600, 2007.

* cited by examiner

*Primary Examiner* — Lisa Cook
(74) *Attorney, Agent, or Firm* — Klarquist Sparkman, LLP

(57) ABSTRACT

Methods and systems for diagnosing or prognosing liver fibrosis in a subject are provided. In some examples, such methods and systems can include detecting liver fibrosis-related molecules in a sample obtained from the subject, comparing expression of the molecules in the sample to controls representing expression values expected in a subject who does not have liver fibrosis or who has non-progressing fibrosis, and diagnosing or prognosing liver fibrosis in the subject when differential expression of the molecules between the sample and the controls is detected. Kits for the diagnosis or prognosis of liver fibrosis in a subject are also provided which include reagents for detecting liver fibrosis related molecules.

20 Claims, 9 Drawing Sheets
(8 of 9 Drawing Sheet(s) Filed in Color)

FIG. 1A
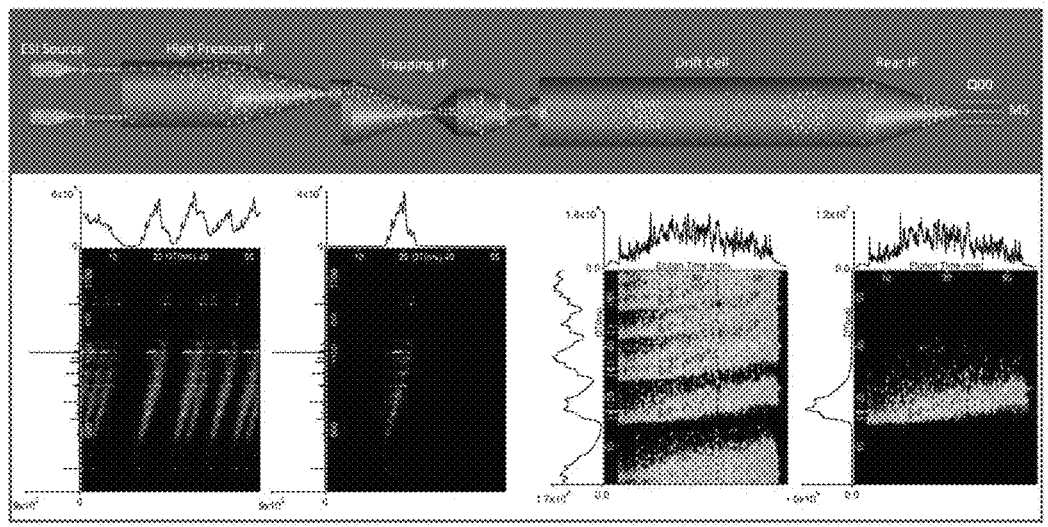
FIG. 1B          FIG. 1C
FIG. 2A          FIG. 2B
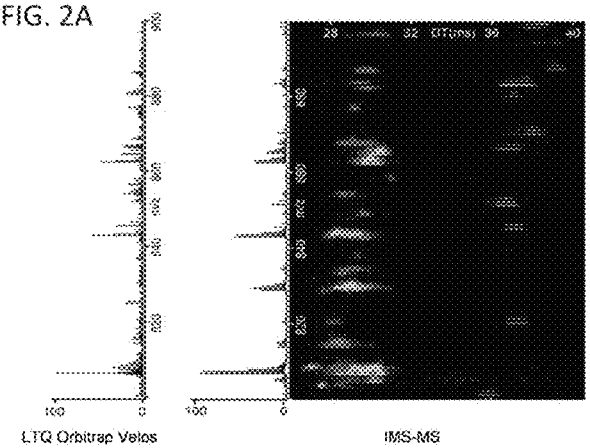    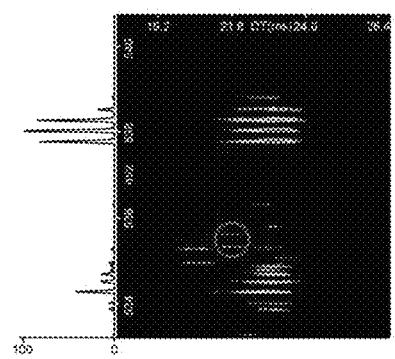

HCV Infected Liver Non-transplant Patients 45 patients  15 patients

SUBSET 1 (Cluster 2)

SUBSET 2 (Cluster 4)

BIOMARKERS FOR LIVER FIBROSIS

CROSS-REFERENCE TO RELATED APPLICATION

This application is a divisional of U.S. application Ser. No. 14/209,860 filed Mar. 13, 2014, now U.S. Pat. No. 9,134,326, which claims priority to U.S. Provisional Application No. 61/785,225 filed Mar. 14, 2013, both applications are herein incorporated by reference in their entirety.

ACKNOWLEDGMENT OF GOVERNMENT SUPPORT

This invention was made with government support under 5P41RR018522-10 awarded by the National Institutes of Health's National Center for Research Resources, under 8 P41 GM103493-10 awarded by the National Institute of General Medical Sciences, under R21-CA12619-01 and U24-CA-160019-01 awarded by the National Cancer Institute, and DE-AC05-76RL01830 awarded by the Department of Energy. The Government has certain rights in the invention.

FIELD

The present disclosure generally relates to methods and systems for the screening and detection of persons having or at risk for liver fibrosis, as well as kits that can be used with such methods and systems.

BACKGROUND

To date pre-clinical and clinical applications of mass spectrometry (MS)-based proteomic techniques analyzing complex biofluids have fallen short of expectations, largely due to deficiencies in both analytical sensitivity and throughput. These deficiencies result in measurements typically failing to confidently detect and quantify proteins at moderate to low concentrations, or not providing sufficient sample analysis throughput for statistical relevance. Higher sensitivity targeted MS analyses are currently utilized to address these shortcomings [1, 2]; however, these often only analyze a small list of proteins identified as biologically significant. While targeted MS measurements are increasingly common in clinical applications [3, 4], the limited number of proteins they examine does not necessarily reflect the biodiversity across a population, making broad untargeted measurements useful in developing individual disease metrics for diagnosis [5]. As the future of medicine proceeds toward a personal profiling approach [6, 7], the potential for robust high throughput clinical measurements based upon MS is highly attractive if its deficiencies can be addressed.

An initial step in attaining broad untargeted measurements that increasingly retain the benefits of targeted analyses exploits technological advances such as faster separations, more effective ion sources, detectors with greater dynamic range, and MS measurements with both higher resolution and accuracy. Advanced liquid-phase separations have already been employed to provide a significant sensitivity increase as illustrated by the higher number of proteins detected in liquid chromatography (LC)-MS-based studies [8]; however, the long LC separations most compatible with blood samples are extremely time-consuming. Fast gas-phase ion mobility spectrometry (IMS) separations that take place on the time scale of tens of milliseconds offer an additional separation stage and a way of reducing the need for extended LC separation times. In an IMS separation, ions subject to an electric field while traveling through a buffer gas separate quickly based on ion shape, e.g. compact species drift faster than those with extended structures [9, 10]. IMS can be coupled between LC and orthogonal acceleration time-of-flight (TOF) MS stages, and by combining the three orthogonal separations into a single LC-IMS-MS instrumentation platform, multidimensional high-resolution nested spectra are produced containing elution times, mass-to-charge ratios (m/z) and IMS drift times for all detectable ions in a sample [11, 12]

Liver fibrosis may result from a wide variety of conditions including chronic alcohol exposure, hepatitis B virus (HBV) infection, non-alcoholic fatty liver disease (NAFLD), hepatitis C virus (HCV) infection, Wilson's disease, alpha-1-antitrypsin deficiency, hemochromatosis, primary biliary cirrhosis, primary sclerosing cholangitis, and autoimmune hepatitis. Chronic HCV is the leading contributor to chronic liver disease and represents a worldwide public health concern affecting an estimated 130-170 million people [16]. The liver damage ensuing from HCV infection is also the leading cause of liver transplants in the United States and Europe and a major burden on healthcare services [17, 18]. In this disease, the liver elicits a persistent inflammatory and repair response known as fibrosis, which is characterized by the formation of fibrous tissue and scarring on the liver. Because the prognosis of HCV patients is related to the development of fibrosis and the risk of cirrhosis and hepatocellular carcinoma, an accurate evaluation of fibrogenic progression is important for patient care.

Currently, liver biopsies are the primary technique for generating information on the degree of fibrosis; however, they have multiple disadvantages, including risk of complications (e.g., major bleeding or inadvertent puncture of the lung, kidney, or colon), cost and occasionally inaccurate findings due to small specimen size and variability in histology evaluation. These disadvantages have spurred the development of noninvasive methods that can reliably predict, diagnose and assess the degree of fibrosis [19, 20].

SUMMARY

The present disclosure provides methods of diagnosing or prognosing liver fibrosis in a subject. Such methods can include detecting or measuring expression of at least two (e.g., at least 3, at least 4, at least 5 or at least 10) liver fibrosis-related molecules (such as proteins or nucleic acids) in a sample obtained from the subject, comparing the detected expression in the sample to controls representing expression of the at least two (e.g., at least 3, at least 4, at least 5 or at least 10) liver fibrosis-related molecules expected in a subject who does not have liver fibrosis or who has non-progressing liver fibrosis, and diagnosing or prognosing liver fibrosis in the subject when there is differential expression of the at least two (e.g., at least 3, at least 4, at least 5 or at least 10) liver fibrosis-related molecules between the sample and the controls, such as an increase or decrease in expression of at least 10% or at least 1.1 fold.

Also provided are one or more non-transitory computer-readable media that include computer-executable instructions causing a computing system to perform the methods provided herein.

Systems for analyzing a sample (such as a sample obtained from a subject suspected of having liver fibrosis) obtained from a subject are also provided. Such systems can include a means for measuring a level of at least two (e.g., at least 3, at least 4, at least 5 or at least 10) liver fibrosis-related molecules the sample (such as an antibody, probe, or primer) and means for diagnosing or prognosing liver fibrosis in the subject based on the level of the at least two liver fibrosis-related molecules. In some examples, the system includes implemented rules for determining diagnosing or prognosing liver fibrosis (e.g., positive or negative) based on the measured level of the at least two liver fibrosis-related molecules. In some examples, the system includes implemented rules for comparing the measured level of the at least two liver fibrosis-related molecules to a reference value, such as the level of the at least two liver fibrosis-related molecules positive or negative control (such as values expected in a subject who does not have liver fibrosis or who has non-progressing liver fibrosis). In some examples, the reference values are stored values. In some examples, the reference values are a level of the at least two liver fibrosis-related molecules measured from a control sample by said means for measuring. The system can also include one or more means for implementing the rules, whereby an indication of diagnosing or prognosing liver fibrosis (e.g., positive or negative) is provided based on the differential expression determined for the at least two liver fibrosis-related molecules measured in the patient sample and the control (e.g., reference value). Kits are also provided for the diagnosis or prognosis of liver fibrosis in a subject. Such kits can include reagents for detecting at least two (e.g., at least 3, at least 4, at least 5 or at least 10) liver fibrosis-related molecules (such as proteins or nucleic acids). In some embodiments, the kit has antibodies specific for at least two (e.g., at least 3, at least 4, at least 5 or at least 10) different liver fibrosis-related proteins. In some embodiments, the kit further includes labeled secondary antibodies which can bind to the antibodies specific for the proteins liver fibrosis-related proteins. In some embodiments, the kit has oligonucleotide probes or primers specific for at least two (e.g., at least 3, at least 4, at least 5 or at least 10) different liver fibrosis-related nucleic acid molecules.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a schematic representation of the ESI-IMS-MS regions of the overall platform. The smaller conformational ions (green circles) and larger conformational ions (red circles) illustrate the size separation in the IMS drift cell.

FIG. 1B provides a multiplexed nested IMS spectrum on the left shows both IMS drift time (x-axis) and m/z (y-axis) for a 9 peptide mixture. In this spectrum, 8 ion packets were released into the drift cell simultaneously. The corresponding de-multiplexed spectrum with all ions deconvoluted to their correct drift times is shown on the right. The intensity in the nested spectra is represented by color, with red being the most intense and blue being the least.

FIG. 1C shows the results of adding LC to LC-IMS-MS analyses. The plots illustrate the LC dimension total ion chromatogram (x-axis) and IMS drift time (y-axis) for a human serum dataset before (left) and after (right) de-multiplexing. The intensity in the nested spectra is represented by color, with red being the most intense and blue being the least.

FIG. 2A shows MS spectra for the LTQ Orbitrap Velos (left) and IMS-MS (right). The plots illustrate the reduction in noise in the IMS-MS spectrum and demonstrate how additional drift time information greatly simplifies peak detection, ultimately leading to more identifications.

FIG. 2B shows an LC-IMS-MS spectra with (Dynorphin A porcine)$^{3+}$ (circled) spiked at 100 pg/mL into human serum. The IMS-MS spectra are displayed as two-dimensional nested plots for IMS drift time (x-axis) and m/z (y-axis). The intensity in the nested spectra is represented by color, with red being the most intense and blue being the least.

SEQUENCE LISTING

Figure 3:
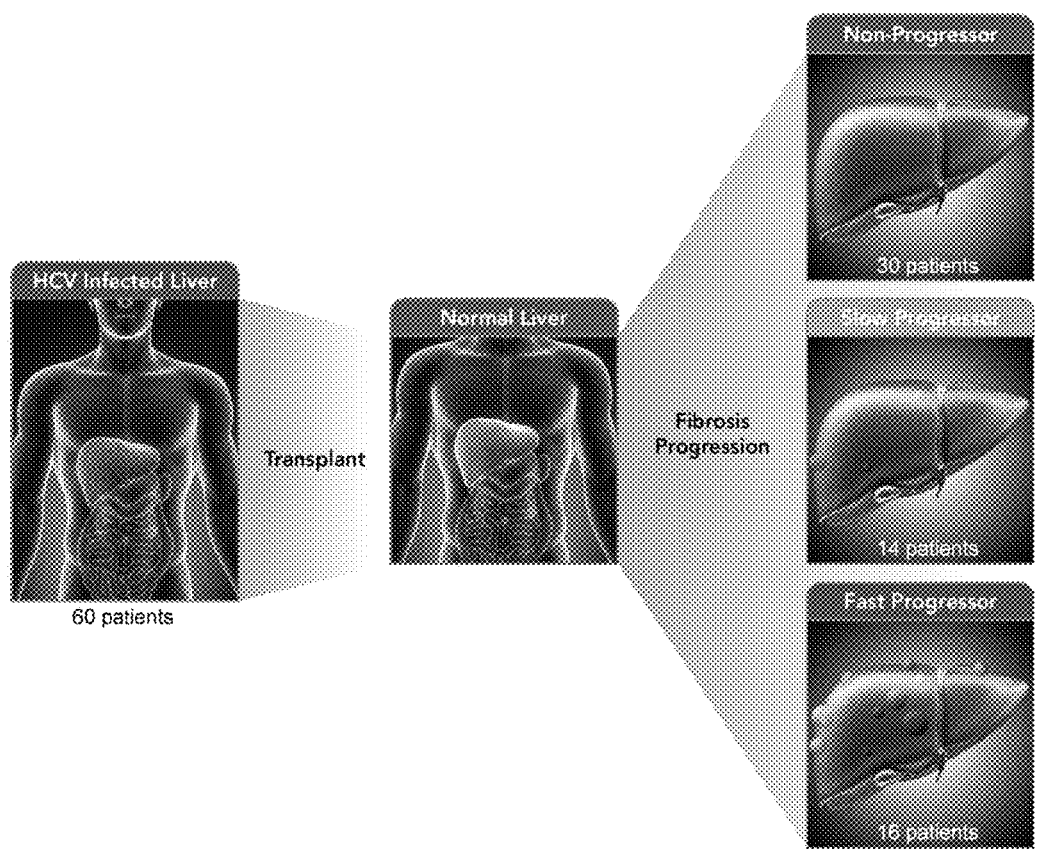
FIG. 3 illustrates the categorization of 60 HCV patients following liver transplant. Blood samples from the 60 HCV patients following liver transplant were utilized. Based on the amount of fibrosis occurring in each patient's liver several months to a few years following the procedure, the patients were categorized into non-, slow or fast progressing liver fibrosis groups. A biostatistician selected patients for the study so that a non-progressor patient could be donor, age and cold ischemia time matched to either a slow or fast progressor, resulting in 30 well-annotated patient pairs.

SEQ ID NOS: 1-5544 show peptide sequences that were detected using the disclosed methods.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural proteins and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. While the methods have been described and were utilized in testing, it is to be distinctly understood that the disclosure is not limited to any particular form of testing utilized, but is intended to include all methods that are capable of detecting the materials that are set forth in the claims. All references provided herein are incorporated by reference, as are the sequences associated with the GenBank Accession number provided herein (sequences available on Mar. 14, 2013).

Alarm: A notification (such as an audio or visual (e.g., color, picture, or text) notification) indicating the presence or absence of liver fibrosis, the presence or absence of fast-progressing liver fibrosis, the presence or absence of slow-progressing liver fibrosis, and/or the presence or absence of non-progressing liver fibrosis. The alarm may be activated when analysis of a subject's sample yields results meeting criteria for liver fibrosis, fast-progressing liver fibrosis, slow-progressing liver fibrosis, and/or non-progressing liver fibrosis. The criteria may be determined by the manufacturer of a kit, system, or device that includes the alarm or may, alternatively, be activated based upon a standard as entered by a clinician or other end-user.

Antibody: A polypeptide ligand including at least a light chain or heavy chain immunoglobulin variable region which specifically recognizes and binds an epitope of an antigen, such as a liver fibrosis marker or a fragment thereof (such as the proteins or peptides listed in any of Tables 1, 2, 3, 5, 6 and 12, as well as any of SEQ ID NOS: 1-5544). Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. In one example, an antibody specifically binds to one of the proteins or peptides listed in any of Tables 1, 2, 3, 5, 6 and 12, as well as any of SEQ ID NOS: 1-5544, but not other proteins (such as other proteins found in human serum or plasma).

This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda and kappa. There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds to a particular liver fibrosis marker will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds to one of the proteins or peptides listed in any of Tables 1, 2, 3, 5, 6 and 12, as well as any of SEQ ID NOS: 1-5544.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Array: An arrangement of molecules, such as biological macromolecules (such as peptides, antibodies, aptamers, aptazymes or nucleic acid molecules, such as nucleic acid probes), in addressable locations on or in a substrate. A "microarray" is an array that is miniaturized so as to require or be aided by microscopic examination for evaluation or analysis.

The array of molecules ("features") makes it possible to carry out a very large number of analyses on a sample at one time. In certain example arrays, one or more molecules (such as oligonucleotide probes, aptamers, aptazymes, or antibodies) will occur on the array a plurality of times (such as twice), for instance to provide internal controls. The number of addressable locations on the array can vary, for example from at least two, at least 3, at least 4, at least 5, at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes aptamers, aptazymes, or antibodies to detect target proteins.

In particular examples, an array includes oligonucleotide probes or primers which can be used to detect liver fibrosis-associated nucleic acids. Protein-based arrays include probe molecules that are or include proteins, or where the target molecules are or include proteins, and arrays including nucleic acids to which proteins are bound, or vice versa. For example, such arrays can be used to detect any combination of at least two of the liver fibrosis-related proteins (or nucleic acids encoding such proteins) listed in any of Tables 1, 2, 3, 5, 6 and 12, as well as any of SEQ ID NOS: 1-5544, such as at least 3, at least 4, at least 5, at least 6, at least 7, at least 8, at least 9, at least 10, at least 15, at least 20, at least 22, at least 25, at least 30, at least 35, at least 40, or at least 45 of the molecules listed in any of Tables 1, 2, 3, 5, 6 and 12, as well as any of SEQ ID NOS: 1-5544.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Binding affinity: Affinity of one molecule for another, such as an antibody, aptamer, or aptazyme for an antigen (for example, the proteins or peptides shown in any of Tables 1, 2, 3, 5, 6 and 12, as well as any of SEQ ID NOS: 1-5544). In one example, affinity is calculated by a modification of the Scatchard method described by Frankel et al., Mol. Immunol., 16:101-106, 1979. In another example, binding affinity is measured by an antigen/antibody dissociation rate. In yet another example, a high binding affinity is measured by a competition radioimmunoassay. In several examples, a high binding affinity is at least about $1\times10^{-8}$ M. In other examples, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M. The determination that a particular agent binds substantially only to a single liver fibrosis marker peptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Control: A sample, standard, or reference value(s) used for comparison with a test sample. In some embodiments, the control is a sample obtained from a healthy patient (or plurality of patients) (also referred to herein as a "normal" control), such as a normal sample (e.g., one from a patient(s) that does not have liver fibrosis). In some embodiments, the control is a historical control or standard value(s) (e.g., a previously tested control sample or group of samples that represent baseline or normal values). In some embodiments the control is a standard value representing the average value (or average range of values) obtained from a plurality of patient samples, such as an average value of the amount (e.g., relative or absolute) for each protein or peptide listed in any of Tables 1, 2, 3, 5, 6 and 12, as well as any of SEQ ID NOS: 1-5544, in patients without liver fibrosis or in patients with non-progressing liver fibrosis.

A control can also be represented by a reference value or range of values representing an amount of activity or expression determined to be representative of a given condition. Reference values can include a range of values, real or relative expected to occur under certain conditions. These values can be compared with experimental values to determine if a given molecule is up-regulated or down-regulated in a particular sample. In one example, a reference value or range of values represents an amount of activity or expression of a liver fibrosis related protein or peptide in a sample, such as a sample from a patient that does not have liver fibrosis (and who may or may not have a liver transplant) or from a subject with no-progressing liver fibrosis. This value can then be used to determine if the subject from whom a test sample was obtained has liver fibrosis (such as fast- or slow-progressing liver fibrosis) or is at high risk for developing liver fibrosis (such as fast- or slow-progressing liver fibrosis) by comparing this reference value of expression to the level of expression detected in the test sample. In a particular example, a significant change in expression or activity in four or more liver fibrosis related molecules (such an increase or decrease of at least 10%, at least 20%, at least 30%, at least 40%, at least 50%, at least 75%, at least 80%, at least 90%, at least 100%, at least 150%, at least 200%, or at least 300% for those in any of Tables 1, 2, 3, 5, 6 and 12, as well as any of SEQ ID NOS: 1-5544) in a test sample as compared to such a reference value indicates that the subject has liver fibrosis or is at a high risk for liver fibrosis. In a particular example, a significant change in expression or activity in four or more liver fibrosis related molecules (such an increase or decrease of at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, or at least 2.5 fold for those in any of Tables 1, 2, 3, 5, 6 and 12, as well as any of SEQ ID NOS: 1-5544) in a test sample as compared to such a reference value indicates that the subject has liver fibrosis or is at a high risk for liver fibrosis.

Detect: To measure, determine, or identify the existence, occurrence, presence, or fact of something. General methods of detecting are known to the person of ordinary skill in the art and may be supplemented with the protocols and reagents disclosed herein. For example, included herein are methods of detecting a protein or peptide shown in any of Tables 1, 2, 3, 5, 6 and 12, as well as any of SEQ ID NOS: 1-5544. Detection can be qualitative or quantitative and may be direct or indirect. Detection can be in bulk, so that a macroscopic number of molecules can be observed simultaneously. Detection can also include identification of signals from single molecules using microscopy and such techniques as total internal reflection to reduce background noise.

Diagnosis: The process of identifying a disease by its signs, symptoms and/or results of one or more tests, such as those provided herein. The conclusion reached through that process is also called "a diagnosis." Forms of testing commonly performed include blood tests, medical imaging, genetic analysis, urinalysis, biopsy and analysis of biological samples obtained from a subject. In one example diagnosis is determining whether a subject has liver fibrosis. In another example, diagnosis is determining whether a subject has fast progressing liver fibrosis. In yet another example, diagnosis is determining whether a subject has slow progressing liver fibrosis.

Differential expression: A difference, such as an increase or decrease, in the conversion of the information encoded in a gene (such as a liver fibrosis related gene) into messenger RNA, the conversion of mRNA to a protein, or both. In an example, the difference is relative to a control or reference value, such as an amount of protein expression that is expected in a subject who does not have liver fibrosis. In another example, the difference is relative to a control or reference value, such as an amount of protein or gene expression that is expected in a subject that has a non-progressing liver fibrosis. In another example, the difference is relative to a control or reference value, such as an amount of protein or gene expression that is expected in a subject that has a slow-progressing liver fibrosis. Detecting differential expression can include measuring a change in gene or protein expression, such as a change in amount (e.g., qualitative or quantitative) of one or more liver fibrosis related proteins, such as those listed in any of Tables 1, 2, 3, 5, 6 and 12, as well as any of SEQ ID NOS: 1-5544.

Downregulated or inactivated: When used in reference to the expression of a protein, refers to any process which results in a decrease in production or expression of a protein, such as a decrease of at least 10%, at least 20%, at least 50%, or at least 90%, such as an at least 1.2-fold, at least 1.5 fold, at least 2-fold, at least 3-fold, at least 4-fold, or at least 5-fold decrease. Protein downregulation includes any significant decrease in the detectable protein in a sample. In certain examples, the detectable protein in a sample decreases by at least 10%, at least 20%, at least 50%, or at least 90%, such as at least 1.2-fold, at least 1.5 fold, at least 2-fold, at least 3-fold or at least 4-fold, as compared to a control (such an amount of the detectable protein in a sample from a normal subject, such as one without liver fibrosis). In one example, a control is a relative amount of protein expression in a serum sample from a subject who does not have liver fibrosis. Similarly, when used in reference to the expression of a nucleic acid, such as cDNA or mRNA, refers to any process which results in a decrease in production or expression of a nucleic acid, such as a decrease of at least 10%, at least 20%, at least 50%, or at least 90%, such as an at least 1.2-fold, at least 1.5 fold, at least 2-fold, at least 3-fold, at least 4-fold, or at least 5-fold decrease.

Label: A detectable compound. In some examples, a label is conjugated directly or indirectly to another molecule, such as an antibody, protein, or nucleic acid probe, to facilitate detection of that molecule. In this case, the molecule such as an antibody, nucleic acid probe, or protein is labeled with the detectable compound. The label can be capable of detection by, for example, ELISA, spectrophotometry, flow cytometry, or microscopy. Specific, non-limiting examples of labels include fluorophores, chemiluminescent agents, enzymatic linkages, and radioactive isotopes. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to an antibody or aptamer specific for a protein or peptide disclosed in any of Tables 1, 2, 3, 5, 6 and 12, as well as any of SEQ ID NOS: 1-5544 to allow for the diagnosis of liver fibrosis. In another example, a label is conjugated to a secondary antibody specific for an antibody which is in turn specific for a protein or peptide disclosed in any of Tables 1, 2, 3, 5, 6 and 12, as well as any of SEQ ID NOS: 1-5544 to allow for the diagnosis of liver fibrosis.

Liver Fibrosis: The scarring process that occurs in the liver in response to injury to the liver and involves excessive accumulation of extracellular matrix proteins such as collagen. Liver fibrosis is often a result of chronic inflammation of the liver due to, for example, infection with hepatitis C virus (HCV). Chronic inflammation leads to changes in liver structure, to slowing of blood circulation, and necrosis of liver cells. Liver fibrosis is a dynamic process that may progress or regress over periods as short as months. As scar tissue builds up, due to inflammation and the continuance of liver injury, it can eventually disrupt the metabolic functions of the liver. Advanced liver fibrosis can result in cirrhosis, liver failure, and portal hypertension and often requires liver transplantation (and can occur following liver transplantation).

Liver fibrosis may occur in one of at least four stages. Stage 1 liver fibrosis (portal stage) is characterized by normal sized triads, portal inflammation and possible subtle bile duct damage. Granulomas may be detected in Stage 1 liver fibrosis. Stage 2 liver fibrosis (periportal stage) may be characterized by enlarged triads, periportal fibrosis and/or inflammation. Stage 2 is characterized by the finding of a proliferation of small bile ducts. Stage 3 (septal stage) liver fibrosis is characterized by active and/or passive fibrous septa. Stage 4 is characterized by biliary cirrhosis and liver nodules.

Liver fibrosis may be associated with elevations of liver enzymes such as aspartate aminotransferase (AST), alanine aminotransferase (ALT) and alkaline phosphatase (AP). Elevated liver enzymes may show up in blood tests before any actual fibrosis occurs in response to the damage that leads to the fibrosis. The present disclosure provides non-invasive methods of diagnosing and prognosing liver fibrosis.

As liver functioning is impaired overt signs and symptoms may manifest including inflammation, pain in the area of the liver, loss of appetite, nausea and vomiting, jaundice (yellowing of the skin and the whites of the eyes), spider angioma, caput medusa (appearance of dilated veins on the abdomen), and discoloration of the skin in rash-like patches. Overt signs and/or symptoms may indicate that the scarring has progressed to a potentially dangerous level but will not occur in all cases or stages of liver fibrosis.

Liver-fibrosis-related molecule(s): A nucleic acid or protein (or fragment thereof) whose expression is affected by liver fibrosis. Specific exemplary proteins include those listed in Tables 1, 2, 3, 5, 6 and 12, as well as fragments thereof (such as the peptides in SEQ ID NOS: 1-5544), whose expression is altered (such as upregulated or downregulated) in response to liver fibrosis (such as slow- or fast-progressing liver fibrosis). Examples of liver fibrosis-related molecules whose expression is upregulated following development of liver fibrosis include those in Table 1 with a positive Log 2 fold change such as alpha-1-antitrypsin, galectin-3-binding protein, von Willebrand factor, complement protein C7, extracellular matrix protein 1, actin-cytoplasmic 1 (ACTB), and sulfhydryl oxidase 1, Hemoglobin subunit beta, apoliprotein E, and sex hormone binding globulin. Specific examples of liver fibrosis-related molecules whose expression is downregulated following development of liver fibrosis include those in Table 1 with a negative Log 2 fold change such as prothrombin, BCHE (Cholinesterase), Retinol binding protein 4, IGFALS, transthyretin, alpha-1-acid glycoprotein 1, alpha-1-acid glycoprotein 2, fibrinogen alpha chain, apolipoprotein C-Ill, serum albumin, Beta-Ala-His dipeptidase, Coagulation factor XI, Plasma kallikrein, and coagulation factor IX (as well as nucleic acids encoding such proteins).

Liver fibrosis-related molecules also include families of proteins, such as those associated with liver metabolism (e.g., F2, BCHE, RBP4, TTR, IGFALS, and IGFBP3), the innate immune response (e.g., CFI, C4A, C6, CBA, C7, MBL2, MASP2, and FCN3), oxidative stress (e.g., QSOX1, GPX3, and PRDX2), and liver fibrosis (e.g., F10, C5, VTN, ECM, LGALS3BP, and LUM).

Liver fibrosis-related molecules can be involved in or influenced by liver fibrosis in different ways, including causative (in that a change in a liver fibrosis-related protein leads to development of or progression to liver fibrosis) or resultive (in that development of or progression to liver fibrosis causes or results in a change in the liver fibrosis-related molecule).

Prognosis: To determine whether a subject will develop a disease in the future, such as the predisposition of a subject to develop liver fibrosis in the future, such as slow- or fast-progressing liver fibrosis.

Protein: An amino acid-based molecule as found in a mammal or other subject. Includes full length amino acid molecules, as well as a portion of the naturally occurring full-length amino acid based molecule, such as at least 10 contiguous amino acids of the full-length naturally occurring protein. A protein may accordingly be a peptide which may or may not be found in a mammal but may instead form part of a larger molecule present naturally in a mammal. As a specific example, the "proteins listed in any of Tables 1, 2, 3, 5, 6 and 12, as well as any of SEQ ID NOS: 1-5544" includes the full-length listed proteins, fragments of at least 10 contiguous amino acids of each of the listed proteins (such as the peptides in any of SEQ ID NOS: 1-5544), a precursor (e.g., a pro-protein or a pre-pro-protein) of the listed proteins, or an amino-acid based metabolite of one of the listed proteins.

Sample: Biological specimens containing protein and/or nucleic acid molecules, such as those present in peripheral blood or fraction thereof, urine, saliva, tissue biopsy (such as a liver biopsy sample), surgical specimen, fine needle aspirates, and autopsy material. In one example, a sample includes plasma or serum obtained from a mammalian subject. In one example, the sample is a liquid sample.

Subject: Living multicellular vertebrate organisms having a liver. This term includes both human and veterinary subjects who have a liver, such as those that are in need of the desired diagnosis, such as diagnosis of liver fibrosis. Examples of mammals include, but are not limited to: humans, pigs, cows, goats, cats, dogs, rabbits and mice. In one example, a subject has or is susceptible to developing liver fibrosis, such as one infected with hepatitis B or C. In one example, the subject has received a liver transplant.

Therapeutically effective amount: A dose sufficient to prevent advancement, delay progression, or to cause regression of a disease, or which is capable of reducing symptoms caused by the disease, such as liver fibrosis. In one example, a therapeutically effective amount is an amount of a therapy sufficient to reduce inflammation in the liver, reduce liver enzyme levels (such as AST, ALT, and/or AP) and/or reduce scarring of the liver by at least 10%, at least 20%, at least 50%, at least 70%, or at least 90%. In one example, a therapeutically effective amount is an amount of a therapy sufficient to increase liver function in a fibrotic liver, for example an increase of at least 10%, at least 20%, at least 50%, at least 70%, or at least 90% as compared to an absence of therapy.

Upregulated or activated: When used in reference to the expression of a protein, refers to any process which results in an increase in production or expression of a protein, such as an increase of at least 10%, at least 20%, at least 50%, or at least 90%, such as an at least 1.2-fold, at least 1.5 fold, at least 2-fold, at least 3-fold, at least 4-fold, or at least 5-fold increase. Protein upregulation includes any significant increase in the detectable protein in a sample. In certain examples, the detectable protein in a sample increases by at least 10%, at least 20%, at least 50%, or at least 90%, such as 1.2-fold, at least 1.5 fold, at least at least 2-fold, at least 3-fold or at least 4-fold, as compared to a control (such an amount of the detectable protein in a sample from a normal subject). In one example, a control is a relative amount of protein expression in a serum sample from a subject who does not have liver fibrosis. Similarly, when used in reference to the expression of a nucleic acid, such as cDNA or mRNA, refers to any process which results in an increase in production or expression of a nucleic acid, such as an increase of at least 10%, at least 20%, at least 50%, or at least 90%, such as an at least 1.2-fold, at least 1.5 fold, at least 2-fold, at least 3-fold, at least 4-fold, or at least 5-fold increase relative to a control.

Overview

Rapid diagnosis and prognosis of disease using less invasive, safer, and more clinically acceptable approaches than presently employed is a goal for medicine. While mass spectrometry (MS)-based proteomics approaches have attempted to meet these objectives, challenges such as the enormous dynamic range of protein concentrations in clinically relevant biofluid samples coupled with the need to address human biodiversity have slowed their employment. Provided herein is the use of a new instrumental platform that addresses these challenges by coupling technical advances in rapid gas phase multiplexed ion mobility spectrometry (IMS) separations with liquid chromatography (LC) and MS to dramatically increase measurement sensitivity and throughput. Using this LC-IMS-MS platform, blood serum samples from 60 non-transplant and 60 post-liver transplant patients with recurrent fibrosis progression were analyzed, and relevant proteins and protein fragments identified. The multidimensional LC-IMS-MS platform provided herein greatly improves upon existing MS technologies in analytical sensitivity and specificity, enhances dynamic range of measurements, and provides reliable identification and quantitation of low abundance analyte species in highly complex biological matrices. Additionally the enhanced throughput of the new platform demonstrate the ability of this technology in clinical studies Thus, coupling ion mobility spectrometry (IMS) separation to MS can increase measurement sensitivity while simultaneously reducing analysis time, allowing the IMS-MS platform to be used to identify clinically relevant proteins. These proteins and peptide fragments can be detected in a biological sample, such as blood or a fraction thereof, to diagnose or prognose liver fibrosis.

Based on this identification, methods, systems, and kits are provided for diagnosing and/or prognosing liver fibrosis by analyzing the expression of several protein markers (or their corresponding nucleic acids) in a biological sample. Methods, systems, and kits are also provided for determining progression type (fast-progressing, slow-progressing and non-progressing) for subjects having liver fibrosis. Accurate detection and identification protein markers related to liver fibrosis, rather than more limited individual biomarkers, has been demonstrated herein. Use of larger panels of protein markers can aid in the reliable prognosis, diagnosis, tracking and determination of disease progression. Moreover, a method for reliable identification and quantitation of low abundance liver fibrosis-related proteins has been demonstrated. Early detection of liver fibrosis can be accomplished by comparing the expression levels of the liver fibrosis-related proteins (or nucleic acids) to control levels reflecting average protein (or nucleic acid) levels in a normal population or in relevant sub-populations. Alternatively, an individual's protein (or nucleic acid) abundances can be compared to a baseline panel established specifically for that person prior to disease onset. The method can performed using a variety of detection methods including immunoassays or mass spectrometry (MS) approaches.

One or more steps of the disclosed methods can be performed by a suitably-programmed computer. For example, the determined level of expression for the at least 2 liver fibrosis-related molecules listed in any of Tables 1, 2, 3, 5, 6 and 12, as well as any of SEQ ID NOS: 1-5544, in a sample obtained from the subject can be inputted into a computer or algorithm, which then generates an output, thereby analyzing the sample. In some examples, the output (such as a visual or audible output) is an indication as to whether the subject has or will likely develop fibrosis of the liver (such as a fast or slow-progressing fibrosis). This can allow a physician to identify those subjects who should receive anti-fibrosis therapy. Also provided are one or more non-transitory computer-readable media that include computer-executable instructions causing a computing system to perform the methods provided herein.

Systems for diagnosing or prognosing liver fibrosis in a subject are also provided. Such systems can include a means for measuring a level of at least two, at least 3, or at least 4 liver fibrosis-related molecules listed in any of Tables 1, 2, 3, 5, 6 and 12, as well as any of SEQ ID NOS: 1-5544, in a sample obtained from the subject. In some examples, such means include a mass spectrometer, ion mobility separator, liquid chromatography materials, light microscope, automated tissue or slide stainer, computer, or combinations thereof. In some examples, the system includes implemented rules for comparing the measured level of liver fibrosis-related molecules to one or more corresponding reference values or controls (for example to provide an indication as to whether there is differential expression). In some examples, the reference values are stored values or stored digital images. In some examples, the reference values are levels of liver fibrosis-related molecules measured from a control sample by said means for measuring. The system can also include one or more means for implementing the rules (such as a computer or algorithm), whereby a diagnosis or prognosis of liver fibrosis is provided based on the measured level of liver fibrosis-related molecules (for example if differential expression is detected).

Methods for Diagnosis and Prognosis of Liver Fibrosis

The disclosure provides methods for diagnosing liver fibrosis in a subject. Diagnosis can include determining that the subject currently has liver fibrosis, such as a slow-, or fast-progressing liver fibrosis. Also provided are methods for prognosing liver fibrosis in a subject. Prognosis can include determining that the subject will develop liver fibrosis in the future, such as a non-progressing, slow- or fast-progressing liver fibrosis, or include determining that current liver fibrosis in the subject will be non-progressing, slow- or fast-progressing liver fibrosis in the future.

The disclosed methods can include detecting a plurality of liver fibrosis-related molecules (e.g., at least 2, at least 3, or at least 4, at least 5, at least 6, at least 7, at least 8, at least 9, or at least 10 proteins or corresponding nucleic acid molecules) in a sample obtained from the subject. For example, protein expression can be detected in a biological sample using routine methods (such as immunoassays and spectrometry). In one example, protein expression is detected in a sample using liquid chromatography ion mobility mass spectrometry (LC-IMS-MS). The detected liver fibrosis related molecules are compared to a control(s), wherein the control may represent expression of the same liver fibrosis-related molecules (e.g., proteins) in a subject who does not have liver fibrosis or who has non-progressing liver fibrosis. Liver fibrosis is diagnosed in the subject when differential expression of the two or more liver fibrosis-related molecules between the sample and the control is detected or observed. Similarly, liver fibrosis is prognosed in the subject when differential expression of the at least two (e.g., at least 3, at least 4, at least 5, at least 6, at least 7, at least 8, at least 9, or at least 10) liver fibrosis-related molecules between the sample and the control is detected.

Various methods can be employed to select the at least two (e.g., at least 3, at least 4, at least 5, at least 6, at least 7, at least 8, at least 9, or at least 10) liver fibrosis-related molecules for inclusion in the disclosed methods, kits or other panel. In some embodiments, the at least two (e.g., at least 3, at least 4, at least 5, at least 6, at least 7, at least 8, at least 9, or at least 10) liver fibrosis-related molecules are selected at least in part based on having a high level of differential expression such as, for example, at least 20% differential expression relative to a control representing the level of expression in a subject without liver fibrosis or with non-progressing liver fibrosis. In some embodiments, the at least two (e.g., at least 3, at least 4, at least 5, at least 6, at least 7, at least 8, at least 9, or at least 10) liver fibrosis-related molecules are selected at least in part based on having a high level of sensitivity, individually or in combination, such as at least 90%, 95%, 96%, 97%, 98% or 99% sensitivity for the diagnosis or prognosis of liver fibrosis (such as moderate to advanced liver fibrosis). In some embodiments, the at least two (e.g., at least 3, at least 4, at least 5, at least 6, at least 7, at least 8, at least 9, or at least 10) proteins are selected at least in part based on having a high level of specificity, individually or in combination, such as at least 90%, 95%, 96%, 97%, 98% or 99% specificity for the diagnosis or prognosis of liver fibrosis (such as moderate to advanced liver fibrosis). In some embodiments, the at least two (e.g., at least 3, at least 4, at least 5, at least 6, at least 7, at least 8, at least 9, or at least 10) liver fibrosis-related molecules are selected at least in part based on the ability to distinguish various types and/or levels of liver fibrosis based on the differential expression detected. For example, one or more of the liver fibrosis-related molecules can be chosen at least in part based on an expectation of increased expression of the protein in fast-progressing liver fibrosis relative to a control and decreased expression of the protein relative to the control in slow-progressing liver fibrosis (e.g., where control is no liver fibrosis or non-progressing liver fibrosis).

In some examples, the method is performed at least one month, at least two months, at least six months or at least one year before the onset of clinical signs and symptoms that indicate liver fibrosis, including signs and symptoms indicating fast-progressing or slow-progressing liver fibrosis, regardless of cause. Specifically, the method may be performed at least one month, at least two months, at least six months or at least one year before the onset of portal hypertension and/or clinical manifestations of portal hypertension such caput medusa and ascites. In some examples, the method is performed at least one month, at least two months, at least six months or at least one year before the elevation above the normal range in the subject of one, two or three of AST, ALT and alkaline phosphatase.

In various embodiments, the method detects or prognoses liver fibrosis with a sensitivity of at least 80%, at least 85%, at least 90% or at least 95%; and a specificity of at least 80%, at least 85%, at least 90% or at least 95%. In various embodiments, the method detects or prognoses fast-progressing liver fibrosis with a sensitivity of at least 80%, at least 85%, at least 90% or at least 95% and a specificity of at least 80%, at least 85%, at least 90% or at least 95%. In various embodiments, the method detects or prognoses slow-progressing liver fibrosis with a sensitivity of at least 80%, at least 85%, at least 90% or at least 95%; and a specificity of at least 80%, at least 85%, at least 90% or at least 95%. In some examples, differential expression of the at least two (e.g., at least 3, at least 4, at least 5, at least 6, at least 7, at least 8, at least 9, or at least 10) liver fibrosis-related molecules may be detected as early as 1 day, as early as 2 days, as early as 5 days, or as early as 10 days following the onset of pathological fibrotic change in the liver.

I. Exemplary Liver Fibrosis Related Molecules

This section provides descriptions for several exemplary liver fibrosis-related molecules which can be used in the disclosed methods and kits. In some examples, the disclosed methods or systems include detecting or measuring expression of at least 2, at least 3, at least 4, at least 5, at least 6, at least 7, at least 8, at least 9, at least 10, at least 11, at least 12, at least 13, at least 14, or at least 15 of the liver fibrosis-related molecules listed below, such as 2, 3, 4, 5, 6, 7, 8, 9, 10, 11, 12, 13, 14 or all 15 of the liver fibrosis-related molecules listed below.

In some examples, the disclosed methods include detecting or measuring expression of at least 2, at least 3, at least 4, or all 5 of QSOX1, ECM1, LGALS3BP, lumican and vitronectin. In some examples, the disclosed methods include detecting or measuring expression of at least 2, at least 3, at least 4, or all 5 of DOPA (DBH), transthyretin (TTR), cholinesterase (BCHE), retinol-binding protein (RBP4), and IGFALS. In some examples, the disclosed methods include detecting or measuring expression of at least 2, at least 3, at least 4 at least 5, at least 6, at least 7, at least 8, at least 9, or all 10 of QSOX1, ECM1, LGALS3BP, lumican, vitronectin, DOPA (DBH), transthyretin (TTR), BCHE, RBP4, and IGFALS. Similarly, in some examples, the disclosed kits include agents that permit detection or measurement of expression of at least 2, at least 3, at least 4, or all 5 of QSOX1, ECM1, LGALS3BP, lumican and vitronectin. In some examples, the disclosed kits include agents that permit detection or measurement of expression of at least 2, at least 3, at least 4, or all 5 of DOPA (DBH), TTR, BCHE, RBP4, and IGFALS. In some examples, the disclosed kits include agents that permit detection or measurement of expression of at least 2, at least 3, at least 4 at least 5, at least 6, at least 7, at least 8, at least 9, or all 10 of QSOX1, ECM1, LGALS3BP, lumican, vitronectin, DOPA (DBH), TTR, BCHE, RBP4, and IGFALS.

A. Extracellular matrix protein 1 (ECM1) (OMIM: 602201) is an extracellular protein containing motifs with a cysteine pattern characteristic of the cysteine pattern of the ligand-binding "double-loop" domains of the albumin protein family. This gene maps outside of the epidermal differentiation complex (EDC), a cluster of three gene families involved in epidermal differentiation. Alternatively spliced transcript variants encoding distinct isoforms have been described. Nucleic acid and protein sequences for ECM1 are publicly available. For example, GENBANK® Accession Nos.: NM_001202858.1 and NM_001252653.1 disclose exemplary ECM1 nucleic acid sequences, and GENPEPT® Accession Nos.: NP_001189787.1 (human) and NP_001239582.1 (mouse) disclose exemplary ECM1 protein sequences, all of which are incorporated by reference as provided by GENPEPT®/GENBANK® on Mar. 14, 2013. In certain examples, ECM1 has at least 80% sequence identity, for example at least 85%, 90%, 95%, or 98% sequence identity to a publicly available ECM1 sequence, and is upregulated in the presence of liver fibrosis.

B. Prothrombin (F2) (OMIM 176930) is a protein precursor enzymatically cleaved at two sites by activated Factor X (Xa) to produce thrombin. In the blood coagulation pathway, thrombin acts to convert factor XI to XIa, VIII to VIIIa, V to Va, and fibrinogen to fibrin. The F2 gene is located on the chromosome 11 in humans (11p11-q12). Prothrombin is produced in the liver and is post-translationally modified in a vitamin K-dependent reaction that converts ten glutamic acids on prothrombin to gamma-carboxyglutamic acid (Gla). Nucleic acid and protein sequences for F2 are publicly available. For example, GENBANK® Accession Nos.: NM_000506.2 (human) and NM_010168.2 (mouse) are exemplary F2 acid sequences, and GENPEPT® Accession Nos.: NP_000497.1 (human) and NP_034298.1 (mouse) disclose exemplary F2 protein sequences, all of which are incorporated by reference as provided by GENPEPT®/GENBANK® on Mar. 14, 2013. In certain examples, prothrombin has at least 80% sequence identity, for example at least 85%, 90%, 95%, or 98% sequence identity to a publicly available prothrombin sequence, and is downregulated in the presence of liver fibrosis.

C. Complement C4-A (C4-A) (OMIM 120810) a protein precursor forming part of the classical activation blood coagulation pathway. The protein is expressed as a single chain precursor which is proteolytically cleaved into a trimer of alpha, beta, and gamma chains prior to secretion. The trimer provides a surface for interaction between the antigen-antibody complex and other complement components. The alpha chain may be cleaved to release C4 anaphylatoxin, a mediator of local inflammation. This gene localizes to the major histocompatibility complex (MHC) class III region on chromosome 6 in humans. Nucleic acid and protein sequences for C4-A are publicly available. For example, GENBANK® Accession Nos.: NM_001252204.1 (human) and NM_009780.2 (mouse) are exemplary C4-A nucleic acid sequences, and GENPEPT®/GENBANK® Accession Nos.: NP_001239133.1 (human) and AAI41051.1 (mouse) disclose exemplary C4-A protein sequences, all of which are incorporated by reference as provided by GENPEPT®/GENBANK® on Mar. 14, 2013. In certain examples, C4-A has at least 80% sequence identity, for example at least 85%, 90%, 95%, or 98% sequence identity to a publicly available C4-A sequence, and is downregulated in the presence of liver fibrosis.

D. Sulfhydryl oxidase 1 (QSOX1) (OMIM: 603120; EC 1.8.3.2) is an enzyme whose expression is induced as fibroblasts begin to exit the proliferative cycle and enter quiescence. Nucleic acid and protein sequences for sulfhydryl oxidase are publicly available. For example, GENBANK® Accession Nos.: NM_001004128.2 (human) and NM_001024945.1 (mouse) are exemplary QSOX1 nucleic acid sequences, and GENPEPT® Accession Nos.: NP_001004128.1 (human) and NP_001020116.1 (mouse) disclose exemplary QSOX1 protein sequences, all of which are incorporated by reference as provided by GENPEPT®/GENBANK® on Mar. 14, 2013. In certain examples, QSOX1 has at least 80% sequence identity, for example at least 85%, 90%, 95%, or 98% sequence identity to a publicly available QSOX1 sequence, and is upregulated in the presence of liver fibrosis.

E. Galectin-3-binding protein (LGALS3BP) (OMIM: 600626) is a protein implicated in modulating cell-cell and cell-matrix interactions The full length 90K cDNA has been localized to chromosome 17q25 in humans. The native protein binds specifically to a human macrophage-associated lectin known as Mac-2 and also binds galectin 1. LGALS3BP has been found elevated in the serum of patients with cancer and in those infected by the human immunodeficiency virus (HIV). Nucleic acid and protein sequences for LGALS3BP are publicly available. For example, GENBANK® Accession Nos.: NM_005567.3 (human) and NM_011150.2 (mouse) are exemplary LGALS3BP nucleic acid sequences, and GENPEPT® Accession Nos.: NP_005558.1 (human) and NP_035280.1 (mouse) disclose exemplary LGALS3BP protein sequences, all of which are incorporated by reference as provided by GENPEPT®/GENBANK® on Mar. 14, 2013. In certain examples, LGALS3BP has at least 80% sequence identity, for example at least 85%, 90%, 95%, or 98% sequence identity to a publicly available LGALS3BP sequence, and is upregulated in liver fibrosis.

F. Coagulation Factor X (F10) (OMIM: 613872, EC 3.4.21.6) is an enzyme synthesized in the liver and requires vitamin K for its synthesis. Factor X is activated into factor Xa by both factor IX (with its cofactor, factor VIII) and factor VII with its cofactor, tissue factor. It acts by cleaving prothrombin in two places (an arg-thr and then an arg-ile bond), which yields the active thrombin. Nucleic acid and protein sequences for Coagulation Factor X are publicly available. For example, GENBANK® Accession Nos.: NM_000504.3 (human) and NM_001242368.1 (mouse) exemplary F10 nucleic acid sequences, and GENPEPT® Accession Nos.: NP_000495.1 (human) and NP_001229297.1 (mouse) disclose exemplary F10 protein sequences, all of which are incorporated by reference as provided by GENPEPT®/GENBANK® on Mar. 14, 2013. In certain examples, F10 has at least 80% sequence identity, for example at least 85%, 90%, 95%, or 98% sequence identity to a publicly available F10 sequence, and is upregulated in the presence of fast-progressing liver fibrosis but downregulated in the presence of slow-progressing liver fibrosis.

G. Cytoskeletal β-actin (Actin-cytoplasmic 1, ACTB) (OMIM: 102630) is a highly conserved actin protein involved in cell motility, structure and integrity. Nucleic acid and protein sequences for ACTB are publicly available. For example, GENBANK® Accession Nos.: NM_001101.3 (human) and NM_007393.3 (mouse) are exemplary ACTB nucleic acid sequences, and GENPEPT® Accession Nos.: NP_001092.1 (human) and NP_031419.1 (mouse) disclose exemplary ACTB protein sequences, all of which are incorporated by reference as provided by GENPEPT®/GENBANK® on Mar. 14, 2013. In certain examples, ACTB has at least 80% sequence identity, for example at least 85%, 90%, 95%, or 98% sequence identity to a publicly available ACTB sequence, and is upregulated in liver fibrosis.

H. Complement component 5 (C5) (OMIM: 120900) is a protein which plays an important role in inflammatory and cytotoxic processes. This protein is composed of alpha and beta polypeptide chains that are linked by a disulfide bridge. An activation peptide, C5a, which is an anaphylatoxin that possesses potent spasmogenic and chemotactic activity, is derived from the alpha polypeptide via cleavage with a convertase. The C5b macromolecular cleavage product can form a complex with the C6 complement component, and this complex is the basis for formation of the membrane attack complex, which includes additional complement components. Nucleic acid and protein sequences for C5 are publicly available. For example, GENBANK® Accession Nos.: NM_001735.2 (human) and NM_010406.2 (mouse) are exemplary C5 nucleic acid sequences, and GENPEPT® Accession Nos.: NP_001726.2 (human) and NP_034536.1 (mouse) disclose exemplary C5 protein sequences, all of which are incorporated by reference as provided by GENPEPT®/GENBANK® on Mar. 14, 2013. In certain examples, C5 has at least 80% sequence identity, for example at least 85%, 90%, 95%, or 98% sequence identity to a publicly available C5 sequence, and is upregulated in the presence of fast-progressing liver fibrosis but downregulated in the presence of slow-progressing liver fibrosis.

I. Vitronectin (VTN) (OMIM: 193190) is an abundant glycoprotein found in serum and the extracellular matrix that promotes cell adhesion and spreading, inhibits the membrane-damaging effect of the terminal cytolytic complement pathway, and binds to several serpin serine protease inhibitors. It is a secreted protein and exists in either a single chain form or a clipped, two chain form held together by a disulfide bond. Nucleic acid and protein sequences for VTN are publicly available. For example, GENBANK® Accession Nos.: NM_000638.3 (human) and NM_011707.2 (mouse) are exemplary VTN nucleic acid sequences, and GENPEPT® Accession Nos.: NP_000629.3 (human) and NP_035837.1 (mouse) disclose exemplary VTN protein sequences, all of which are incorporated by reference as provided by GENPEPT®/GENBANK® on Mar. 14, 2013. In certain examples, VTN has at least 80% sequence identity, for example at least 85%, 90%, 95%, or 98% sequence identity to a publicly available VTN sequence, and is up-regulated in the presence of fast-progressing liver fibrosis but down-regulated in the presence of slow-progressing liver fibrosis.

J. Lumican (LUM) (OMIM: 600616) is a protein which is the major keratan sulfate proteoglycan of the cornea but is also distributed in interstitial collagenous matrices throughout the body. Lumican may regulate collagen fibril organization and circumferential growth, corneal transparency, and epithelial cell migration and tissue repair. Nucleic acid and protein sequences for LUM are publicly available. For example, GENBANK® Accession Nos.: NM_002345.3 (human) and NM_008524.2 (mouse) are exemplary LUM nucleic acid sequences, and GENPEPT® Accession Nos.: NP_002336.1 (human) and NP_032550.2 (mouse) disclose exemplary LUM protein sequences, all of which are incorporated by reference as provided by GENPEPT®/GENBANK® on Mar. 14, 2013. In certain examples, LUM has at least 80% sequence identity, for example at least 85%, 90%, 95%, or 98% sequence identity to a publicly available LUM sequence, and is up-regulated in the presence of fast-progressing liver fibrosis but down-regulated in the presence of slow-progressing liver fibrosis.

K. Dopamine β-hydroxylase (DBH) (OMIM: 609312) is an enzyme (oxygenase) involved in the synthesis of small-molecule neurotransmitters and converts dopamine to norepinephrine. It is expressed in noradrenergic nerve terminals of the central and peripheral nervous systems, as well as in chromaffin cells of the adrenal medulla. Nucleic acid and protein sequences for DBH are publicly available. For example, GENBANK® Accession Nos.: NM_000787.3 (human) and NM_138942.3 (mouse) are exemplary DBH nucleic acid sequences, and GENPEPT®/GENBANK® Accession Nos.: NP_000778.3 (human) and NP_620392.2 (mouse) disclose exemplary DBH protein sequences, all of which are incorporated by reference as provided by GENPEPT®/GENBANK® on Mar. 14, 2013. In certain examples, DBH has at least 80% sequence identity, for example at least 85%, 90%, 95%, or 98% sequence identity to a publicly available DBH sequence, and is upregulated in the presence of liver fibrosis.

L. Transthyretin (TTR) (OMIM: 176300) is a protein and carrier of thyroxine (T4) and retinol binding protein (when bound to retinol). The liver secretes TTR into the blood, and the choroid plexus secretes TTR into the cerebrospinal fluid. Nucleic acid and protein sequences for TTR are publicly available. For example, GEN-BANK® Accession Nos.: NM_000371.3 (human) and NM_013697.5 (mouse) are exemplary TTR nucleic acid sequences, and GENPEPT®/GENBANK® Accession Nos.: NP_000362.1 (human) and NP_038725.1 (mouse) disclose exemplary TTR protein sequences, all of which are incorporated by reference as provided by GENPEPT®/GENBANK® on Mar. 14, 2013. In certain examples, TTR has at least 80% sequence identity, for example at least 85%, 90%, 95%, or 98% sequence identity to a publicly available TTR sequence, and is downregulated in the presence of liver fibrosis.

M. Butyrylcholinesterase (BCHE) (OMIM: 177400), also known as plasma cholinesterase or pseudocholinesterase, is a non-specific cholinesterase protein enzyme found primarily in the liver. Nucleic acid and protein sequences for BCHE are publicly available. For example, GENBANK® Accession Nos.: NM_000055.2 (human) and NM_009738.3 (mouse) are exemplary BCHE nucleic acid sequences, and GENPEPT®/GENBANK® Accession Nos.: NP_000046.1 (human) and NP_033868.3 (mouse) disclose exemplary BCHE protein sequences, all of which are incorporated by reference as provided by GEN-PEPT®/GENBANK® on Mar. 14, 2013. In certain examples, BCHE has at least 80% sequence identity, for example at least 85%, 90%, 95%, or 98% sequence identity to a publicly available BCHE sequence, and is downregulated in the presence of liver fibrosis.

N. Retinol-binding protein (RBP4) (OMIM: 180250) is a protein and specific carrier for retinol in the blood, delivering retinol from liver stores to peripheral tissues. Nucleic acid and protein sequences for RBP4 are publicly available. For example, GENBANK® Accession Nos.: NM_006744.3 (human) and NM_001159487.1 (mouse) are exemplary RBP4 nucleic acid sequences, and GENPEPT®/GEN-BANK® Accession Nos.: NP_006735.2 (human) and NP_001152959.1 (mouse) disclose exemplary RBP4 protein sequences, all of which are incorporated by reference as provided by GENPEPT®/GENBANK® on Mar. 14, 2013. In certain examples, RBP4 has at least 80% sequence identity, for example at least 85%, 90%, 95%, or 98% sequence identity to a publicly available RBP4 sequence, and is downregulated in the presence of liver fibrosis.

O. Insulin-like growth factor binding protein, acid labile subunit (IGFALS) (OMIM: 601489) is a serum protein that binds insulin-like growth factors, increasing their half-life and vascular localization. Nucleic acid and protein sequences for IGFALS are publicly available. For example, GENBANK® Accession Nos.: NM_001146006.1 (human) and NM_008340.3 (mouse) are exemplary IGFALS nucleic acid sequences, and GENPEPT®/GENBANK® Accession Nos.: NP_001139478.1 (human) and NP_032366.2 (mouse) disclose exemplary IGFALS protein sequences, all of which are incorporated by reference as provided by GENPEPT®/GENBANK® on Mar. 14, 2013. In certain examples, IGFALS has at least 80% sequence identity, for example at least 85%, 90%, 95%, or 98% sequence identity to a publicly available IGFALS sequence, and is downregulated in the presence of liver fibrosis.

II. Subjects

Liver fibrosis diagnosed or prognosed using the methods, systems, or kits herein can be due to any condition that results in cirrhosis or fibrosis, such as one or more of chronic alcohol exposure, hepatitis B virus (HBV) infection, non-alcoholic, steatohepatitis, hepatitis C virus (HCV) infection, Wilson's disease, alpha-1-antitrypsin deficiency, hemochromatosis, primary biliary cirrhosis, primary sclerosing cholangitis, and autoimmune hepatitis. Thus, in some examples, the subject to be diagnosed or prognosed is one having one or more of these conditions. In some examples, a subject having one or more of chronic alcohol exposure, hepatitis B virus infection, non-alcoholic, steatohepatitis, hepatitis C virus infection, Wilson's disease, alpha-1-antitrypsin deficiency, hemochromatosis, primary biliary cirrhosis, primary sclerosing cholangitis, and autoimmune hepatitis is selected for analysis with the disclosed methods.

Subjects that can be diagnosed or prognosed with the disclosed methods, systems, or kits include those that have or are suspected of having post-transplant liver fibrosis. Thus, in some examples, the method includes selecting a subject who has received a liver transplant. Subjects can be any subject with a liver, such as a mammal, for example a human or veterinary subject.

In some examples, the subject has previously received a liver transplant, and method is performed at least 10 days; at least 15 days; at least 30 days; at least 60 days; at least 90 days; at least 120 days; at least 200 days; at least 365 days; at least 2 years; or at least 3 years after liver transplant.

In some examples, the subject has been infected and/or exposed to HBV or HCV. Thus, in some examples the subject to be diagnosed or prognosed is one who has received a liver transplant and has been previously infected or exposed to HBV or HCV. For example, the disclosed methods can be is performed at least 6 months, at least 1 year, at least 2 years, at least 5 five years, at least 10 years, at least 15 years, at least 20 years, at least 25 years, or at least 30 years after the HBV or HCV exposure/infection.

In some examples, the subject is one who has been diagnosed with chronic alcoholism. Chronic alcoholism can lead to the accumulation of fatty deposits in the liver and eventual fibrosis, cirrhosis and liver failure. In some embodiments, the subject has chronic alcoholism and the method is performed at least 2 years, at least 3 years, at least 5 years, at least 10 years, at least 15 years, at least 20 years, at least 25 years, or at least 30 years after disease onset.

In some examples, the subject has alpha-antitrypsin (AAT) deficiency. Alpha-1 antitrypsin deficiency is an autosomal recessive genetic disorder causing both lung and liver diseases. There are several forms and degrees of deficiency, principally depending on whether the sufferer has one or two copies of the affected gene. The most common genotype of AAT deficiency is genotype PiZZ, which encodes mutant AAT, referred to as Z protein (ATZ). The fundamental pathological process of the AAT deficiency is the accumulation of mutant AAT as polymers within hepatocytes. The resultant low levels of AAT in the serum, result in lung damage by proteinases, and eventually emphysema. The protein accumulation in hepatocytes may play a role in the development of liver diseases, including chronic hepatitis, liver fibrosis, cirrhosis and hepatocellular carcinoma.

In some examples, the subject has hemochromatosis. Hereditary hemochromatosis (HH), is characterized by increased intestinal absorption of iron, which leads to deposition of iron in the body, e.g., in multiple organs such as liver, pancreas, heart and other organs. Excess iron deposition, if left untreated, causes tissue damage and fibrosis with irreversible damage to various organs, e.g. iron overloaded organs, e.g. endocrine dysfunction or hepatic fibrosis and cirrhosis.

In some examples, the subject has primary biliary cirrhosis (PBC). PBC is an autoimmune disease of the liver marked by the progressive destruction of small bile ducts of the liver, with the intralobular ducts affected early in the disease. When the ducts are damaged, bile may build up in the liver and over time damage the tissue and lead to scarring, fibrosis and cirrhosis. Those affected by PBC may present with symptoms of fatigue, pruritis (itchiness), jaundice and xanthomas.

In some examples, the subject has primary sclerosing cholangitis (PSC). PSC is a disease of the bile ducts that causes inflammation and subsequent obstruction of the bile ducts at an intra- and extra-hepatic level. The inflammation impedes the flow of bile to the gut which can lead to liver fibrosis, liver cirrhosis, liver failure and liver cancer. More than 80% of those with PSC have ulcerative colitis. Symptoms of PSC may be similar to those of PBC and can include pruritis, jaundice, fatigue, and malabsorption. Approximately 80% subjects with PSC have perinuclear anti-neutrophil cytoplasmic antibodies (p-ANCA).

In some examples, the subject has Wilson's disease. Wilson's disease, also known as hepatolenticular degeneration, is a rare inherited systemic disorder of copper metabolism. Individuals with Wilson's disease are unable to excrete copper into their bile, thus, copper begins to accumulate in the liver. Wilson's disease may cause acute or chronic hepatitis (inflammation of the liver) or cirrhosis (severe liver disease) due to a progressive loss of liver function. The degree of liver involvement is variable and may range from mild elevations of certain liver enzymes to complete liver failure. Symptoms associated with Wilson's disease include fatigue, anorexia, weight loss, generalized weakness, ascites and abdominal swelling, or jaundice. Other symptoms include enlargement of the liver (hepatomegaly), spleen (splenomegaly), or both (hepatosplenomegaly).

In some examples, the subject has nonalcoholic fatty liver disease (NAFLD) such as nonalcoholic steatohepatitis (NASH). Subjects with NAFLD have no drinking habit (less than 20 g daily), however give histological findings characterized by hepatic fatty deposition reminiscent of those found in alcoholic hepatic damage. The disease is regarded as a phenotype in the liver of metabolic syndrome accompanying obesity. NAFLD is divided into simple fatty liver and NASH. NASH is a progressive disease that frequently accompanies fibrosis and has been known to progress to hepatic cirrhosis and hepatic cancer. NAFLD may be suspected in subjects with high levels of triglyceride in the blood and may be diagnosed by abdominal ultrasonography and CT.

In some examples, the subject has autoimmune hepatitis. Autoimmune hepatitis is a disease of the liver that occurs when the body's immune system attacks cells of the liver. Anomalous presentation of human leukocyte antigen (HLA) class II on the surface of hepatocytes possibly due to a genetic predisposition or acute liver infection, causes a cell-mediated immune response against the body's own liver. This abnormal immune response results in inflammation of the liver, which can lead to further complications, including fibrosis and cirrhosis.

III. Differential Expression

Detecting differential expression can include measuring a change in gene or protein expression, such as a change in amount (e.g., qualitative or quantitative) of one or more liver fibrosis-related molecules (e.g., proteins, peptides, or nucleic acids). For example, measurement or detection of expression can be absolute or relative, and in some examples is quantified. In various embodiments, differential expression includes a detectable increase or decrease of at least 1.1-fold; at least 1.15-fold; at least 1.2-fold; at least 1.25-fold; at least 1.3-fold; at least 1.4-fold; at least 1.5-fold; at least 1.6-fold; at least 1.7-fold; at least 2-fold; at least 2.5-fold; at least 3-fold; at least 3.5-fold; or at least 4-fold relative to a control. In some embodiments, differential expression includes a detectable increase or decrease of at least 10%; at least 20%; at least 30%; at least 40%; at least 50%; at least 60%; at least 70%; at least 80%; at least 90%; at least 100%; at least 125%; at least 150%; at least 200%; at least 300%, or at least 400% relative to a control. In certain embodiments, differential expression of at least two (e.g., at least 3, at least 4, at least 5, at least 6, at least 7, at least 8, at least 9, or at least 10, such as 2, 5, 10 or 15) liver fibrosis-related molecules between the sample and the control is detected, wherein differential expression of at least 1.2 fold is detected for at least 50%; at least 75%; at least 80%; at least 90%; or all of the at least two (e.g., at least 3, at least 4, at least 5, at least 6, at least 7, at least 8, at least 9, or at least 10, such as 2, 5, 10 or 15) liver fibrosis-related molecules tested.

In one embodiment, the differential expression detected for each of the at least two (e.g., at least 3, at least 4, at least 5, at least 6, at least 7, at least 8, at least 9, or at least 10, such as 2, 5, 10 or 15) liver fibrosis-related molecules is compared to the expected differential expression for each liver fibrosis-related molecule for a subject with liver fibrosis to determine whether the detected differential expressions indicate a diagnosis of liver fibrosis. In some embodiments, the level of differential expression required to prognose the development of liver fibrosis will vary from the level required to diagnose the presence of liver fibrosis. In one embodiment, the required differential expression of the at least two (e.g., at least 3, at least 4, at least 5, at least 6, at least 7, at least 8, at least 9, or at least 10, such as 2, 5, 10 or 15) liver fibrosis-related molecules for prognosis of liver fibrosis is smaller than that required for diagnosis. In certain embodiments, the time at which differential expression of the at least two (e.g., at least 3, at least 4, at least 5, at least 6, at least 7, at least 8, at least 9, or at least 10, such as 2, 5, 10 or 15) liver fibrosis-related molecules is measured is earlier for prognosis than for diagnosis. In various embodiments, differential expression is measured at least 10 days, at least 30 days, at least 90 days, at least 2 months, at least 3 months, at least 6 months, at least 1 year, at least 2 years, at least 3 years, at least 5 years or at least 10 years earlier for prognosis of liver fibrosis than for diagnosis.

In certain embodiments, the at least two (e.g., at least 3, at least 4, at least 5, at least 6, at least 7, at least 8, at least 9, or at least 10, such as 2, 5, 10 or 15) liver fibrosis-related molecules are selected for their suitability for prognosis. In some embodiments, the at least two (e.g., at least 3, at least 4, at least 5, at least 6, at least 7, at least 8, at least 9, or at least 10, such as 2, 5, 10 or 15) liver fibrosis-related molecules are selected for prognosis on the basis of their showing differential expression at an early time point as compared to non-selected proteins. Exemplary markers that can be used for prognosis include VTN, LUM, and F10. In some embodiments, the at least two (e.g., at least 3, at least 4, at least 5, at least 6, at least 7, at least 8, at least 9, or at least 10, such as 2, 5, 10 or 15) liver fibrosis-related molecules are selected for diagnosis also on the basis of their showing differential expression at an earlier time point as compared to non-selected proteins. In various embodiments, a significant differential expression in the amount of the at least two (e.g., at least 3, at least 4, at least 5, at least 6, at least 7, at least 8, at least 9, or at least 10, such as 2, 5, 10 or 15) liver fibrosis related molecules in the serum or plasma (or other sample) of a subject compared to the amount of the same liver fibrosis related molecule found in a control is at least at a 1.1-fold, at least 1.2 fold, at least 1.5 fold, at least 2-fold, at least 3-fold, at least 4-fold or greater increase or decrease. Substantial differential expression, including overexpression or underexpression, of the at least two (e.g., at least 3, at least 4, at least 5, at least 6, at least 7, at least 8, at least 9, or at least 10, such as 2, 5, 10 or 15) or more liver fibrosis related molecule(s) can be indicative of the presence of liver fibrosis such as fast-progressing liver fibrosis or slow-progressing liver fibrosis.

In some examples, the control is a reference value or range of values representing a quantitative or qualitative amount of expression (e.g., protein, peptide, or nucleic acid) expected in a subject without liver fibrosis. In certain embodiments, the control is a predicted reference value or range of values representing a quantitative or qualitative amount of expression (e.g., protein, peptide, or nucleic acid) expected for the subject based on his/her personal characteristics such as health status, genetics and demographic information. In certain embodiments, the detected expression (e.g., protein, peptide, or nucleic acid) for a subject is compared to the protein expression for a matched control subject such as a control subject without liver fibrosis or with non-progressing liver fibrosis. In some embodiments, the control is a reference value or range of values representing a quantitative or qualitative amount of protein expression expected in a subject with non-progressing liver fibrosis. In some embodiments, the control is a reference value or range of values representing a quantitative or qualitative amount of protein expression expected in a subject with slow-progressing liver fibrosis. In some embodiments, the control is a reference value or range of values representing a quantitative or qualitative amount of protein expression expected in a subject with fast-progressing liver fibrosis. In some embodiments, the control is a reference value or range of values representing a quantitative or qualitative amount of protein expression expected in a subject without liver fibrosis but with HCV or HBV infection.

Tables 1-3 and 5-6 below provide differential expression information for specific liver fibrosis-related proteins. In one example, at least 10 or at least 15 of the peptides shown in any of SEQ ID NOS: 1-5544 are detected as an indication of protein expression. One skilled in the art will appreciate that as an alternative to detecting protein expression, expression of the corresponding nucleic acid molecule can be detected. In some examples, expression of the plurality of proteins or nucleic acids is detected simultaneously or contemporaneously in a sample. Furthermore, due to multiplexing technologies, one will appreciate that multiple samples, for example from different subjects, can be analyzed simultaneously or contemporaneously.

Table 1 provides directionality and relative amounts of differential expression detected for liver fibrosis-related proteins in subjects having post-transplant liver fibrosis (fast-progressing or slow-progressing) relative to matched controls representing the amount of protein expression in a subject with non-progressing liver fibrosis. Differential expression for the proteins ranged from 1.1-fold to more than 3-fold. Thus, expression of two or more of the liver fibrosis-related proteins (or corresponding peptides or nucleic acid molecules) in Table 1 can be used to diagnose or prognose liver fibrosis in a subject, such as by detecting expression of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, or all 136 of the proteins (or corresponding peptides or nucleic acid molecules) in Table 1. For example, if at least two of the liver fibrosis-related molecules in Table 1 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, or all 136 of the proteins) show the relative amount and direction of differential expression in the test sample, relative to a control (such as an amount of protein expression expected in a subject or population of subjects having non-progressing liver fibrosis), this results in a diagnosis of liver fibrosis, or a prognosis that the subject will develop liver fibrosis in the future.

Also shown in Table 1 is that 63 of the proteins also exhibited differential expression in non-transplant patients with liver fibrosis (see Table 5). Additionally, after excluding 4 proteins which decrease in SP, but increase in FP, >91% are observed with common abundance directionality with the non-transplant results (Table 12), providing strong orthogonal validation of the proteins based upon both transplant and non-transplant patients. 26 proteins (Ig kappa chain VA-III region VG, Ig kappa chain VA-III region HAH, Ig lambda chain VA-III region LOI, IGHA1, IGHG1, IGHG2, IGKC, IGKV1-5, IGLC1, FCGR3A, C7, HBB, LGALS3BP, MBL2, SERPINA1, SHBG, CNDP1, CNDP1, ALB, APOC3, C4A, FGA, ORM1, ORM2, TTR, and FN1) showed at least a 1.5-fold change in both slow- and fast-progressing liver fibrosis, and 10 proteins (Ig kappa chain VA-III region VG, Ig kappa chain VA-III region HAH, Ig lambda chain VA-III region LOI, IGHA1, IGHG1, IGHG2, IGKV1-5, SERPINA1, APOC3, and TTR) showed more than 2-fold differential expression in both slow- and fast-progressing liver fibrosis. Thus in some examples, these 26 proteins or 10 proteins are used in the methods and systems provided herein to diagnose or prognose liver fibrosis.

TABLE 1

Changes in 136 Liver Fibrosis Related Proteins in Slow- and/or Fast-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
|---|---|---|---|---|
| Proteins significantly upregulated in the Slow and Fast Progressors (SP & FP) compared to their matched controls | | | | |
| PTPRG | P23470 Receptor-type tyrosine-protein phosphatase gamma | X | | At least 1.2-fold |
| QSOX1 | O00391 Sulfhydryl oxidase 1 | X | | At least 1.4-fold |
| GPX3 | P22352 Glutathione peroxidase 3 | X | | At least 1.2-fold |
| . | P04433 Ig kappa chain V-III region VG | X | | At least 2-fold |
| . | P18135 Ig kappa chain V-III region HAH | X | | At least 2.2-fold |
| . | P80748 Ig lambda chain V-III region LOI | X | | At least 2.1-fold |
| IGHA1 | P01876 Ig alpha-1 chain C region | X | | At least 2.8-fold |
| IGHG1 | P01857 Ig gamma-1 chain C region | X | | At least 2.2-fold |
| IGHG2 | P01859 Ig gamma-2 chain C region | X | | At least 2.4-fold |
| IGHM | P01871 Ig mu chain C region | X | | At least 1.6-fold |
| IGKC | P01834 Ig kappa chain C region | X | | At least 1.8-fold |
| IGKV1-5 | P01602 Ig kappa chain V-I region HK102 | X | | At least 2-fold |
| IGLC1 | P01842 Ig lambda chain C regions | X | | At least 1.8-fold |
| FCGR3A | P08637 Low affinity immunoglobulin gamma Fc region receptor III-A | X | | At least 1.5-fold |
| A2M | P01023 Alpha-2-macroglobulin | X | | At least 1.4-fold |
| ACTB | Q96HG5 Actin, cytoplasmic 1 | X | | At least 1.2-fold |
| AFM | P43652 Afamin | X | | At least 1.3-fold |
| AHSG | P02765 Alpha-2-HS-glycoprotein | X | | At least 1.3-fold |
| ALCAM | Q13740 CD166 antigen | X | | At least 1.3-fold |
| APOB | Q13787 Apolipoprotein B-100 | X | | At least 1.2-fold |
| APOE | P02649 Apolipoprotein E | X | | At least 1.3-fold |
| C7 | P10643 Complement component C7 | X | | At least 1.8-fold |
| CLU | P10909 Clusterin | X | | At least 1.2-fold |
| ECM1 | Q8IZ60 Extracellular matrix protein 1 | X | | At least 1.3-fold |
| HBB | Q549N7 Hemoglobin subunit beta | X | | At least 1.5-fold |
| ITIH3 | Q06033 Inter-alpha-trypsin inhibitor heavy chain H3 | X | | At least 1.2-fold |
| LGALS3BP | Q08380 Galectin-3-binding protein | X | | At least 1.5-fold |
| MBL2 | P11226 Mannose-binding protein C | X | | At least 1.6-fold |
| SELL | P14151 L-selectin | X | | At least 1.2-fold |
| SERPINA1 | Q86U18 Alpha-1-antitrypsin | X | | At least 3-fold |
| SERPINA6 | P08185 Corticosteroid-binding globulin | X | | At least 1.2-fold |
| SHBG | P04278 Sex hormone-binding globulin | X | | At least 1.5-fold |
| VCAM1 | P19320 Vascular cell adhesion protein 1 | X | | At least 1.3-fold |
| VWF | P04275 von Willebrand factor | X | | At least 1.3-fold |
| Proteins significantly downregulated in the Slow and Fast Progressors (SP & FP) compared to their matched controls | | | | |
| F2 | P00734 Prothrombin | | X | At least 1.2-fold |
| CFB | Q9BX92 Complement factor B | | X | At least 1.1-fold |
| CFI | P05156 Complement factor I | | X | At least 1.1-fold |
| C1S | Q9UCV4 Complement C1s subcomponent | | X | At least 1.2-fold |
| C1R | P00736 Complement C1r subcomponent | | X | At least 1.2-fold |
| KLKB1 | P03952 Plasma kallikrein | | X | At least 1.3-fold |
| F11 | P03951 Coagulation factor XI | | X | At least 1.3-fold |

TABLE 1-continued

Changes in 136 Liver Fibrosis Related Proteins in Slow- and/or Fast-Progressing Liver Fibrosis relative to matched controls representing protein expression in a subject with non-progressing liver fibrosis

| Gene | Protein and UniProt Accession Number | Up-gulated | Down-regulated | Fold-Change vs. Control |
|---|---|---|---|---|
| F9 | P00740 Coagulation factor IX | | X | At least 1.2-fold |
| CNDP1 | Q96KN2 Beta-Ala-His dipeptidase | | X | At least 1.8-fold |
| BCHE | P06276 Cholinesterase | | X | At least 1.3-fold |
| ALB | Q9P157 Serum albumin | | X | At least 1.9-fold |
| APCS | P02743 Serum amyloid P-component | | X | At least 1.3-fold |
| APOA4 | P06727 Apolipoprotein A-IV | | X | At least 1.2-fold |
| APOC3 | P02656 Apolipoprotein C-III | | X | At least 2.2-fold |
| APOH | P02749 Beta-2-glycoprotein 1 | | X | At least 1.3-fold |
| AZGP1 | P25311 Zinc-alpha-2-glycoprotein | | X | At least 1.2-fold |
| C4A | Q5JQM8 Complement C4-A | | X | At least 1.5-fold |
| C6 | P13671 Complement component C6 | | X | At least 1.2-fold |
| C8A | P07357 Complement component C8 alpha chain | | X | At least 1.3-fold |
| C8B | P07358 Complement component C8 beta chain | | X | At least 1.3-fold |
| C8G | P07360 Complement component C8 gamma chain | | X | At least 1.2-fold |
| C9 | P02748 Complement component C9 | | X | At least 1.2-fold |
| FGA | P02671 Fibrinogen alpha chain | | X | At least 1.8-fold |
| HPX | P02790 Hemopexin | | X | At least 1.2-fold |
| HRG | P04196 Histidine-rich glycoprotein | | X | At least 1.3-fold |
| IGFALS | P35858 Insulin-like growth factor-binding protein complex acid labile subunit | | X | At least 1.3-fold |
| ITIH1 | P19827 Inter-alpha-trypsin inhibitor heavy chain H1 | | X | At least 1.3-fold |
| ITIH2 | P19823 Inter-alpha-trypsin inhibitor heavy chain H2 | | X | At least 1.1-fold |
| ITIH4 | Q14624 Inter-alpha-trypsin inhibitor heavy chain H4 | | X | At least 1.1-fold |
| ORM1 | P02763 Alpha-1-acid glycoprotein 1 | | X | At least 1.8-fold |
| ORM2 | P19652 Alpha-1-acid glycoprotein 2 | | X | At least 1.5-fold |
| PRG4 | Q92954 Proteoglycan 4 | | X | At least 1.2-fold |
| RBP4 | P02753 Retinol-binding protein 4 | | X | At least 1.1-fold |
| SERPINA3 | Q6NSC9 Alpha-1-antichymotrypsin | | X | At least 1.1-fold |
| SERPINC1 | Q9UC78 Antithrombin-III | | X | At least 1.1-fold |
| SERPIND1 | P05546 Heparin cofactor 2 | | X | At least 1.2-fold |
| TTR | P02766 Transthyretin | | X | At least 2.2-fold |
| Proteins showing opposing significant changes in the Slow and Fast Progressors (SP & FP) compared to matched controls | | | | |
| F10 | P00742 Coagulation factor X | X | X | Slow-Progressing: At least 1.2-fold (decrease) Fast-Progressing: At least 1.2 fold (increase) |
| FN1 | Q9HAP3 Fibronectin | X | X | Slow-Progressing: At least 1.5-fold (decrease) Fast-Progressing: At least 1.5-fold (increase) |
| C5 | P01031 Complement C5 | X | X | Slow-Progressing: At least 1.1-fold (increase) Fast-Progressing: At least 1.2-fold (increase) |
| SERPINA4 | P29622 Kallistatin | X | X | Slow-Progressing: At least 1.2-fold (decrease) Fast-Progressing: At least 1.3-fold (increase) |

TABLE 1-continued

Changes in 136 Liver Fibrosis Related Proteins in Slow- and/or Fast-Progressing Liver Fibrosis relative to matched controls representing protein expression in a subject with non-progressing liver fibrosis

| Gene | Protein and UniProt Accession Number | Up-gulated | Down-regulated | Fold-Change vs. Control |
|---|---|---|---|---|
| VTN | P04004 Vitronectin | X | X | Slow-Progressing: At least 1.1-fold (decrease) Fast-Progressing: At least 1.2-fold (increase) |
| LUM | P51884 Lumican | X | X | Slow-Progressing: At least 2.6-fold (decrease) Fast-Progressing: At least 1.1-fold (increase) |

Proteins significantly increasing/decreasing only in Slow Progressors (SP) compared to their matched controls

| Gene | Protein and UniProt Accession Number | Up-gulated | Down-regulated | Fold-Change vs. Control |
|---|---|---|---|---|
| HBA1 | P69905 Hemoglobin subunit alpha | X | | At least 2.1-fold |
| SERPING1 | Q96FE0 Plasma protease C1 inhibitor | X | | At least 1.4-fold |
| . | P01594 Ig kappa chain V-I region AU | X | | At least 3-fold |
| . | P01614 Ig kappa chain V-II region Cum | X | | At least 3.2-fold |
| IGKV4-1 | P06312 Ig kappa chain V-IV region | X | | At least 3.3-fold |
| PGLYRP2 | Q96PD5 N-acetylmuramoyl-L-alanine amidase | | X | At least 1.2 fold |
| BTD | P43251 Biotinidase | | X | At least 1.2 fold |
| PLG | P00747 Plasminogen | | X | At least 1.1 fold |
| PROC | P04070 Vitamin K-dependent protein C | | X | At least 1.6 fold |
| C1RL | Q9NZP8 Complement C1r subcomponent-like protein | | X | At least 1.2 fold |
| CPN1 | P15169 Carboxypeptidase N catalytic chain | | X | At least 1.1 fold |
| CPB2 | Q96IY4 Carboxypeptidase B2 | | X | At least 1.2 fold |
| APOA1 | P02647 Apolipoprotein A-I* | | X | At least 1.5 fold |
| C4B | Q9UIP5 Complement C4-B | | X | At least 1.5 fold |
| GC | P02774 Vitamin D-binding protein | | X | At least 1.1 fold |
| GP5 | P40197 Platelet glycoprotein V | | X | At least 1.2 fold |
| HP | P00738 Haptoglobin | | X | At least 1.4 fold |
| IGFBP3 | P17936 Insulin-like growth factor-binding protein 3* | | X | At least 1.3 fold |
| KNG1 | P01042 Kininogen-1 | | X | At least 1.3 fold |
| PROS1 | P07225 Vitamin K-dependent protein S | | X | At least 1.3 fold |
| SERPINA10 | Q9UK55 Protein Z-dependent protease inhibitor | | X | At least 1.4 fold |
| SERPINF1 | P36955 Pigment epithelium-derived factor | | X | At least 1.2 fold |
| SERPINF2 | P08697 Alpha-2-antiplasmin | | X | At least 1.1 fold |
| THBS1 | P07996 Thrombospondin-1 | | X | At least 1.4 fold |

Proteins significantly changing only in Fast Progressors (FP) compared to their matched controls

| Gene | Protein and UniProt Accession Number | Up-gulated | Down-regulated | Fold-Change vs. Control |
|---|---|---|---|---|
| PTGDS | P41222 Prostaglandin-H2 D-isomerase | X | | At least 1.2-fold |
| CA1 | P00915 Carbonic anhydrase 1 | X | | At least 2.1-fold |
| ALDOB | P05062 Fructose-bisphosphate aldolase B | X | | At least 1.7-fold |
| C2 | P06681 Complement C2 | X | | At least 1.2-fold |
| F12 | P00748 Coagulation factor XII | X | | At least 1.2-fold |
| MASP2 | Q9H498 Mannan-binding lectin serine protease 2 | X | | At least 1.2-fold |
| HABP2 | Q14520 Hyaluronan-binding protein 2 | X | | At least 1.4-fold |
| ANPEP | P15144 Aminopeptidase N | X | | At least 1.4-fold |
| ENPP2 | Q9UCR2 Ectonucleotide pyrophosphatase/phosphodiesterase family member 2 | X | | At least 1.5-fold |
| CP | P00450 Ceruloplasmin | X | | At least 1.1-fold |
| PRDX2 | P32119 Peroxiredoxin-2 | X | | At least 1.6-fold |
| A1BG | P04217 Alpha-1B-glycoprotein* | X | | At least 1.1-fold |
| TGFBI | Q53XM1 Transforming growth factor-beta-induced protein ig-h3 | X | | At least 1.4-fold |
| CD14 | P08571 Monocyte differentiation antigen CD14 | X | | At least 1.3-fold |
| C3 | P01024 Complement C3 | X | | At least 1.3-fold |

TABLE 1-continued

Changes in 136 Liver Fibrosis Related Proteins in Slow- and/or Fast-Progressing Liver Fibrosis relative to matched controls representing protein expression in a subject with non-progressing liver fibrosis

| Gene | Protein and UniProt Accession Number | Up-gulated | Down-regulated | Fold-Change vs. Control |
|---|---|---|---|---|
| ENG | P17813 Endoglin | X | | At least 1.3-fold |
| PROCR | Q9UNN8 Endothelial protein C receptor | X | | At least 1.2-fold |
| FCGBP | Q9Y6R7 IgGFc-binding protein | X | | At least 1.4-fold |
| FCN3 | O75636 Ficolin-3 | X | | At least 1.3-fold |
| FETUB | Q9UGM5 Fetuin-B | X | | At least 1.3-fold |
| MST1 | P26927 Hepatocyte growth factor-like protein | X | | At least 1.4-fold |
| MCAM | P43121 Cell surface glycoprotein MUC18 | X | | At least 1.2-fold |
| NRP1 | O14786 Neuropilin-1 | X | | At least 1.3-fold |
| SPP2 | Q13103 Secreted phosphoprotein 24 | X | | At least 1.4-fold |
| SERPINA7 | P05543 Thyroxine-binding globulin | X | | At least 1.5-fold |
| VASN | Q6EMK4 Vasorin | X | | At least 1.2-fold |
| COL18A1 | Q96T70 Collagen alpha-1(XVIII) chain | X | | At least 1.8-fold |
| PVR | P15151 Poliovirus receptor | X | | At least 1.6-fold |
| APOA2 | P02652 Apolipoprotein A-II | X | | At least 1.8-fold |
| PI16 | Q6UXB8 Peptidase inhibitor 16 | X | | At least 1.9-fold |
| H6PD | O95479 GDH/6PGL endoplasmic bifunctional protein | | X | At least 1.5-fold |
| AGT | P01019 Angiotensinogen | | X | At least 1.3-fold |
| CFH | Q9NU86 Complement factor H | | X | At least 1.2-fold |
| CRP | P02741 C-reactive protein | | X | At least 1.6-fold |
| GSN | P06396 Gelsolin | | X | At least 1.3-fold |

Table 2 provides directionality and relative amounts of differential expression detected for liver fibrosis-related proteins in subjects having post-transplant liver fibrosis which showed differential expression in fast-progressing liver fibrosis relative to matched controls representing the amount of protein expression in a subject with non-progressing liver fibrosis. Differential expression for the proteins ranged from 1.1-fold to more than 3-fold. The fold-change observed for those proteins showing differential expression in fast-progressing liver fibrosis is also provided in Table 2. A large group of the proteins (40) showed more than a 1.5-fold change in fast-progressing liver fibrosis, and 13 proteins showed more than a 2-fold change. Thus in some examples, these 40 proteins or 13 proteins are used in the methods and systems provided herein to diagnose or prognose fast-progressing liver fibrosis. 41 of the proteins either do not show differential expression in slow-progressing liver fibrosis or show differential expression in the opposite direction. Of these 41 proteins, 12 had more than a 1.5-fold change in fast-progressing liver fibrosis. Thus in some examples, these 12 proteins are used in the methods and systems provided herein to diagnose or prognose fast-progressing liver fibrosis.

Thus, expression of two or more of the liver fibrosis-related proteins (or corresponding peptides or nucleic acid molecules) in Table 2 can be used to diagnose or prognose fast-progressing liver fibrosis in a subject, such as by detecting expression of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, or all 112 of the proteins (or corresponding peptides or nucleic acid molecules) in Table 2. For example, if at least two of the liver fibrosis-related molecules in Table 2 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, or all 112 of the proteins) show the relative amount and direction of differential expression in the test sample, relative to a control (such as an amount of protein expression expected in a subject or population of subjects having non-progressing liver fibrosis), this results in a diagnosis of fast-progressing liver fibrosis, or a prognosis that the subject will develop a fast-progressing liver fibrosis in the future.

Similarly, expression of two or more of the liver fibrosis-related peptides in any of SEQ ID NOS: 1281-2633 can be used to diagnose or prognose fast-progressing liver fibrosis in a subject. Thus, expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, or 1353 of the liver fibrosis-related peptides in any of SEQ ID NOS: 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, and 2633, can be used to diagnose or prognose fast-progressing liver fibrosis in a subject. For example, if two or more of SEQ ID NOS: 1281-1869 are downregulated relative to a control (such as an amount of protein expression expected in a subject or population of subjects having non-progressing liver fibrosis), such as two or more of any of SEQ ID NOS: 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, and 1869, this can be used to diagnose or prognose fast-progressing liver fibrosis in a subject. In some examples, downregulation is a decrease of at least 0.5 fold, at least 0.8 fold, at least 1-fold, at least 2-fold, at least 2.5-fold, at least 3-fold, at least 3.5-fold, at least 4-fold or at least 4.5-fold. In addition, if two or more of SEQ ID NOS: 1870-2633 are upregulated relative to a control (such as an amount of protein expression expected in a subject or population of subjects having non-progressing liver fibrosis), such as two or more of any of SEQ ID NOS: 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, and 2633, this can be used to diagnose or prognose fast-progressing liver fibrosis in a subject. In some examples, the upregulation is an increase of at least 0.5 fold, at least 1-fold, at least 1.5-fold, at least 2-fold, at least 2.5-fold, at least 3-fold, or at least 3.3-fold.

In a specific example, expression of two or more of the liver fibrosis-related proteins (or corresponding peptides or nucleic acid molecules) labeled under "Proteins showing significant differential expression only in Fast-Progressing Liver Fibrosis" in Table 2 can be used to diagnose or prognose fast-progressing liver fibrosis in a subject, such as by detecting expression of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, or all 35 such proteins (or corresponding peptides or nucleic acid molecules) in Table 2. For example, if at least two of the liver fibrosis-related molecules in Table 2 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, or all 35 labeled under "Proteins showing significant differential expression only in Fast-Progressing Liver Fibrosis") show the relative amount and direction of differential expression in the test sample, relative to a control (such as an amount of protein expression expected in a subject or population of subjects having non-progressing liver fibrosis), this results in a diagnosis of fast-progressing liver fibrosis, or a prognosis that the subject will develop a fast-progressing liver fibrosis in the future.

In another example, expression of two or more (e.g., at least 3, at least 4) of the liver fibrosis-related proteins (or corresponding peptides or nucleic acid molecules) labeled under "Proteins showing significant differential expression in opposite directions for Fast and Slow-Progressing Liver Fibrosis" in Table 2 can be used to diagnose or prognose fast-progressing liver fibrosis in a subject, such as by detecting expression of at least 3, at least 4, at least 5 or all 6 such proteins (or corresponding peptides or nucleic acid molecules) labeled under "Proteins showing significant differential expression in opposite directions for Fast and Slow-Progressing Liver Fibrosis" in Table 2. For example, if at least two (e.g., at least 3, at least 4,) of the liver fibrosis-related molecules in Table 2, such as at least 5 or all 6 of the proteins labeled under "Proteins showing significant differential expression in opposite directions for Fast and Slow-Progressing Liver Fibrosis" show the relative amount and direction of differential expression (i.e., up-regulation) in the test sample, relative to a control (such as an amount of protein expression expected in a subject or population of subjects having non-progressing liver fibrosis), this results in a diagnosis of fast-progressing liver fibrosis, or a prognosis that the subject will develop a fast-progressing liver fibrosis in the future.

TABLE 2

112 Liver Fibrosis Related Proteins with Differential Expression in Post-Transplant Fast-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
|---|---|---|---|---|
| PTPRG | P23470 Receptor-type tyrosine-protein phosphatase gamma | | X | At least 1.2-fold |
| QSOX1 | O00391 Sulfhydryl oxidase 1 | X | | At least 1.7-fold |
| GPX3 | P22352 Glutathione peroxidase 3 | X | | At least 1.3-fold |
| . | P04433 Ig kappa chain V-III region VG | X | | At least 3.1-fold |
| . | P18135 Ig kappa chain V-III region HAH | X | | At least 2.3-fold |
| . | P80748 Ig lambda chain V-III region LOI | X | | At least 2.1-fold |

TABLE 2-continued

112 Liver Fibrosis Related Proteins with Differential Expression in Post-Transplant Fast-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
|---|---|---|---|---|
| IGHA1 | P01876 Ig alpha-1 chain C region | X | | At least 2.8-fold |
| IGHG1 | P01857 Ig gamma-1 chain C region | X | | At least 2.2-fold |
| IGHG2 | P01859 Ig gamma-2 chain C region | X | | At least 2.4-fold |
| IGHM | P01871 Ig mu chain C region | X | | At least 1.6-fold |
| IGKC | P01834 Ig kappa chain C region | X | | At least 1.8-fold |
| IGKV1-5 | P01602 Ig kappa chain V-I region HK102 | X | | At least 2-fold |
| IGLC1 | P01842 Ig lambda chain C regions | X | | At least 1.8-fold |
| FCGR3A | P08637 Low affinity immunoglobulin gamma Fc region receptor III-A | X | | At least 1.8-fold |
| A2M | P01023 Alpha-2-macroglobulin | X | | At least 1.5-fold |
| ACTB | Q96HG5 Actin, cytoplasmic 1 | X | | At least 1.2-fold |
| AFM | P43652 Afamin | X | | At least 1.3-fold |
| AHSG | P02765 Alpha-2-HS-glycoprotein | X | | At least 1.5-fold |
| ALCAM | Q13740 CD166 antigen | X | | At least 1.5-fold |
| APOB | Q13787 Apolipoprotein B-100 | X | | At least 1.2-fold |
| APOE | P02649 Apolipoprotein E | X | | At least 1.3-fold |
| C7 | P10643 Complement component C7 | X | | At least 2.1-fold |
| CLU | P10909 Clusterin | X | | At least 1.2-fold |
| ECM1 | Q8IZ60 Extracellular matrix protein 1 | X | | At least 1.3-fold |
| HBB | Q549N7 Hemoglobin subunit beta | X | | At least 1.5-fold |
| ITIH3 | Q06033 Inter-alpha-trypsin inhibitor heavy chain H3 | X | | At least 1.2-fold |
| LGALS3BP | Q08380 Galectin-3-binding protein | X | | At least 2.2-fold |
| MBL2 | P11226 Mannose-binding protein C | X | | At least 1.6-fold |
| SELL | P14151 L-selectin | X | | At least 1.3-fold |
| SERPINA1 | Q86U18 Alpha-1-antitrypsin | X | | At least 3-fold |
| SERPINA6 | P08185 Corticosteroid-binding globulin | X | | At least 1.2-fold |
| SHBG | P04278 Sex hormone-binding globulin | X | | At least 1.6-fold |
| VCAM1 | P19320 Vascular cell adhesion protein 1 | X | | At least 1.4-fold |
| VWF | P04275 von Willebrand factor | X | | At least 1.3-fold |
| F2 | P00734 Prothrombin | | X | At least 1.3-fold |
| CFB | Q9BX92 Complement factor B | | X | At least 1.2-fold |
| CFI | P05156 Complement factor I | | X | At least 1.1-fold |
| C1S | Q9UCV4 Complement C1s subcomponent | | X | At least 1.2-fold |
| C1R | P00736 Complement C1r subcomponent | | X | At least 1.2-fold |
| KLKB1 | P03952 Plasma kallikrein | | X | At least 1.3-fold |
| F11 | P03951 Coagulation factor XI | | X | At least 1.3-fold |
| F9 | P00740 Coagulation factor IX | | X | At least 1.2-fold |
| CNDP1 | Q96KN2 Beta-Ala-His dipeptidase | | X | At least 1.8-fold |
| BCHE | P06276 Cholinesterase | | X | At least 1.3-fold |
| ALB | Q9P157 Serum albumin | | X | At least 2.8-fold |
| APCS | P02743 Serum amyloid P-component | | X | At least 1.3-fold |
| APOA4 | P06727 Apolipoprotein A-IV | | X | At least 1.2-fold |
| APOC3 | P02656 Apolipoprotein C-III | | X | At least 2.4-fold |
| APOH | P02749 Beta-2-glycoprotein 1 | | X | At least 1.3-fold |
| AZGP1 | P25311 Zinc-alpha-2-glycoprotein | | X | At least 1.2-fold |
| C4A | Q5JQM8 Complement C4-A | | X | At least 1.5-fold |
| C6 | P13671 Complement component C6 | | X | At least 1.3-fold |
| C8A | P07357 Complement component C8 alpha chain | | X | At least 1.4-fold |
| C8B | P07358 Complement component C8 beta chain | | X | At least 1.3-fold |
| C8G | P07360 Complement component C8 gamma chain | | X | At least 1.2-fold |
| C9 | P02748 Complement component C9 | | X | At least 1.2-fold |
| FGA | P02671 Fibrinogen alpha chain | | X | At least 1.8-fold |
| HPX | P02790 Hemopexin | | X | At least 1.2-fold |
| HRG | P04196 Histidine-rich glycoprotein | | X | At least 1.3-fold |
| IGFALS | P35858 Insulin-like growth factor-binding protein complex acid labile subunit | | X | At least 1.3-fold |
| ITIH1 | P19827 Inter-alpha-trypsin inhibitor heavy chain H1 | | X | At least 1.3-fold |
| ITIH2 | P19823 Inter-alpha-trypsin inhibitor heavy chain H2 | | X | At least 1.1-fold |
| ITIH4 | Q14624 Inter-alpha-trypsin inhibitor heavy chain H4 | | X | At least 1.1-fold |
| ORM1 | P02763 Alpha-1-acid glycoprotein 1 | | X | At least 1.8-fold |
| ORM2 | P19652 Alpha-1-acid glycoprotein 2 | | X | At least 1.5-fold |
| PRG4 | Q92954 Proteoglycan 4 | | X | At least 1.2-fold |

TABLE 2-continued

112 Liver Fibrosis Related Proteins with Differential Expression in Post-Transplant Fast-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
|---|---|---|---|---|
| RBP4 | P02753 Retinol-binding protein 4 | | X | At least 1.1-fold |
| SERPINA3 | Q6NSC9 Alpha-1-antichymotrypsin | | X | At least 1.2-fold |
| SERPINC1 | Q9UC78 Antithrombin-III | | X | At least 1.2-fold |
| SERPIND1 | P05546 Heparin cofactor 2 | | X | At least 1.2-fold |
| TTR | P02766 Transthyretin | | X | At least 1.3-fold |
| *Proteins showing significant differential expression in opposite directions for Fast and Slow-Progressing Liver Fibrosis* | | | | |
| F10 | P00742 Coagulation factor X | X | | At least 1.2 fold |
| FN1 | Q9HAP3 Fibronectin | X | | At least 1.5-fold |
| C5 | P01031 Complement C5 | X | | At least 1.2-fold |
| SERPINA4 | P29622 Kallistatin | X | | At least 1.3-fold |
| VTN | P04004 Vitronectin | X | | At least 1.2-fold |
| LUM | P51884 Lumican | X | | At least 1.1-fold |
| *Proteins showing significant differential expression only in Fast-Progressing Liver Fibrosis* | | | | |
| PTGDS | P41222 Prostaglandin-H2 D-isomerase | X | | At least 1.2-fold |
| CA1 | P00915 Carbonic anhydrase 1 | X | | At least 2.1-fold |
| ALDOB | P05062 Fructose-bisphosphate aldolase B | X | | At least 1.7-fold |
| C2 | P06681 Complement C2 | X | | At least 1.2-fold |
| F12 | P00748 Coagulation factor XII | X | | At least 1.2-fold |
| MASP2 | Q9H498 Mannan-binding lectin serine protease 2 | X | | At least 1.2-fold |
| HABP2 | Q14520 Hyaluronan-binding protein 2 | X | | At least 1.4-fold |
| ANPEP | P15144 Aminopeptidase N | X | | At least 1.4-fold |
| ENPP2 | Q9UCR2 Ectonucleotide pyrophosphatase/phosphodiesterase family member 2 | X | | At least 1.5-fold |
| CP | P00450 Ceruloplasmin | X | | At least 1.1-fold |
| PRDX2 | P32119 Peroxiredoxin-2 | X | | At least 1.6-fold |
| A1BG | P04217 Alpha-1B-glycoprotein* | X | | At least 1.1-fold |
| TGFBI | Q53XM1 Transforming growth factor-beta-induced protein ig-h3 | X | | At least 1.4-fold |
| CD14 | P08571 Monocyte differentiation antigen CD14 | X | | At least 1.3-fold |
| C3 | P01024 Complement C3 | X | | At least 1.3-fold |
| ENG | P17813 Endoglin | X | | At least 1.3-fold |
| PROCR | Q9UNN8 Endothelial protein C receptor | X | | At least 1.2-fold |
| FCGBP | Q9Y6R7 IgGFc-binding protein | X | | At least 1.4-fold |
| FCN3 | O75636 Ficolin-3 | X | | At least 1.3-fold |
| FETUB | Q9UGM5 Fetuin-B | X | | At least 1.3-fold |
| MST1 | P26927 Hepatocyte growth factor-like protein | X | | At least 1.4-fold |
| MCAM | P43121 Cell surface glycoprotein MUC18 | X | | At least 1.2-fold |
| NRP1 | O14786 Neuropilin-1 | X | | At least 1.3-fold |
| SPP2 | Q13103 Secreted phosphoprotein 24 | X | | At least 1.4-fold |
| SERPINA7 | P05543 Thyroxine-binding globulin | X | | At least 1.5-fold |
| VASN | Q6EMK4 Vasorin | X | | At least 1.2-fold |
| COL18A1 | Q96T70 Collagen alpha-1(XVIII) chain | X | | At least 1.8-fold |
| PVR | P15151 Poliovirus receptor | X | | At least 1.6-fold |
| APOA2 | P02652 Apolipoprotein A-II | X | | At least 1.8-fold |
| PI16 | Q6UXB8 Peptidase inhibitor 16 | X | | At least 1.9-fold |
| H6PD | O95479 GDH/6PGL endoplasmic bifunctional protein | | X | At least 1.5-fold |
| AGT | P01019 Angiotensinogen | | X | At least 1.3-fold |
| CFH | Q9NU86 Complement factor H | | X | At least 1.3-fold |
| CRP | P02741 C-reactive protein | | X | At least 1.6-fold |
| GSN | P06396 Gelsolin | | X | At least 1.3-fold |

Table 3 provides directionality and relative amounts of differential expression detected for liver fibrosis-related proteins in subjects having post-transplant liver fibrosis which showed differential expression in slow-progressing liver fibrosis relative to matched controls representing the amount of protein expression in a subject with non-progressing liver fibrosis. Differential expression for the proteins ranged from 1.1-fold to more than 3-fold. Thus, expression of two or more of the liver fibrosis-related proteins (or corresponding peptides or nucleic acid molecules) in Table 3 can be used to diagnose or prognose slow-progressing liver fibrosis in a subject, such as by detecting expression of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, or all 101 of the proteins (or corresponding peptides or nucleic acid molecules) in Table 3. For example, if at least two of the liver fibrosis-related molecules in Table 3 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, or all 101 of the proteins) show the relative amount and direction of differential expression in the test sample, relative to a control (such as an amount of protein expression expected in a subject or population of subjects having non-progressing liver fibrosis), this results in a diagnosis of slow-progressing liver fibrosis, or a prognosis that the subject will develop a slow-progressing liver fibrosis in the future.

In a specific example, expression of two or more of the liver fibrosis-related proteins (or corresponding peptides or nucleic acid molecules) labeled under "Proteins showing significant differential expression only in Slow-Progressing Liver Fibrosis" in Table 3 can be used to diagnose or prognose slow-progressing liver fibrosis in a subject, such as by detecting expression of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or all 24 such proteins (or corresponding peptides or nucleic acid molecules) in Table 3. For example, if at least two of the liver fibrosis-related molecules in Table 3 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or all 24, such as 3, 4, 5, 6, 7, 8, 9, 10, 11, 12, 13, 14, 15, 16, 17, 18, 19, 20, 21, 22, 23, or 24, labeled under "Proteins showing significant differential expression only in Slow-Progressing Liver Fibrosis") show the relative amount and direction of differential expression in the test sample, relative to a control (such as an amount of protein expression expected in a subject or population of subjects having non-progressing liver fibrosis), this results in a diagnosis of slow-progressing liver fibrosis, or a prognosis that the subject will develop a slow-progressing liver fibrosis in the future.

In another example, expression of two or more of the liver fibrosis-related proteins (or corresponding peptides or nucleic acid molecules) labeled under "Proteins showing significant differential expression in opposite directions for Fast and Slow-Progressing Liver Fibrosis" in Table 3 can be used to diagnose or prognose slow-progressing liver fibrosis in a subject, such as by detecting expression of at least 3, at least 4, at least 5 or all 6 such proteins, such as 3, 4, 5, or 6 of the proteins (or corresponding peptides or nucleic acid molecules) labeled under "Proteins showing significant differential expression in opposite directions for Fast and Slow-Progressing Liver Fibrosis" in Table 3. For example, if at least two of the liver fibrosis-related molecules in Table 3, such as at least 3, at least 4, at least 5 or all 6 of the proteins labeled under "Proteins showing significant differential expression in opposite directions for Fast and Slow-Progressing Liver Fibrosis" show the relative amount and direction of differential expression (i.e., down-regulation) in the test sample, relative to a control (such as an amount of protein expression expected in a subject or population of subjects having non-progressing liver fibrosis), this results in a diagnosis of slow-progressing liver fibrosis, or a prognosis that the subject will develop a slow-progressing liver fibrosis in the future.

The fold-change relative to controls observed for the proteins demonstrating differential expression in slow-progressing liver fibrosis is provided in Table 3. A large group of the proteins (38) showed more than a 1.5-fold change in slow-progressing liver fibrosis, and 21 of these proteins showed more than a 2-fold change. Thus in some examples, these 38 proteins or 21 proteins are used in the methods and systems provided herein to diagnose or prognose slow-progressing liver fibrosis. 30 of the proteins listed with differential expression in slow-progressing liver fibrosis either did not show differential expression in fast-progressing liver fibrosis or exhibited differential expression in the opposite direction. Of these 30 proteins, 7 had more than a 1.5-fold change in slow-progressing liver fibrosis. Thus in some examples, these 7 proteins are used in the methods and systems provided herein to diagnose or prognose slow-progressing liver fibrosis.

Similarly, expression of two or more of the liver fibrosis-related peptides in any of SEQ ID NOS: 1-1280 can be used to diagnose or prognose slow-progressing liver fibrosis in a subject. Thus, expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, or 1280 of the liver fibrosis-related peptides in any of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, and 1280, can be used to diagnose or prognose slow-progressing liver fibrosis in a subject. For example, if two or more of SEQ ID NOS: 768-1280 are unregulated relative to a control (such as an amount of protein expression expected in a subject or population of subjects having non-progressing liver fibrosis), such as two or more of any of SEQ ID NOS: 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, and 1280, this can be used to diagnose or prognose slow-progressing liver fibrosis in a subject. In some examples, the upregulation is an increase of at least 0.1 fold, at least 0.5-fold, at least 1-fold, at least 1.5-fold, at least 2-fold, at least 2.5-fold, at least 3-fold, or at least 3.1-fold. In addition, if two or more of SEQ ID NOS: 1-767 are downregulated relative to a control (such as an amount of protein expression expected in a subject or population of subjects having non-progressing liver fibrosis), such as two or more of any of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, and 767, this can be used to diagnose or prognose slow-progressing liver fibrosis in a subject. In some examples, the downregulation is a decrease of at least 0.5 fold, at least 0.8 fold, at least 1-fold, at least 2-fold, at least 2.5-fold, at least 3-fold, at least 3.5-fold, or at least 4-fold.

TABLE 3

101 Liver Fibrosis Related Proteins with Differential Expression in Post-Transplant Slow-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
| --- | --- | --- | --- | --- |
| PTPRG | P23470 Receptor-type tyrosine-protein phosphatase gamma | | X | At least 1.3-fold |
| QSOX1 | O00391 Sulfhydryl oxidase 1 | | X | At least 1.4-fold |
| GPX3 | P22352 Glutathione peroxidase 3 | | X | At least 1.2-fold |
| . | P04433 Ig kappa chain V-III region VG | X | | At least 2 fold |
| . | P18135 Ig kappa chain V-III region HAH | X | | At least 3.2-fold |
| . | P80748 Ig lambda chain V-III region LOI | X | | At least 2.6-fold |
| IGHA1 | P01876 Ig alpha-1 chain C region | X | | At least 4.9-fold |
| IGHG1 | P01857 Ig gamma-1 chain C region | X | | At least 3.6-fold |
| IGHG2 | P01859 Ig gamma-2 chain C region | X | | At least 2.8-fold |
| IGHM | P01871 Ig mu chain C region | X | | At least 3.0 -fold |
| IGKC | P01834 Ig kappa chain C region | X | | At least 4.3-fold |
| IGKV1-5 | P01602 Ig kappa chain V-I region HK102 | X | | At least 2.3-fold |
| IGLC1 | P01842 Ig lambda chain C regions | X | | At least 4.2-fold |
| FCGR3A | P08637 Low affinity immunoglobulin gamma Fc region receptor III-A | | X | At least 1.5-fold |
| A2M | P01023 Alpha-2-macroglobulin | X | | At least 1.4-fold |
| ACTB | Q96HG5 Actin, cytoplasmic 1 | X | | At least 1.4-fold |
| AFM | P43652 Afamin | | X | At least 1.4-fold |
| AHSG | P02765 Alpha-2-HS-glycoprotein | | X | At least 1.3-fold |
| ALCAM | Q13740 CD166 antigen | | X | At least 1.3-fold |
| APOB | Q13787 Apolipoprotein B-100 | | X | At least 1.4-fold |
| APOE | P02649 Apolipoprotein E | | X | At least 1.5-fold |
| C7 | P10643 Complement component C7 | | X | At least 1.8-fold |
| CLU | P10909 Clusterin | | X | At least 1.3-fold |
| ECM1 | Q8IZ60 Extracellular matrix protein 1 | | X | At least 1.3-fold |
| HBB | Q549N7 Hemoglobin subunit beta | X | | At least 2.3-fold |

TABLE 3-continued

101 Liver Fibrosis Related Proteins with Differential Expression in Post-Transplant Slow-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
|---|---|---|---|---|
| ITIH3 | Q06033 Inter-alpha-trypsin inhibitor heavy chain H3 | X | | At least 1.2-fold |
| LGALS3BP | Q08380 Galectin-3-binding protein | X | | At least 1.5-fold |
| MBL2 | P11226 Mannose-binding protein C | X | | At least 1.7-fold |
| SELL | P14151 L-selectin | X | | At least 1.2-fold |
| SERPINA1 | Q86U18 Alpha-1-antitrypsin | X | | At least 3-fold |
| SERPINA6 | P08185 Corticosteroid-binding globulin | X | | At least 1.2-fold |
| SHBG | P04278 Sex hormone-binding globulin | X | | At least 1.5-fold |
| VCAM1 | P19320 Vascular cell adhesion protein 1 | X | | At least 1.3-fold |
| VWF | P04275 von Willebrand factor | X | | At least 1.3-fold |
| F2 | P00734 Prothrombin | | X | At least 1.2-fold |
| CFB | Q9BX92 Complement factor B | | X | At least 1.1-fold |
| CFI | P05156 Complement factor I | | X | At least 1.2-fold |
| C1S | Q9UCV4 Complement C1s subcomponent | | X | At least 1.3-fold |
| C1R | P00736 Complement C1r subcomponent | | X | At least 1.2-fold |
| KLKB1 | P03952 Plasma kallikrein | | X | At least 1.3-fold |
| F11 | P03951 Coagulation factor XI | | X | At least 1.5-fold |
| F9 | P00740 Coagulation factor IX | | X | At least 1.4-fold |
| CNDP1 | Q96KN2 Beta-Ala-His dipeptidase | | X | At least 1.8-fold |
| BCHE | P06276 Cholinesterase | | X | At least 1.5-fold |
| ALB | Q9P157 Serum albumin | | X | At least 1.9-fold |
| APCS | P02743 Serum amyloid P-component | | X | At least 1.5-fold |
| APOA4 | P06727 Apolipoprotein A-IV | | X | At least 1.1-fold |
| APOC3 | P02656 Apolipoprotein C-III | | X | At least 2.2-fold |
| APOH | P02749 Beta-2-glycoprotein 1 | | X | At least 1.4-fold |
| AZGP1 | P25311 Zinc-alpha-2-glycoprotein | | X | At least 1.2-fold |
| C4A | Q5JQM8 Complement C4-A | | X | At least 1.6-fold |
| C6 | P13671 Complement component C6 | | X | At least 1.2-fold |
| C8A | P07357 Complement component C8 alpha chain | | X | At least 1.3-fold |
| C8B | P07358 Complement component C8 beta chain | | X | At least 1.4-fold |
| C8G | P07360 Complement component C8 gamma chain | | X | At least 1.2-fold |
| C9 | P02748 Complement component C9 | | X | At least 1.2-fold |
| FGA | P02671 Fibrinogen alpha chain | | X | At least 4.0-fold |
| HPX | P02790 Hemopexin | | X | At least 1.3-fold |
| HRG | P04196 Histidine-rich glycoprotein | | X | At least 1.3-fold |
| IGFALS | P35858 Insulin-like growth factor-binding protein complex acid labile subunit | | X | At least 1.5-fold |
| ITIH1 | P19827 Inter-alpha-trypsin inhibitor heavy chain H1 | | X | At least 1.4-fold |
| ITIH2 | P19823 Inter-alpha-trypsin inhibitor heavy chain H2 | | X | At least 1.2-fold |
| ITIH4 | Q14624 Inter-alpha-trypsin inhibitor heavy chain H4 | | X | At least 1.2-fold |
| ORM1 | P02763 Alpha-1-acid glycoprotein 1 | | X | At least 2.3-fold |
| ORM2 | P19652 Alpha-1-acid glycoprotein 2 | | X | At least 2.1-fold |
| PRG4 | Q92954 Proteoglycan 4 | | X | At least 1.4-fold |
| RBP4 | P02753 Retinol-binding protein 4 | | X | At least 1.1-fold |
| SERPINA3 | Q6NSC9 Alpha-1-antichymotrypsin | | X | At least 1.1-fold |
| SERPINC1 | Q9UC78 Antithrombin-III | | X | At least 1.1-fold |
| SERPIND1 | P05546 Heparin cofactor 2 | | X | At least 1.4-fold |
| TTR | P02766 Transthyretin | | X | At least 2.2-fold |
| Proteins showing significant differential expression in opposite directions for Fast and Slow-Progressing Liver Fibrosis | | | | |
| F10 | P00742 Coagulation factor X | | X | At least 1.2-fold |
| FN1 | Q9HAP3 Fibronectin | | X | At least 1.5-fold |
| C5 | P01031 Complement C5 | | X | At least 1.1-fold |
| SERPINA4 | P29622 Kallistatin | | X | At least 1.1-fold |
| VTN | P04004 Vitronectin | | X | At least 1.1-fold |
| LUM | P51884 Lumican | | X | At least 2.6-fold |
| Proteins showing significant differential expression only in Slow-Progressing Liver Fibrosis | | | | |
| HBA1 | P69905 Hemoglobin subunit alpha | X | | At least 2.1-fold |
| SERPING1 | Q96FE0 Plasma protease C1 inhibitor | X | | At least 1.4-fold |
| . | P01594 Ig kappa chain V-I region AU | X | | At least 3-fold |
| . | P01614 Ig kappa chain V-II region Cum | X | | At least 3.2-fold |

TABLE 3-continued

101 Liver Fibrosis Related Proteins with Differential Expression in Post-Transplant Slow-Progressing Liver Fibrosis relative to matched controls representing protein expression in a subject with non-progressing liver fibrosis

| Gene | Protein and UniProt Accession Number | Up-regulated | Down-regulated | Fold-Change vs. Control |
|---|---|---|---|---|
| IGKV4-1 | P06312 Ig kappa chain V-IV region | X | | At least 3.3-fold |
| PGLYRP2 | Q96PD5 N-acetylmuramoyl-L-alanine amidase | | X | At least 1.2 fold |
| BTD | P43251 Biotinidase | | X | At least 1.2 fold |
| PLG | P00747 Plasminogen | | X | At least 1.1 fold |
| PROC | P04070 Vitamin K-dependent protein C | | X | At least 1.6 fold |
| C1RL | Q9NZP8 Complement C1r subcomponent-like protein | | X | At least 1.2 fold |
| CPN1 | P15169 Carboxypeptidase N catalytic chain | | X | At least 1.1 fold |
| CPB2 | Q96IY4 Carboxypeptidase B2 | | X | At least 1.2 fold |
| APOA1 | P02647 Apolipoprotein A-I* | | X | At least 1.5 fold |
| C4B | Q9UIP5 Complement C4-B | | X | At least 1.5 fold |
| GC | P02774 Vitamin D-binding protein | | X | At least 1.1 fold |
| GP5 | P40197 Platelet glycoprotein V | | X | At least 1.2 fold |
| HP | P00738 Haptoglobin | | X | At least 1.4 fold |
| IGFBP3 | P17936 Insulin-like growth factor-binding protein 3* | | X | At least 1.3 fold |
| KNG1 | P01042 Kininogen-1 | | X | At least 1.3 fold |
| PROS1 | P07225 Vitamin K-dependent protein S | | X | At least 1.3 fold |
| SERPINA10 | Q9UK55 Protein Z-dependent protease inhibitor | | X | At least 1.4 fold |
| SERPINF1 | P36955 Pigment epithelium-derived factor | | X | At least 1.2 fold |
| SERPINF2 | P08697 Alpha-2-antiplasmin | | X | At least 1.1 fold |
| THBS1 | P07996 Thrombospondin-1 | | X | At least 1.4 fold |

Table 4 summarizes the results in Tables 1-3. As indicated in Table 4, 77 proteins showed differential expression in both fast- and slow-progressing liver fibrosis (post-transplant subjects) with the differential expression having the same directionality for both groups in 71 out of 77 of the proteins. 34 proteins increased in the slow progressors (SP) and fast progressors (FP) compared to their matched controls, 37 proteins decreased in the SP and FP compared to their matched controls, 5 proteins only increased in the SP compared to their matched controls, 30 proteins only increased in the FP, 19 proteins only decreased in the SP, 5 proteins only decreased in the FP and 6 proteins increased in the FP and decreased in the SP.

TABLE 4

| Summary of Transplant Patients with Fibrosis | | |
|---|---|---|
| | FP | SP |
| Slow Progressors (SP) | 34↑ 37↓ | 5↑ 19↓ |
| Fast Progressors (FP) | 30↑ 5↓ | 6 (↑FP↓SP) |
| Total Significantly Changing Proteins | | 136 |

Table 5 provides directionality of differential expression for liver fibrosis-related proteins in non-transplant subjects having advanced liver fibrosis relative to controls with Stage 0-1 fibrosis. 40% of the proteins (31 out of 78 proteins) were up-regulated in the non-transplant subjects having advanced liver fibrosis and 60% of the proteins (47 out of 78 proteins) were down-regulated. 81% of the proteins in Table 5 (63 out of 78 proteins) also showed differential expression in the transplant group (i.e., appear in Table 1) with the majority (43 out of 78 proteins) being proteins showing differential expression in both slow- and fast-progressing post-transplant subjects (i.e., proteins appearing in both Table 2 and Table 3).

As discussed above, after excluding 4 proteins which decrease in SP, but increase in FP, >91% of the proteins with differential expression in the transplant group and non-transplant group are observed with common abundance directionality, providing a strong orthogonal validation of the proteins based upon both transplant and non-transplant studies. More extensive expression data, including data for specific peptides, is found in the Examples section below. Thus, expression of two or more of the liver fibrosis-related proteins (or corresponding peptides or nucleic acid molecules) in Table 5 can be used to diagnose or prognose liver fibrosis in a subject, such as by detecting expression of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, or all 78 of the proteins (or corresponding peptides or nucleic acid molecules) in Table 5. For example, if at least two of the liver fibrosis-related molecules in Table 2 (such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, or all 78 of the proteins) show the relative amount and direction of differential expression in the test sample, relative to a control (such as an amount of protein expression expected in a subject or population of subjects having non-progressing liver fibrosis), this results in a diagnosis of liver fibrosis, or a prognosis that the subject will develop liver fibrosis in the future.

TABLE 5

78 Liver Fibrosis Related Proteins having Differential Expression in Non-Transplant Stage 4-6 Liver Fibrosis subjects relative to Controls representing protein expression in a Non-Transplant Stage 0-1 Liver Fibrosis subject.

| Gene | Protein | Direction of Differential Expression |
|---|---|---|
| QSOX1 | O00391 Sulfhydryl oxidase 1 | ↑ |
| IGLC1 | P01842 Ig lambda chain C regions | ↑ |
| FCGR3A | P08637 Low affinity immunoglobulin gamma Fc region receptor III-A | ↑ |
| A2M | P01023 Alpha-2-macroglobulin | ↑ |
| AFM | P43652 Afamin | ↑ |
| ALCAM | Q13740 CD166 antigen | ↑ |
| APOB* | Q13787 Apolipoprotein B-100 | ↓ |
| C7 | P10643 Complement component C7 | ↑ |
| CLU | P10909 Clusterin | ↓ |
| ECM1 | Q8IZ60 Extracellular matrix protein 1 | ↑ |
| ITIH3 | Q06033 Inter-alpha-trypsin inhibitor heavy chain H3 | ↑ |
| LGALS3BP | Q08380 Galectin-3-binding protein | ↑ |
| VCAM1 | P19320 Vascular cell adhesion protein 1 | ↑ |
| VWF | P04275 von Willebrand factor | ↑ |
| F2 | P00734 Prothrombin | ↓ |
| CFI | P05156 Complement factor 1 | ↓ |
| KLKB1 | P03952 Plasma kallikrein | ↓ |
| F11 | P03951 Coagulation factor XI | ↓ |
| CNDP1 | Q96KN2 Beta-Ala-His dipeptidase | ↓ |
| BCHE | P06276 Cholinesterase | ↓ |
| APCS | P02743 Serum amyloid P-component | ↓ |
| APOH | P02749 Beta-2-glycoprotein 1 | ↓ |
| AZGP1 | P25311 Zinc-alpha-2-glycoprotein | ↓ |
| C4A | Q5JQM8 Complement C4-A | ↓ |
| C6 | P13671 Complement component C6 | ↓ |
| C8A | P07357 Complement component C8 alpha chain | ↓ |
| C8B | P07358 Complement component C8 beta chain | ↓ |
| C8G | P07360 Complement component C8 gamma chain | ↓ |
| HPX | P02790 Hemopexin | ↓ |
| IGFALS | P35858 Insulin-like growth factor-binding protein complex acid labile subunit | ↓ |
| ITIH1 | P19827 Inter-alpha-trypsin inhibitor heavy chain H1 | ↓ |
| ITIH2 | P19823 Inter-alpha-trypsin inhibitor heavy chain H2 | ↓ |
| ITIH4 | Q14624 Inter-alpha-trypsin inhibitor heavy chain H4 | ↓ |
| PRG4 | Q92954 Proteoglycan 4 | ↓ |
| RBP4 | P02753 Retinol-binding protein 4 | ↓ |
| SERPINC1 | Q9UC78 Antithrombin-III | ↓ |
| SERPIND1 | P05546 Heparin cofactor 2 | ↓ |
| TTR | P02766 Transthyretin | ↓ |
| APOC3 | P02656 Apolipoprotein C-III | ↓ |
| F10 | P00742 Coagulation factor X | ↓ |
| SERPINA4 | P29622 Kallistatin | ↓ |
| VTN | P04004 Vitronectin | ↑ |
| LUM | P51884 Lumican | ↑ |
| SERPING1 | Q96FE0 Plasma protease C1 inhibitor | ↑ |
| BTD | P43251 Biotinidase | ↓ |
| PLG | P00747 Plasminogen | ↓ |
| PROC | P04070 Vitamin K-dependent protein C | ↓ |
| CPN1 | P15169 Carboxypeptidase N catalytic chain | ↓ |
| CPB2 | Q96IY4 Carboxypeptidase B2 | ↓ |
| GC | P02774 Vitamin D-binding protein | ↓ |
| GP5 | P40197 Platelet glycoprotein V | ↓ |
| C2 | P06681 Complement C2 | ↓ |
| F12 | P00748 Coagulation factor XII | ↓ |
| ANPEP | P15144 Aminopeptidase N | ↑ |
| CP | P00450 Ceruloplasmin | ↑ |
| TGFBI | Q53XM1 Transforming growth factor-beta-induced protein ig-h3 | ↑ |
| FCGBP | Q9Y6R7 IgGFc-binding protein | ↑ |
| SERPINA7 | P05543 Thyroxine-binding globulin | ↓ |
| PVR | P15151 Poliovirus receptor | ↑ |
| AGT | P01019 Angiotensinogen | ↓ |
| H6PD | O95479 GDH/6PGL endoplasmic bifunctional protein | ↓ |
| PROCR | Q9UNN8 Endothelial protein C receptor | ↑ |
| VASN | Q6EMK4 Vasorin | ↑ |
| — | Ig lambda chain V-I region NEWM | ↑ |
| APOC1 | P02654 Apolipoprotein C-I | ↑ |
| ICAM1 | P05362 Intercellular adhesion molecule 1 | ↑ |
| CSF1R | P07333 Macrophage colony-stimulating factor 1 receptor | ↑ |
| DBH | P09172 Dopamine beta-hydroxylase | ↑ |
| COL6A3 | P12111 Collagen alpha-3(VI) chain | ↑ |
| COMP | P49747 Cartilage oligomeric matrix protein | ↑ |
| CD163 | Q86VB7 Scavenger receptor cysteine-rich type 1 protein M130 | ↑ |
| LYVE1 | Q9Y5Y7 Lymphatic vessel endothelial hyaluronic acid receptor 1 | ↑ |
| LCAT | P04180 Phosphatidylcholine-sterol acyltransferase | ↓ |
| CPN2 | P22792 Carboxypeptidase N subunit 2 | ↓ |
| PROZ | P22891 Vitamin K-dependent protein Z | ↓ |
| MASP1 | P48740 Mannan-binding lectin serine protease 1 | ↓ |
| SEPP1 | P49908 Selenoprotein P | ↓ |
| RARRES2 | Q99969 Retinoic acid receptor responder protein 2 | ↓ |

Table 6 lists the liver fibrosis-related proteins with differential expression only in fast-progressing (FP) post-transplant patients or only in slow-progressing (SP) post-transplant patients relative to controls representing protein expression in a patient with non-progressing liver fibrosis that also show differential expression in the same direction in non-transplant Stage 4-6 Liver Fibrosis subjects relative to Controls representing protein expression in a non-transplant Stage 0-1 Liver Fibrosis subject. Excluded from Table 6 are two proteins, F12 and Serpina7, which showed differential expression but in the opposite direction from the differential expression detected in SP or FP post-transplant subjects. Thus, for 90% (18 out of 20 proteins) of proteins with differential expression only in FP or SP that also showed differential expression in non-transplant patients, the differential expression was in the same direction as was detected for FP or SP post-transplant patients. 10 of the proteins in Table 6 show differential expression only in FP post-transplant patients, and 8 of the proteins in Table 6 show differential expression only in SP post-transplant patients.

TABLE 6

Liver Fibrosis Related Proteins with Differential Expression
in only Fast-Progressing (FP) Post-Transplant Patients or only
Slow-Progressing (SP) Post-Transplant patients relative to Controls
representing protein expression in a patient with Non-Progressing
Liver Fibrosis that show Differential Expression in the same
direction in Non-Transplant Stage 4-6 Liver Fibrosis subjects
relative to Controls representing protein expression in a Non-
Transplant Stage 0-1 Liver Fibrosis subject.

A. Proteins with Differential Expression only in SP Post-
Transplant Subjects that have co-directional Differential
Expression in Non-Transplant Stage 4-6 Subjects

| SERPING1 | Q96FE0 Plasma protease C1 inhibitor | ↑ |
| BTD | P43251 Biotinidase | ↓ |
| PLG | P00747 Plasminogen | ↓ |
| PROC | P04070 Vitamin K-dependent protein C | ↓ |
| CPN1 | P15169 Carboxypeptidase N catalytic chain | ↓ |
| CPB2 | Q96IY4 Carboxypeptidase B2 | ↓ |
| GC | P02774 Vitamin D-binding protein | ↓ |
| GP5 | P40197 Platelet glycoprotein V | ↓ |

B. Proteins with Differential Expression only in FP Post-
Transplant Subjects that have co-directional Differential
Expression in Non-Transplant Stage 4-6 Subjects

| C2 | P06681 Complement C2 | ↓ |
| ANPEP | P15144 Aminopeptidase N | ↑ |
| CP | P00450 Ceruloplasmin | ↑ |
| TGFBI | Q53XM1 Transforming growth factor-beta-induced protein ig-h3 | ↑ |
| FCGBP | Q9Y6R7 IgGFc-binding protein | ↑ |
| PVR | P15151 Poliovirus receptor | ↑ |
| AGT | P01019 Angiotensinogen | ↓ |
| H6PD | O95479 GDH/6PGL endoplasmic bifunctional protein | ↓ |
| PROCR | Q9UNN8 Endothelial protein C receptor | ↑ |
| VASN | Q6EMK4 Vasorin | ↑ |

In a specific example, expression of two or more of the liver fibrosis-related proteins (or corresponding peptides or nucleic acid molecules) labeled under "Proteins with Differential Expression only in FP Post-Transplant Subjects that have co-directional Differential Expression in Non-Transplant Stage 4-6 Subjects" in Table 6 can be used to diagnose or prognose fast-progressing liver fibrosis in a subject, such as by detecting expression of at least 3, at least 4, at least 5, at least 6, at least 7, at least 8, at least 9, at least 10 such proteins (or corresponding peptides or nucleic acid molecules) in Table 6. For example, if at least two of the liver fibrosis-related molecules in Table 6 (such as at least 3, at least 4, at least 5, at least 6, at least 7, at least 8, at least 9, or all 10 labeled under "Proteins with Differential Expression only in FP Post-Transplant Subjects that have co-directional Differential Expression in Non-Transplant Stage 4-6 Subjects") show differential expression in the test sample, relative to a control (such as an amount of protein expression expected in a subject or population of subjects having non-progressing liver fibrosis), this results in a diagnosis of fast-progressing liver fibrosis, or a prognosis that the subject will develop a fast-progressing liver fibrosis in the future.

In a specific example, expression of two or more of the liver fibrosis-related proteins (or corresponding peptides or nucleic acid molecules) labeled under "Proteins with Differential Expression only in SP Post-Transplant Subjects that have co-directional Differential Expression in Non-Transplant Stage 4-6 Subjects" in Table 6 can be used to diagnose or prognose slow-progressing liver fibrosis in a subject, such as by detecting expression of at least 3, at least 4, at least 5, at least 6, at least 7, or all 8 such proteins (or corresponding peptides or nucleic acid molecules) in Table 6. For example, if at least two of the liver fibrosis-related molecules in Table 6 (such as at least 3, at least 4, at least 5, at least 6, at least 7, or all 8 labeled under "Proteins with Differential Expression only in SP Post-Transplant Subjects that have co-directional Differential Expression in Non-Transplant Stage 4-6 Subjects") show differential expression in the test sample, relative to a control (such as an amount of protein expression expected in a subject or population of subjects having non-progressing liver fibrosis), this results in a diagnosis of slow-progressing liver fibrosis, or a prognosis that the subject will develop a slow-progressing liver fibrosis in the future.

IV. Progression of Liver Fibrosis

Rates of liver fibrosis progression can be described as fast, slow or non-progressing. In general, fast-progressing liver fibrosis progresses to an advanced stage (e.g., Stage 3-4 liver fibrosis) over a time period shorter than expected. Slow-progressing liver fibrosis progresses to an advanced stage over a time period longer than expected, and non-progressing liver fibrosis does not progress to an advanced stage of liver fibrosis over the course of a reasonable monitoring period. The expected rate of progression to liver fibrosis may depend upon the underlying cause. For example, in subjects having undergone liver transplantation, subjects may be categorized as having non-progressing liver fibrosis if no or mild return of fibrosis occurs over a time period of 2-4 years post-liver transplant. Subjects with slow progressing liver fibrosis may develop stage 3-4 fibrosis at three to four years post-transplant. Finally, subjects with fast progressing liver fibrosis may develop Stage 3-4 liver fibrosis within two years post-transplant.

Progression to liver fibrosis and advanced liver fibrosis may occur on a different schedule for subjects having other conditions causing liver fibrosis such as HCV infection (in a non-transplant subject), HBV infection, non-alcoholic fatty liver disease (NAFLD), Wilson's disease, alpha-1-antitrypsin deficiency, hemochromatosis, primary biliary cirrhosis, primary sclerosing cholangitis, and autoimmune hepatitis. For example, for a non-transplant subject infected with HCV, the expectation may be set according to the individual's age at the time of infection with HCV based on Poynard's fibrosis progression model (Poynard et al., 2001. J. Hepatol. 34: 730-9). For example, according to the Poynard model, a normal rate of progression to liver fibrosis in an individual younger than 20 years of age is 40 years. On the other hand, individuals who are infected at the age of 40 or older will develop liver fibrosis following 10-20 years from the time of infection. For a patient infected with HCV, this expectation may be set according to the Poynard fibrosis progression model discussed above. Accordingly, fast progressing liver fibrosis for a subject infected with HCV may refer to the development of liver fibrosis (e.g., stage 3 or higher) within a time period which is at least 5 years shorter than expected for a patient. Likewise, slow progressing liver fibrosis may refer to fibrosis which occurs over a time period which is at least 5 years longer than expected for a subject. Non-progressing liver fibrosis may refer to fibrosis which fails to develop or only manifests as mild fibrosis (e.g., stage 2 or lower) within a reasonable monitoring period. Based on the observation that fast-progression and slow-progression to fibrosis occurs over a time period that may depend on liver fibrosis cause, in various embodiments, fast-progression indicates progression to moderate or advanced liver fibrosis within less than 2 years, less than 3 years, less than 5 years, less than 10 years, less than 15 years, less than 20 years, less than 25 years, less than 30 years, or less than 40 years from a causative event or onset of a causative condition, such as 1 to 5 years, 1 to 10 years, or 2 to 20 years. Likewise, in various embodiments, slow-progressing liver fibrosis indicates progression to moderate or advanced liver fibrosis more than 2 years, more than 3 years, more than 5 years, more than 10 years, more than 15 years, more than 20 years, more than 25 years, more than 30 years, or more than 40 years after a causative event or onset of a causative condition, such as 2 to 5 years, 2 to 10 years, or 5 to 20 years.

The median estimated duration from the HCV infection date to the appearance of cirrhosis (end-stage liver fibrosis) is 30 years and approximately 33% of the patients progress to cirrhosis in less than 20 years (Poynard et al., 1997; Lancet. 349: 825-32). This indicates substantial variation in fibrosis progression rate and suggests that several host factors (e.g., factors related to the infected individual and not HCV itself), contribute to fibrosis progression. For example, older age, male gender, alcohol intake and immunosuppressant therapy can be associated with a less favorable outcome in terms of liver fibrosis [Poynard, supra]. Additionally, genetic factors can determine the natural history of liver diseases and the progression of liver fibrosis. These include genetic polymorphisms in genes encoding immuno-regulatory proteins, proinflammatory cytokines, and fibrogenic factors (Bataller et al., 2003. Hepatology. 37:493-503).

V. Detection of Liver Fibrosis-Related Nucleic Acid and Protein Molecules

The samples obtained from the subject (for example a serum or plasma sample) can contain altered levels of one or more nucleic acids or proteins associated with liver fibrosis, such as those listed in any of Tables 1, 2, 3, 5, 6 and 12, as well as any of SEQ ID NOS: 1-5544. Relative changes in expression or detected amounts can be detected to determine if a subject is predisposed to developing liver fibrosis, or has liver fibrosis. Although much of the disclosure focuses on detection of liver fibrosis-related proteins, one skilled in the art will appreciate that corresponding nucleic acid molecules (such as RNA, mRNA, DNA or cDNA) can be detected as a means to determine if expression of liver fibrosis-related molecules is altered. The present disclosure is not limited to particular methods of detecting proteins or nucleic acid molecules. Any method of detecting a nucleic acid molecule or protein can be used, such as physical or functional assays.

For example, the level of gene expression can be measured and quantified utilizing methods well known in the art, such as Northern-Blots, RNase protection assays, nucleic acid or antibody probe arrays, quantitative PCR (such as TaqMan assays), dot blot assays, in-situ hybridization, or combinations thereof. Using known techniques, a nucleic acid molecule may be first amplified prior to detection. In various embodiments, amplification of a nucleic acid or detection of a nucleic acid may be performed using a manual or automated technique or instrument. In addition, proteins can be detected or measured using immunological methods (such as antibody arrays [for example a lateral flow device, such as a point-of-care device, or an ELISA] or immunohistochemistry methods), quantitative spectroscopic methods (for example mass spectrometry, such as liquid chromatography ion mobility mass spectrometry (LC-IMS-MS), surface-enhanced laser desorption/ionization (SELDI)-based mass spectrometry or multiple reaction monitoring (MRM) based tandem mass spectrometry), or combinations thereof. In various embodiments, the expression level of a whole protein including the level of differential expression versus a control may be determined by detecting peptide fragments of the whole protein. In various embodiments detection of protein or fragment thereof may be performed using a manual or automated technique or instrument.

Methods for labeling nucleic acid molecules and proteins, as well as antibodies, so that they can be detected are well known. Examples of such labels include non-radiolabels and radiolabels. Non-radiolabels include, but are not limited to enzymes, chemiluminescent compounds, fluorophores, metal complexes, haptens, colorimetric agents, dyes, or combinations thereof. Radiolabels include, but are not limited to, $^{125}$I and $^{35}$S. Radioactive and fluorescent labeling methods, as well as other methods known in the art, are suitable for use with the present disclosure. In one example, the primers used to amplify the subject's nucleic acids are labeled (such as with biotin, a radiolabel, or a fluorophore), thereby permitting detection of the amplicons. In another example, the amplified nucleic acid samples are end-labeled to form labeled amplified material. For example, amplified nucleic acid molecules can be labeled by including labeled nucleotides in the amplification reactions. In another example, nucleic acid molecules obtained from a subject are labeled, and applied to an array containing oligonucleotides. In a particular example, proteins obtained from a subject are labeled and subsequently analyzed, for example by applying them to an array.

In one example, a biological sample from the subject is assayed for an increase or decrease in expression of liver fibrosis related molecules, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, 3250, 3251, 3252, 3253, 3254, 3255, 3256, 3257, 3258, 3259, 3260, 3261, 3262, 3263, 3264, 3265, 3266, 3267, 3268, 3269, 3270, 3271, 3272, 3273, 3274, 3275, 3276, 3277, 3278, 3279, 3280, 3281, 3282, 3283, 3284, 3285, 3286, 3287, 3288, 3289, 3290, 3291, 3292, 3293, 3294, 3295, 3296, 3297, 3298, 3299, 3300, 3301, 3302, 3303, 3304, 3305, 3306, 3307, 3308, 3309, 3310, 3311, 3312, 3313, 3314, 3315, 3316, 3317, 3318, 3319, 3320, 3321, 3322, 3323, 3324, 3325, 3326, 3327, 3328, 3329, 3330, 3331, 3332, 3333, 3334, 3335, 3336, 3337, 3338, 3339, 3340, 3341, 3342, 3343, 3344, 3345, 3346, 3347, 3348, 3349, 3350, 3351, 3352, 3353, 3354, 3355, 3356, 3357, 3358, 3359, 3360, 3361, 3362, 3363, 3364, 3365, 3366, 3367, 3368, 3369, 3370, 3371, 3372, 3373, 3374, 3375, 3376, 3377, 3378, 3379, 3380, 3381, 3382, 3383, 3384, 3385, 3386, 3387, 3388, 3389, 3390, 3391, 3392, 3393, 3394, 3395, 3396, 3397, 3398, 3399, 3400, 3401, 3402, 3403, 3404, 3405, 3406, 3407, 3408, 3409, 3410, 3411, 3412, 3413, 3414, 3415, 3416, 3417, 3418, 3419, 3420, 3421, 3422, 3423, 3424, 3425, 3426, 3427, 3428, 3429, 3430, 3431, 3432, 3433, 3434, 3435, 3436, 3437, 3438, 3439, 3440, 3441, 3442, 3443, 3444, 3445, 3446, 3447, 3448, 3449, 3450, 3451, 3452, 3453, 3454, 3455, 3456, 3457, 3458, 3459, 3460, 3461, 3462, 3463, 3464, 3465, 3466, 3467, 3468, 3469, 3470, 3471, 3472, 3473, 3474, 3475, 3476, 3477, 3478, 3479, 3480, 3481, 3482, 3483, 3484, 3485, 3486, 3487, 3488, 3489, 3490, 3491, 3492, 3493, 3494, 3495, 3496, 3497, 3498, 3499, 3500, 3501, 3502, 3503, 3504, 3505, 3506, 3507, 3508, 3509, 3510, 3511, 3512, 3513, 3514, 3515, 3516, 3517, 3518, 3519, 3520, 3521, 3522, 3523, 3524, 3525, 3526, 3527, 3528, 3529, 3530, 3531, 3532, 3533, 3534, 3535, 3536, 3537, 3538, 3539, 3540, 3541, 3542, 3543, 3544, 3545, 3546, 3547, 3548, 3549, 3550, 3551, 3552, 3553, 3554, 3555, 3556, 3557, 3558, 3559, 3560, 3561, 3562, 3563, 3564, 3565, 3566, 3567, 3568, 3569, 3570, 3571, 3572, 3573, 3574, 3575, 3576, 3577, 3578, 3579, 3580, 3581, 3582, 3583, 3584, 3585, 3586, 3587, 3588, 3589, 3590, 3591, 3592, 3593, 3594, 3595, 3596, 3597, 3598, 3599, 3600, 3601, 3602, 3603, 3604, 3605, 3606, 3607, 3608, 3609, 3610, 3611, 3612, 3613, 3614, 3615, 3616, 3617, 3618, 3619, 3620, 3621, 3622, 3623, 3624, 3625, 3626, 3627, 3628, 3629, 3630, 3631, 3632, 3633, 3634, 3635, 3636, 3637, 3638, 3639, 3640, 3641, 3642, 3643, 3644, 3645, 3646, 3647, 3648, 3649, 3650, 3651, 3652, 3653, 3654, 3655, 3656, 3657, 3658, 3659, 3660, 3661, 3662, 3663, 3664, 3665, 3666, 3667, 3668, 3669, 3670, 3671, 3672, 3673, 3674, 3675, 3676, 3677, 3678, 3679, 3680, 3681, 3682, 3683, 3684, 3685, 3686, 3687, 3688, 3689, 3690, 3691, 3692, 3693, 3694, 3695, 3696, 3697, 3698, 3699, 3700, 3701, 3702, 3703, 3704, 3705, 3706, 3707, 3708, 3709, 3710, 3711, 3712, 3713, 3714, 3715, 3716, 3717, 3718, 3719, 3720, 3721, 3722, 3723, 3724, 3725, 3726, 3727, 3728, 3729, 3730, 3731, 3732, 3733, 3734, 3735, 3736, 3737, 3738, 3739, 3740, 3741, 3742, 3743, 3744, 3745, 3746, 3747, 3748, 3749, 3750, 3751, 3752, 3753, 3754, 3755, 3756, 3757, 3758, 3759, 3760, 3761, 3762, 3763, 3764, 3765, 3766, 3767, 3768, 3769, 3770, 3771, 3772, 3773, 3774, 3775, 3776, 3777, 3778, 3779, 3780, 3781, 3782, 3783, 3784, 3785, 3786, 3787, 3788, 3789, 3790, 3791, 3792, 3793, 3794, 3795, 3796, 3797, 3798, 3799, 3800, 3801, 3802, 3803, 3804, 3805, 3806, 3807, 3808, 3809, 3810, 3811, 3812, 3813, 3814, 3815, 3816, 3817, 3818, 3819, 3820, 3821, 3822, 3823, 3824, 3825, 3826, 3827, 3828, 3829, 3830, 3831, 3832, 3833, 3834, 3835, 3836, 3837, 3838, 3839, 3840, 3841, 3842, 3843, 3844, 3845, 3846, 3847, 3848, 3849, 3850, 3851, 3852, 3853, 3854, 3855, 3856, 3857, 3858, 3859, 3860, 3861, 3862, 3863, 3864, 3865, 3866, 3867, 3868, 3869, 3870, 3871, 3872, 3873, 3874, 3875, 3876, 3877, 3878, 3879, 3880, 3881, 3882, 3883, 3884, 3885, 3886, 3887, 3888, 3889, 3890, 3891, 3892, 3893, 3894, 3895, 3896, 3897, 3898, 3899, 3900, 3901, 3902, 3903, 3904, 3905, 3906, 3907, 3908, 3909, 3910, 3911, 3912, 3913, 3914, 3915, 3916, 3917, 3918, 3919, 3920, 3921, 3922, 3923, 3924, 3925, 3926, 3927, 3928, 3929, 3930, 3931, 3932, 3933, 3934, 3935, 3936, 3937, 3938, 3939, 3940, 3941, 3942, 3943, 3944, 3945, 3946, 3947, 3948, 3949, 3950, 3951, 3952, 3953, 3954, 3955, 3956, 3957, 3958, 3959, 3960, 3961, 3962, 3963, 3964, 3965, 3966, 3967, 3968, 3969, 3970, 3971, 3972, 3973, 3974, 3975, 3976, 3977, 3978, 3979, 3980, 3981, 3982, 3983, 3984, 3985, 3986, 3987, 3988, 3989, 3990, 3991, 3992, 3993, 3994, 3995, 3996, 3997, 3998, 3999, 4000, 4001, 4002, 4003, 4004, 4005, 4006, 4007, 4008, 4009, 4010, 4011, 4012, 4013, 4014, 4015, 4016, 4017, 4018, 4019, 4020, 4021, 4022, 4023, 4024, 4025, 4026, 4027, 4028, 4029, 4030, 4031, 4032, 4033, 4034, 4035, 4036, 4037, 4038, 4039, 4040, 4041, 4042, 4043, 4044, 4045, 4046, 4047, 4048, 4049, 4050, 4051, 4052, 4053, 4054, 4055, 4056, 4057, 4058, 4059, 4060, 4061, 4062, 4063, 4064, 4065, 4066, 4067, 4068, 4069, 4070, 4071, 4072, 4073, 4074, 4075, 4076, 4077, 4078, 4079, 4080, 4081, 4082, 4083, 4084, 4085, 4086, 4087, 4088, 4089, 4090, 4091, 4092, 4093, 4094, 4095, 4096, 4097, 4098, 4099, 4100, 4101, 4102, 4103, 4104, 4105, 4106, 4107, 4108, 4109, 4110, 4111, 4112, 4113, 4114, 4115, 4116, 4117, 4118, 4119, 4120, 4121, 4122, 4123, 4124, 4125, 4126, 4127, 4128, 4129, 4130, 4131, 4132, 4133, 4134, 4135, 4136, 4137, 4138, 4139, 4140, 4141, 4142, 4143, 4144, 4145, 4146, 4147, 4148, 4149, 4150, 4151, 4152, 4153, 4154, 4155, 4156, 4157, 4158, 4159, 4160, 4161, 4162, 4163, 4164, 4165, 4166, 4167, 4168, 4169, 4170, 4171, 4172, 4173, 4174, 4175, 4176, 4177, 4178, 4179, 4180, 4181, 4182, 4183, 4184, 4185, 4186, 4187, 4188, 4189, 4190, 4191, 4192, 4193, 4194, 4195, 4196, 4197, 4198, 4199, 4200, 4201, 4202, 4203, 4204, 4205, 4206, 4207, 4208, 4209, 4210, 4211, 4212, 4213, 4214, 4215, 4216, 4217, 4218, 4219, 4220, 4221, 4222, 4223, 4224, 4225, 4226, 4227, 4228, 4229, 4230, 4231, 4232, 4233, 4234, 4235, 4236, 4237, 4238, 4239, 4240, 4241, 4242, 4243, 4244, 4245, 4246, 4247, 4248, 4249, 4250, 4251, 4252, 4253, 4254, 4255, 4256, 4257, 4258, 4259, 4260, 4261, 4262, 4263, 4264, 4265, 4266, 4267, 4268, 4269, 4270, 4271, 4272, 4273, 4274, 4275, 4276, 4277, 4278, 4279, 4280, 4281, 4282, 4283, 4284, 4285, 4286, 4287, 4288, 4289, 4290, 4291, 4292, 4293, 4294, 4295, 4296, 4297, 4298, 4299, 4300, 4301, 4302, 4303, 4304, 4305, 4306, 4307, 4308, 4309, 4310, 4311, 4312, 4313, 4314, 4315, 4316, 4317, 4318, 4319, 4320, 4321, 4322, 4323, 4324, 4325, 4326, 4327, 4328, 4329, 4330, 4331, 4332, 4333, 4334, 4335, 4336, 4337, 4338, 4339, 4340, 4341, 4342, 4343, 4344, 4345, 4346, 4347, 4348, 4349, 4350, 4351, 4352, 4353, 4354, 4355, 4356, 4357, 4358, 4359, 4360, 4361, 4362, 4363, 4364, 4365, 4366, 4367, 4368, 4369, 4370, 4371, 4372, 4373, 4374, 4375, 4376, 4377, 4378, 4379, 4380, 4381, 4382, 4383, 4384, 4385, 4386, 4387, 4388, 4389, 4390, 4391, 4392, 4393, 4394, 4395, 4396, 4397, 4398, 4399, 4400, 4401, 4402, 4403, 4404, 4405, 4406, 4407, 4408, 4409, 4410, 4411, 4412, 4413, 4414, 4415, 4416, 4417, 4418, 4419, 4420, 4421, 4422, 4423, 4424, 4425, 4426, 4427, 4428, 4429, 4430, 4431, 4432, 4433, 4434, 4435, 4436, 4437, 4438, 4439, 4440, 4441, 4442, 4443, 4444, 4445, 4446, 4447, 4448, 4449, 4450, 4451, 4452, 4453, 4454, 4455, 4456, 4457, 4458, 4459, 4460, 4461, 4462, 4463, 4464, 4465, 4466, 4467, 4468, 4469, 4470, 4471, 4472, 4473, 4474, 4475, 4476, 4477, 4478, 4479, 4480, 4481, 4482, 4483, 4484, 4485, 4486, 4487, 4488, 4489, 4490, 4491, 4492, 4493, 4494, 4495, 4496, 4497, 4498, 4499, 4500, 4501, 4502, 4503, 4504, 4505, 4506, 4507, 4508, 4509, 4510, 4511, 4512, 4513, 4514, 4515, 4516, 4517, 4518, 4519, 4520, 4521, 4522, 4523, 4524, 4525, 4526, 4527, 4528, 4529, 4530, 4531, 4532, 4533, 4534, 4535, 4536, 4537, 4538, 4539, 4540, 4541, 4542, 4543, 4544, 4545, 4546, 4547, 4548, 4549, 4550, 4551, 4552, 4553, 4554, 4555, 4556, 4557, 4558, 4559, 4560, 4561, 4562, 4563, 4564, 4565, 4566, 4567, 4568, 4569, 4570, 4571, 4572, 4573, 4574, 4575, 4576, 4577, 4578, 4579, 4580, 4581, 4582, 4583, 4584, 4585, 4586, 4587, 4588, 4589, 4590, 4591, 4592, 4593, 4594, 4595, 4596, 4597, 4598, 4599, 4600, 4601, 4602, 4603, 4604, 4605, 4606, 4607, 4608, 4609, 4610, 4611, 4612, 4613, 4614, 4615, 4616, 4617, 4618, 4619, 4620, 4621, 4622, 4623, 4624, 4625, 4626, 4627, 4628, 4629, 4630, 4631, 4632, 4633, 4634, 4635, 4636, 4637, 4638, 4639, 4640, 4641, 4642, 4643, 4644, 4645, 4646, 4647, 4648, 4649, 4650, 4651, 4652, 4653, 4654, 4655, 4656, 4657, 4658, 4659, 4660, 4661, 4662, 4663, 4664, 4665, 4666, 4667, 4668, 4669, 4670, 4671, 4672, 4673, 4674, 4675, 4676, 4677, 4678, 4679, 4680, 4681, 4682, 4683, 4684, 4685, 4686, 4687, 4688, 4689, 4690, 4691, 4692, 4693, 4694, 4695, 4696, 4697, 4698, 4699, 4700, 4701, 4702, 4703, 4704, 4705, 4706, 4707, 4708, 4709, 4710, 4711, 4712, 4713, 4714, 4715, 4716, 4717, 4718, 4719, 4720, 4721, 4722, 4723, 4724, 4725, 4726, 4727, 4728, 4729, 4730, 4731, 4732, 4733, 4734, 4735, 4736, 4737, 4738, 4739, 4740, 4741, 4742, 4743, 4744, 4745, 4746, 4747, 4748, 4749, 4750, 4751, 4752, 4753, 4754, 4755, 4756, 4757, 4758, 4759, 4760, 4761, 4762, 4763, 4764, 4765, 4766, 4767, 4768, 4769, 4770, 4771, 4772, 4773, 4774, 4775, 4776, 4777, 4778, 4779, 4780, 4781, 4782, 4783, 4784, 4785, 4786, 4787, 4788, 4789, 4790, 4791, 4792, 4793, 4794, 4795, 4796, 4797, 4798, 4799, 4800, 4801, 4802, 4803, 4804, 4805, 4806, 4807, 4808, 4809, 4810, 4811, 4812, 4813, 4814, 4815, 4816, 4817, 4818, 4819, 4820, 4821, 4822, 4823, 4824, 4825, 4826, 4827, 4828, 4829, 4830, 4831, 4832, 4833, 4834, 4835, 4836, 4837, 4838, 4839, 4840, 4841, 4842, 4843, 4844, 4845, 4846, 4847, 4848, 4849, 4850, 4851, 4852, 4853, 4854, 4855, 4856, 4857, 4858, 4859, 4860, 4861, 4862, 4863, 4864, 4865, 4866, 4867, 4868, 4869, 4870, 4871, 4872, 4873, 4874, 4875, 4876, 4877, 4878, 4879, 4880, 4881, 4882, 4883, 4884, 4885, 4886, 4887, 4888, 4889, 4890, 4891, 4892, 4893, 4894, 4895, 4896, 4897, 4898, 4899, 4900, 4901, 4902, 4903, 4904, 4905, 4906, 4907, 4908, 4909, 4910, 4911, 4912, 4913, 4914, 4915, 4916, 4917, 4918, 4919, 4920, 4921, 4922, 4923, 4924, 4925, 4926, 4927, 4928, 4929, 4930, 4931, 4932, 4933, 4934, 4935, 4936, 4937, 4938, 4939, 4940, 4941, 4942, 4943, 4944, 4945, 4946, 4947, 4948, 4949, 4950, 4951, 4952, 4953, 4954, 4955, 4956, 4957, 4958, 4959, 4960, 4961, 4962, 4963, 4964, 4965, 4966, 4967, 4968, 4969, 4970, 4971, 4972, 4973, 4974, 4975, 4976, 4977, 4978, 4979, 4980, 4981, 4982, 4983, 4984, 4985, 4986, 4987, 4988, 4989, 4990, 4991, 4992, 4993, 4994, 4995, 4996, 4997, 4998, 4999, 5000, 5001, 5002, 5003, 5004, 5005, 5006, 5007, 5008, 5009, 5010, 5011, 5012, 5013, 5014, 5015, 5016, 5017, 5018, 5019, 5020, 5021, 5022, 5023, 5024, 5025, 5026, 5027, 5028, 5029, 5030, 5031, 5032, 5033, 5034, 5035, 5036, 5037, 5038, 5039, 5040, 5041, 5042, 5043, 5044, 5045, 5046, 5047, 5048, 5049, 5050, 5051, 5052, 5053, 5054, 5055, 5056, 5057, 5058, 5059, 5060, 5061, 5062, 5063, 5064, 5065, 5066, 5067, 5068, 5069, 5070, 5071, 5072, 5073, 5074, 5075, 5076, 5077, 5078, 5079, 5080, 5081, 5082, 5083, 5084, 5085, 5086, 5087, 5088, 5089, 5090, 5091, 5092, 5093, 5094, 5095, 5096, 5097, 5098, 5099, 5100, 5101, 5102, 5103, 5104, 5105, 5106, 5107, 5108, 5109, 5110, 5111, 5112, 5113, 5114, 5115, 5116, 5117, 5118, 5119, 5120, 5121, 5122, 5123, 5124, 5125, 5126, 5127, 5128, 5129, 5130, 5131, 5132, 5133, 5134, 5135, 5136, 5137, 5138, 5139, 5140, 5141, 5142, 5143, 5144, 5145, 5146, 5147, 5148, 5149, 5150, 5151, 5152, 5153, 5154, 5155, 5156, 5157, 5158, 5159, 5160, 5161, 5162, 5163, 5164, 5165, 5166, 5167, 5168, 5169, 5170, 5171, 5172, 5173, 5174, 5175, 5176, 5177, 5178, 5179, 5180, 5181, 5182, 5183, 5184, 5185, 5186, 5187, 5188, 5189, 5190, 5191, 5192, 5193, 5194, 5195, 5196, 5197, 5198, 5199, 5200, 5201, 5202, 5203, 5204, 5205, 5206, 5207, 5208, 5209, 5210, 5211, 5212, 5213, 5214, 5215, 5216, 5217, 5218, 5219, 5220, 5221, 5222, 5223, 5224, 5225, 5226, 5227, 5228, 5229, 5230, 5231, 5232, 5233, 5234, 5235, 5236, 5237, 5238, 5239, 5240, 5241, 5242, 5243, 5244, 5245, 5246, 5247, 5248, 5249, 5250, 5251, 5252, 5253, 5254, 5255, 5256, 5257, 5258, 5259, 5260, 5261, 5262, 5263, 5264, 5265, 5266, 5267, 5268, 5269, 5270, 5271, 5272, 5273, 5274, 5275, 5276, 5277, 5278, 5279, 5280, 5281, 5282, 5283, 5284, 5285, 5286, 5287, 5288, 5289, 5290, 5291, 5292, 5293, 5294, 5295, 5296, 5297, 5298, 5299, 5300, 5301, 5302, 5303, 5304, 5305, 5306, 5307, 5308, 5309, 5310, 5311, 5312, 5313, 5314, 5315, 5316, 5317, 5318, 5319, 5320, 5321, 5322, 5323, 5324, 5325, 5326, 5327, 5328, 5329, 5330, 5331, 5332, 5333, 5334, 5335, 5336, 5337, 5338, 5339, 5340, 5341, 5342, 5343, 5344, 5345, 5346, 5347, 5348, 5349, 5350, 5351, 5352, 5353, 5354, 5355, 5356, 5357, 5358, 5359, 5360, 5361, 5362, 5363, 5364, 5365, 5366, 5367, 5368, 5369, 5370, 5371, 5372, 5373, 5374, 5375, 5376, 5377, 5378, 5379, 5380, 5381, 5382, 5383, 5384, 5385, 5386, 5387, 5388, 5389, 5390, 5391, 5392, 5393, 5394, 5395, 5396, 5397, 5398, 5399, 5400, 5401, 5402, 5403, 5404, 5405, 5406, 5407, 5408, 5409, 5410, 5411, 5412, 5413, 5414, 5415, 5416, 5417, 5418, 5419, 5420, 5421, 5422, 5423, 5424, 5425, 5426, 5427, 5428, 5429, 5430, 5431, 5432, 5433, 5434, 5435, 5436, 5437, 5438, 5439, 5440, 5441, 5442, 5443, 5444, 5445, 5446, 5447, 5448, 5449, 5450, 5451, 5452, 5453, 5454, 5455, 5456, 5457, 5458, 5459, 5460, 5461, 5462, 5463, 5464, 5465, 5466, 5467, 5468, 5469, 5470, 5471, 5472, 5473, 5474, 5475, 5476, 5477, 5478, 5479, 5480, 5481, 5482, 5483, 5484, 5485, 5486, 5487, 5488, 5489, 5490, 5491, 5492, 5493, 5494, 5495, 5496, 5497, 5498, 5499, 5500, 5501, 5502, 5503, 5504, 5505, 5506, 5507, 5508, 5509, 5510, 5511, 5512, 5513, 5514, 5515, 5516, 5517, 5518, 5519, 5520, 5521, 5522, 5523, 5524, 5525, 5526, 5527, 5528, 5529, 5530, 5531, 5532, 5533, 5534, 5535, 5536, 5537, 5538, 5539, 5540, 5541, 5542, 5543, or 5544 of the peptides shown in any of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, 3250, 3251, 3252, 3253, 3254, 3255, 3256, 3257, 3258, 3259, 3260, 3261, 3262, 3263, 3264, 3265, 3266, 3267, 3268, 3269, 3270, 3271, 3272, 3273, 3274, 3275, 3276, 3277, 3278, 3279, 3280, 3281, 3282, 3283, 3284, 3285, 3286, 3287, 3288, 3289, 3290, 3291, 3292, 3293, 3294, 3295, 3296, 3297, 3298, 3299, 3300, 3301, 3302, 3303, 3304, 3305, 3306, 3307, 3308, 3309, 3310, 3311, 3312, 3313, 3314, 3315, 3316, 3317, 3318, 3319, 3320, 3321, 3322, 3323, 3324, 3325, 3326, 3327, 3328, 3329, 3330, 3331, 3332, 3333, 3334, 3335, 3336, 3337, 3338, 3339, 3340, 3341, 3342, 3343, 3344, 3345, 3346, 3347, 3348, 3349, 3350, 3351, 3352, 3353, 3354, 3355, 3356, 3357, 3358, 3359, 3360, 3361, 3362, 3363, 3364, 3365, 3366, 3367, 3368, 3369, 3370, 3371, 3372, 3373, 3374, 3375, 3376, 3377, 3378, 3379, 3380, 3381, 3382, 3383, 3384, 3385, 3386, 3387, 3388, 3389, 3390, 3391, 3392, 3393, 3394, 3395, 3396, 3397, 3398, 3399, 3400, 3401, 3402, 3403, 3404, 3405, 3406, 3407, 3408, 3409, 3410, 3411, 3412, 3413, 3414, 3415, 3416, 3417, 3418, 3419, 3420, 3421, 3422, 3423, 3424, 3425, 3426, 3427, 3428, 3429, 3430, 3431, 3432, 3433, 3434, 3435, 3436, 3437, 3438, 3439, 3440, 3441, 3442, 3443, 3444, 3445, 3446, 3447, 3448, 3449, 3450, 3451, 3452, 3453, 3454, 3455, 3456, 3457, 3458, 3459, 3460, 3461, 3462, 3463, 3464, 3465, 3466, 3467, 3468, 3469, 3470, 3471, 3472, 3473, 3474, 3475, 3476, 3477, 3478, 3479, 3480, 3481, 3482, 3483, 3484, 3485, 3486, 3487, 3488, 3489, 3490, 3491, 3492, 3493, 3494, 3495, 3496, 3497, 3498, 3499, 3500, 3501, 3502, 3503, 3504, 3505, 3506, 3507, 3508, 3509, 3510, 3511, 3512, 3513, 3514, 3515, 3516, 3517, 3518, 3519, 3520, 3521, 3522, 3523, 3524, 3525, 3526, 3527, 3528, 3529, 3530, 3531, 3532, 3533, 3534, 3535, 3536, 3537, 3538, 3539, 3540, 3541, 3542, 3543, 3544, 3545, 3546, 3547, 3548, 3549, 3550, 3551, 3552, 3553, 3554, 3555, 3556, 3557, 3558, 3559, 3560, 3561, 3562, 3563, 3564, 3565, 3566, 3567, 3568, 3569, 3570, 3571, 3572, 3573, 3574, 3575, 3576, 3577, 3578, 3579, 3580, 3581, 3582, 3583, 3584, 3585, 3586, 3587, 3588, 3589, 3590, 3591, 3592, 3593, 3594, 3595, 3596, 3597, 3598, 3599, 3600, 3601, 3602, 3603, 3604, 3605, 3606, 3607, 3608, 3609, 3610, 3611, 3612, 3613, 3614, 3615, 3616, 3617, 3618, 3619, 3620, 3621, 3622, 3623, 3624, 3625, 3626, 3627, 3628, 3629, 3630, 3631, 3632, 3633, 3634, 3635, 3636, 3637, 3638, 3639, 3640, 3641, 3642, 3643, 3644, 3645, 3646, 3647, 3648, 3649, 3650, 3651, 3652, 3653, 3654, 3655, 3656, 3657, 3658, 3659, 3660, 3661, 3662, 3663, 3664, 3665, 3666, 3667, 3668, 3669, 3670, 3671, 3672, 3673, 3674, 3675, 3676, 3677, 3678, 3679, 3680, 3681, 3682, 3683, 3684, 3685, 3686, 3687, 3688, 3689, 3690, 3691, 3692, 3693, 3694, 3695, 3696, 3697, 3698, 3699, 3700, 3701, 3702, 3703, 3704, 3705, 3706, 3707, 3708, 3709, 3710, 3711, 3712, 3713, 3714, 3715, 3716, 3717, 3718, 3719, 3720, 3721, 3722, 3723, 3724, 3725, 3726, 3727, 3728, 3729, 3730, 3731, 3732, 3733, 3734, 3735, 3736, 3737, 3738, 3739, 3740, 3741, 3742, 3743, 3744, 3745, 3746, 3747, 3748, 3749, 3750, 3751, 3752, 3753, 3754, 3755, 3756, 3757, 3758, 3759, 3760, 3761, 3762, 3763, 3764, 3765, 3766, 3767, 3768, 3769, 3770, 3771, 3772, 3773, 3774, 3775, 3776, 3777, 3778, 3779, 3780, 3781, 3782, 3783, 3784, 3785, 3786, 3787, 3788, 3789, 3790, 3791, 3792, 3793, 3794, 3795, 3796, 3797, 3798, 3799, 3800, 3801, 3802, 3803, 3804, 3805, 3806, 3807, 3808, 3809, 3810, 3811, 3812, 3813, 3814, 3815, 3816, 3817, 3818, 3819, 3820, 3821, 3822, 3823, 3824, 3825, 3826, 3827, 3828, 3829, 3830, 3831, 3832, 3833, 3834, 3835, 3836, 3837, 3838, 3839, 3840, 3841, 3842, 3843, 3844, 3845, 3846, 3847, 3848, 3849, 3850, 3851, 3852, 3853, 3854, 3855, 3856, 3857, 3858, 3859, 3860, 3861, 3862, 3863, 3864, 3865, 3866, 3867, 3868, 3869, 3870, 3871, 3872, 3873, 3874, 3875, 3876, 3877, 3878, 3879, 3880, 3881, 3882, 3883, 3884, 3885, 3886, 3887, 3888, 3889, 3890, 3891, 3892, 3893, 3894, 3895, 3896, 3897, 3898, 3899, 3900, 3901, 3902, 3903, 3904, 3905, 3906, 3907, 3908, 3909, 3910, 3911, 3912, 3913, 3914, 3915, 3916, 3917, 3918, 3919, 3920, 3921, 3922, 3923, 3924, 3925, 3926, 3927, 3928, 3929, 3930, 3931, 3932, 3933, 3934, 3935, 3936, 3937, 3938, 3939, 3940, 3941, 3942, 3943, 3944, 3945, 3946, 3947, 3948, 3949, 3950, 3951, 3952, 3953, 3954, 3955, 3956, 3957, 3958, 3959, 3960, 3961, 3962, 3963, 3964, 3965, 3966, 3967, 3968, 3969, 3970, 3971, 3972, 3973, 3974, 3975, 3976, 3977, 3978, 3979, 3980, 3981, 3982, 3983, 3984, 3985, 3986, 3987, 3988, 3989, 3990, 3991, 3992, 3993, 3994, 3995, 3996, 3997, 3998, 3999, 4000, 4001, 4002, 4003, 4004, 4005, 4006, 4007, 4008, 4009, 4010, 4011, 4012, 4013, 4014, 4015, 4016, 4017, 4018, 4019, 4020, 4021, 4022, 4023, 4024, 4025, 4026, 4027, 4028, 4029, 4030, 4031, 4032, 4033, 4034, 4035, 4036, 4037, 4038, 4039, 4040, 4041, 4042, 4043, 4044, 4045, 4046, 4047, 4048, 4049, 4050, 4051, 4052, 4053, 4054, 4055, 4056, 4057, 4058, 4059, 4060, 4061, 4062, 4063, 4064, 4065, 4066, 4067, 4068, 4069, 4070, 4071, 4072, 4073, 4074, 4075, 4076, 4077, 4078, 4079, 4080, 4081, 4082, 4083, 4084, 4085, 4086, 4087, 4088, 4089, 4090, 4091, 4092, 4093, 4094, 4095, 4096, 4097, 4098, 4099, 4100, 4101, 4102, 4103, 4104, 4105, 4106, 4107, 4108, 4109, 4110, 4111, 4112, 4113, 4114, 4115, 4116, 4117, 4118, 4119, 4120, 4121, 4122, 4123, 4124, 4125, 4126, 4127, 4128, 4129, 4130, 4131, 4132, 4133, 4134, 4135, 4136, 4137, 4138, 4139, 4140, 4141, 4142, 4143, 4144, 4145, 4146, 4147, 4148, 4149, 4150, 4151, 4152, 4153, 4154, 4155, 4156, 4157, 4158, 4159, 4160, 4161, 4162, 4163, 4164, 4165, 4166, 4167, 4168, 4169, 4170, 4171, 4172, 4173, 4174, 4175, 4176, 4177, 4178, 4179, 4180, 4181, 4182, 4183, 4184, 4185, 4186, 4187, 4188, 4189, 4190, 4191, 4192, 4193, 4194, 4195, 4196, 4197, 4198, 4199, 4200, 4201, 4202, 4203, 4204, 4205, 4206, 4207, 4208, 4209, 4210, 4211, 4212, 4213, 4214, 4215, 4216, 4217, 4218, 4219, 4220, 4221, 4222, 4223, 4224, 4225, 4226, 4227, 4228, 4229, 4230, 4231, 4232, 4233, 4234, 4235, 4236, 4237, 4238, 4239, 4240, 4241, 4242, 4243, 4244, 4245, 4246, 4247, 4248, 4249, 4250, 4251, 4252, 4253, 4254, 4255, 4256, 4257, 4258, 4259, 4260, 4261, 4262, 4263, 4264, 4265, 4266, 4267, 4268, 4269, 4270, 4271, 4272, 4273, 4274, 4275, 4276, 4277, 4278, 4279, 4280, 4281, 4282, 4283, 4284, 4285, 4286, 4287, 4288, 4289, 4290, 4291, 4292, 4293, 4294, 4295, 4296, 4297, 4298, 4299, 4300, 4301, 4302, 4303, 4304, 4305, 4306, 4307, 4308, 4309, 4310, 4311, 4312, 4313, 4314, 4315, 4316, 4317, 4318, 4319, 4320, 4321, 4322, 4323, 4324, 4325, 4326, 4327, 4328, 4329, 4330, 4331, 4332, 4333, 4334, 4335, 4336, 4337, 4338, 4339, 4340, 4341, 4342, 4343, 4344, 4345, 4346, 4347, 4348, 4349, 4350, 4351, 4352, 4353, 4354, 4355, 4356, 4357, 4358, 4359, 4360, 4361, 4362, 4363, 4364, 4365, 4366, 4367, 4368, 4369, 4370, 4371, 4372, 4373, 4374, 4375, 4376, 4377, 4378, 4379, 4380, 4381, 4382, 4383, 4384, 4385, 4386, 4387, 4388, 4389, 4390, 4391, 4392, 4393, 4394, 4395, 4396, 4397, 4398, 4399, 4400, 4401, 4402, 4403, 4404, 4405, 4406, 4407, 4408, 4409, 4410, 4411, 4412, 4413, 4414, 4415, 4416, 4417, 4418, 4419, 4420, 4421, 4422, 4423, 4424, 4425, 4426, 4427, 4428, 4429, 4430, 4431, 4432, 4433, 4434, 4435, 4436, 4437, 4438, 4439, 4440, 4441, 4442, 4443, 4444, 4445, 4446, 4447, 4448, 4449, 4450, 4451, 4452, 4453, 4454, 4455, 4456, 4457, 4458, 4459, 4460, 4461, 4462, 4463, 4464, 4465, 4466, 4467, 4468, 4469, 4470, 4471, 4472, 4473, 4474, 4475, 4476, 4477, 4478, 4479, 4480, 4481, 4482, 4483, 4484, 4485, 4486, 4487, 4488, 4489, 4490, 4491, 4492, 4493, 4494, 4495, 4496, 4497, 4498, 4499, 4500, 4501, 4502, 4503, 4504, 4505, 4506, 4507, 4508, 4509, 4510, 4511, 4512, 4513, 4514, 4515, 4516, 4517, 4518, 4519, 4520, 4521, 4522, 4523, 4524, 4525, 4526, 4527, 4528, 4529, 4530, 4531, 4532, 4533, 4534, 4535, 4536, 4537, 4538, 4539, 4540, 4541, 4542, 4543, 4544, 4545, 4546, 4547, 4548, 4549, 4550, 4551, 4552, 4553, 4554, 4555, 4556, 4557, 4558, 4559, 4560, 4561, 4562, 4563, 4564, 4565, 4566, 4567, 4568, 4569, 4570, 4571, 4572, 4573, 4574, 4575, 4576, 4577, 4578, 4579, 4580, 4581, 4582, 4583, 4584, 4585, 4586, 4587, 4588, 4589, 4590, 4591, 4592, 4593, 4594, 4595, 4596, 4597, 4598, 4599, 4600, 4601, 4602, 4603, 4604, 4605, 4606, 4607, 4608, 4609, 4610, 4611, 4612, 4613, 4614, 4615, 4616, 4617, 4618, 4619, 4620, 4621, 4622, 4623, 4624, 4625, 4626, 4627, 4628, 4629, 4630, 4631, 4632, 4633, 4634, 4635, 4636, 4637, 4638, 4639, 4640, 4641, 4642, 4643, 4644, 4645, 4646, 4647, 4648, 4649, 4650, 4651, 4652, 4653, 4654, 4655, 4656, 4657, 4658, 4659, 4660, 4661, 4662, 4663, 4664, 4665, 4666, 4667, 4668, 4669, 4670, 4671, 4672, 4673, 4674, 4675, 4676, 4677, 4678, 4679, 4680, 4681, 4682, 4683, 4684, 4685, 4686, 4687, 4688, 4689, 4690, 4691, 4692, 4693, 4694, 4695, 4696, 4697, 4698, 4699, 4700, 4701, 4702, 4703, 4704, 4705, 4706, 4707, 4708, 4709, 4710, 4711, 4712, 4713, 4714, 4715, 4716, 4717, 4718, 4719, 4720, 4721, 4722, 4723, 4724, 4725, 4726, 4727, 4728, 4729, 4730, 4731, 4732, 4733, 4734, 4735, 4736, 4737, 4738, 4739, 4740, 4741, 4742, 4743, 4744, 4745, 4746, 4747, 4748, 4749, 4750, 4751, 4752, 4753, 4754, 4755, 4756, 4757, 4758, 4759, 4760, 4761, 4762, 4763, 4764, 4765, 4766, 4767, 4768, 4769, 4770, 4771, 4772, 4773, 4774, 4775, 4776, 4777, 4778, 4779, 4780, 4781, 4782, 4783, 4784, 4785, 4786, 4787, 4788, 4789, 4790, 4791, 4792, 4793, 4794, 4795, 4796, 4797, 4798, 4799, 4800, 4801, 4802, 4803, 4804, 4805, 4806, 4807, 4808, 4809, 4810, 4811, 4812, 4813, 4814, 4815, 4816, 4817, 4818, 4819, 4820, 4821, 4822, 4823, 4824, 4825, 4826, 4827, 4828, 4829, 4830, 4831, 4832, 4833, 4834, 4835, 4836, 4837, 4838, 4839, 4840, 4841, 4842, 4843, 4844, 4845, 4846, 4847, 4848, 4849, 4850, 4851, 4852, 4853, 4854, 4855, 4856, 4857, 4858, 4859, 4860, 4861, 4862, 4863, 4864, 4865, 4866, 4867, 4868, 4869, 4870, 4871, 4872, 4873, 4874, 4875, 4876, 4877, 4878, 4879, 4880, 4881, 4882, 4883, 4884, 4885, 4886, 4887, 4888, 4889, 4890, 4891, 4892, 4893, 4894, 4895, 4896, 4897, 4898, 4899, 4900, 4901, 4902, 4903, 4904, 4905, 4906, 4907, 4908, 4909, 4910, 4911, 4912, 4913, 4914, 4915, 4916, 4917, 4918, 4919, 4920, 4921, 4922, 4923, 4924, 4925, 4926, 4927, 4928, 4929, 4930, 4931, 4932, 4933, 4934, 4935, 4936, 4937, 4938, 4939, 4940, 4941, 4942, 4943, 4944, 4945, 4946, 4947, 4948, 4949, 4950, 4951, 4952, 4953, 4954, 4955, 4956, 4957, 4958, 4959, 4960, 4961, 4962, 4963, 4964, 4965, 4966, 4967, 4968, 4969, 4970, 4971, 4972, 4973, 4974, 4975, 4976, 4977, 4978, 4979, 4980, 4981, 4982, 4983, 4984, 4985, 4986, 4987, 4988, 4989, 4990, 4991, 4992, 4993, 4994, 4995, 4996, 4997, 4998, 4999, 5000, 5001, 5002, 5003, 5004, 5005, 5006, 5007, 5008, 5009, 5010, 5011, 5012, 5013, 5014, 5015, 5016, 5017, 5018, 5019, 5020, 5021, 5022, 5023, 5024, 5025, 5026, 5027, 5028, 5029, 5030, 5031, 5032, 5033, 5034, 5035, 5036, 5037, 5038, 5039, 5040, 5041, 5042, 5043, 5044, 5045, 5046, 5047, 5048, 5049, 5050, 5051, 5052, 5053, 5054, 5055, 5056, 5057, 5058, 5059, 5060, 5061, 5062, 5063, 5064, 5065, 5066, 5067, 5068, 5069, 5070, 5071, 5072, 5073, 5074, 5075, 5076, 5077, 5078, 5079, 5080, 5081, 5082, 5083, 5084, 5085, 5086, 5087, 5088, 5089, 5090, 5091, 5092, 5093, 5094, 5095, 5096, 5097, 5098, 5099, 5100, 5101, 5102, 5103, 5104, 5105, 5106, 5107, 5108, 5109, 5110, 5111, 5112, 5113, 5114, 5115, 5116, 5117, 5118, 5119, 5120, 5121, 5122, 5123, 5124, 5125, 5126, 5127, 5128, 5129, 5130, 5131, 5132, 5133, 5134, 5135, 5136, 5137, 5138, 5139, 5140, 5141, 5142, 5143, 5144, 5145, 5146, 5147, 5148, 5149, 5150, 5151, 5152, 5153, 5154, 5155, 5156, 5157, 5158, 5159, 5160, 5161, 5162, 5163, 5164, 5165, 5166, 5167, 5168, 5169, 5170, 5171, 5172, 5173, 5174, 5175, 5176, 5177, 5178, 5179, 5180, 5181, 5182, 5183, 5184, 5185, 5186, 5187, 5188, 5189, 5190, 5191, 5192, 5193, 5194, 5195, 5196, 5197, 5198, 5199, 5200, 5201, 5202, 5203, 5204, 5205, 5206, 5207, 5208, 5209, 5210, 5211, 5212, 5213, 5214, 5215, 5216, 5217, 5218, 5219, 5220, 5221, 5222, 5223, 5224, 5225, 5226, 5227, 5228, 5229, 5230, 5231, 5232, 5233, 5234, 5235, 5236, 5237, 5238, 5239, 5240, 5241, 5242, 5243, 5244, 5245, 5246, 5247, 5248, 5249, 5250, 5251, 5252, 5253, 5254, 5255, 5256, 5257, 5258, 5259, 5260, 5261, 5262, 5263, 5264, 5265, 5266, 5267, 5268, 5269, 5270, 5271, 5272, 5273, 5274, 5275, 5276, 5277, 5278, 5279, 5280, 5281, 5282, 5283, 5284, 5285, 5286, 5287, 5288, 5289, 5290, 5291, 5292, 5293, 5294, 5295, 5296, 5297, 5298, 5299, 5300, 5301, 5302, 5303, 5304, 5305, 5306, 5307, 5308, 5309, 5310, 5311, 5312, 5313, 5314, 5315, 5316, 5317, 5318, 5319, 5320, 5321, 5322, 5323, 5324, 5325, 5326, 5327, 5328, 5329, 5330, 5331, 5332, 5333, 5334, 5335, 5336, 5337, 5338, 5339, 5340, 5341, 5342, 5343, 5344, 5345, 5346, 5347, 5348, 5349, 5350, 5351, 5352, 5353, 5354, 5355, 5356, 5357, 5358, 5359, 5360, 5361, 5362, 5363, 5364, 5365, 5366, 5367, 5368, 5369, 5370, 5371, 5372, 5373, 5374, 5375, 5376, 5377, 5378, 5379, 5380, 5381, 5382, 5383, 5384, 5385, 5386, 5387, 5388, 5389, 5390, 5391, 5392, 5393, 5394, 5395, 5396, 5397, 5398, 5399, 5400, 5401, 5402, 5403, 5404, 5405, 5406, 5407, 5408, 5409, 5410, 5411, 5412, 5413, 5414, 5415, 5416, 5417, 5418, 5419, 5420, 5421, 5422, 5423, 5424, 5425, 5426, 5427, 5428, 5429, 5430, 5431, 5432, 5433, 5434, 5435, 5436, 5437, 5438, 5439, 5440, 5441, 5442, 5443, 5444, 5445, 5446, 5447, 5448, 5449, 5450, 5451, 5452, 5453, 5454, 5455, 5456, 5457, 5458, 5459, 5460, 5461, 5462, 5463, 5464, 5465, 5466, 5467, 5468, 5469, 5470, 5471, 5472, 5473, 5474, 5475, 5476, 5477, 5478, 5479, 5480, 5481, 5482, 5483, 5484, 5485, 5486, 5487, 5488, 5489, 5490, 5491, 5492, 5493, 5494, 5495, 5496, 5497, 5498, 5499, 5500, 5501, 5502, 5503, 5504, 5505, 5506, 5507, 5508, 5509, 5510, 5511, 5512, 5513, 5514, 5515, 5516, 5517, 5518, 5519, 5520, 5521, 5522, 5523, 5524, 5525, 5526, 5527, 5528, 5529, 5530, 5531, 5532, 5533, 5534, 5535, 5536, 5537, 5538, 5539, 5540, 5541, 5542, 5543, and 5544.

A. Samples

A biological sample from the subject is assayed for an increase or decrease in expression of liver fibrosis related molecules, such as those listed in any of Tables 1, 2, 3, 5, 6 and 12, as well as any of SEQ ID NOS: 1-5544. Suitable biological samples include those containing DNA or RNA (including cDNA and mRNA) or proteins (including peptide fragments of full-length proteins). Biological samples can be used directly, or filtered, denatured, treated with enzymes, concentrated, diluted, or combinations thereof, before the analysis. In some examples, the sample is depleted of high-abundance proteins.

Exemplary samples include blood or fractions thereof, such as a serum or plasma sample. In some examples, the sample is a liver sample, such as a biopsy or fine needle aspirate sample. In a particular example, the sample is a serum or plasma sample that has been immunodepleted. In another particular example, the sample is a serum or plasma sample without immunodepletion.

B. Nucleic Acid Detection

The detection in the biological sample of increased or decreased expression of a plurality of liver fibrosis related nucleic acids (nucleic acid sequences corresponding to the liver fibrosis related proteins), such as those related to the proteins listed in any of Tables 1, 2, 3, 5, 6 and 12, as well as any of SEQ ID NOS: 1-5544 can be achieved by methods known in the art. For example, increased or decreased expression of a liver fibrosis related protein can be detected by measuring the cellular level of mRNA specific for the liver fibrosis related protein. mRNA can be measured using techniques well known in the art, including for instance Northern analysis, RT-PCR and mRNA in situ hybridization. Details of mRNA analysis procedures can be found, for instance, in provided examples and in Sambrook et al. (ed.), *Molecular Cloning: A Laboratory Manual,* 2nd ed., vol. 1-3, Cold Spring Harbor Laboratory Press, Cold Spring Harbor, N.Y., 1989. In addition, genomic DNA and cDNA can be detected using routine methods.

Oligonucleotides specific to liver fibrosis related nucleic acids can be chemically synthesized using commercially available machines. These oligonucleotides can then be labeled, for example with radioactive isotopes (such as $^{32}$P) or with non-radioactive labels such as biotin (Ward and Langer et al., *Proc. Natl. Acad. Sci. USA* 78:6633-57, 1981) or a fluorophore, and hybridized to individual DNA samples immobilized on membranes or other solid supports by dot-blot or transfer from gels after electrophoresis. These specific sequences are visualized, for example by methods such as autoradiography or fluorometric (Landegren et al., Science 242:229-37, 1989) or colorimetric reactions (Gebeyehu et al., *Nucleic Acids Res.* 15:4513-34, 1987), such as SISH or FISH.

Nucleic acid molecules isolated from samples can be amplified using routine methods to form nucleic acid amplification products (amplicons, for example by contacting the sample with appropriate primers). In some examples, the resulting amplicons are detected during amplification. In other examples, the amplicons are detected following an amplification reaction. For example, amplicons can then be contacted with one or more oligonucleotide probes that will hybridize under stringent conditions with a liver fibrosis related nucleic acid. The nucleic acid amplification products which hybridize with the probe are then detected and quantified. The oligonucleotide probes or primers can bind specifically to a nucleic acid molecule that encodes a protein or peptide listed in any of Tables 1, 2, 3, 5, 6 and 12, as well as any of SEQ ID NOS: 1-5544.

The nucleic acid molecules obtained from the subject that are associated with the liver fibrosis related proteins can be applied to a liver fibrosis detection array under suitable hybridization conditions to form a hybridization complex. For example, the array can include oligonucleotide probes that can hybridize to liver fibrosis related nucleic acid molecules in the sample, such as different oligonucleotide probes on different portions of the array. In particular examples, the nucleic acid molecules in the test sample are labeled, thereby permitting their detection upon hybridization to the oligonucleotide probe on the array. In one example, a pre-treatment solution of organic compounds, solutions that include organic compounds, or hot water, can be applied before hybridization (see U.S. Pat. No. 5,985,567, herein incorporated by reference).

Hybridization conditions for a given combination of array and target material can be optimized routinely in an empirical manner close to the $T_m$ of the expected duplexes, thereby maximizing the discriminating power of the method. Identification of the location in the array, such as a cell, in which binding occurs, permits a rapid and accurate identification of sequences associated with liver fibrosis present in the amplified material (see below).

The hybridization conditions are selected to permit discrimination between matched and mismatched oligonucleotides. Hybridization conditions can be chosen to correspond to those known to be suitable in standard procedures for hybridization to filters and then optimized for use with the arrays of the disclosure. For example, conditions suitable for hybridization of one type of target would be adjusted for the use of other targets for the array. In particular, temperature is controlled to substantially eliminate formation of duplexes between sequences other than exactly complementary liver fibrosis related nucleic acids. A variety of known hybridization solvents can be employed, the choice being dependent on considerations known to one of skill in the art (see U.S. Pat. No. 5,981,185).

Once the liver fibrosis related nucleic acid from the subject have been hybridized with the oligonucleotides present in the liver fibrosis detection array, the presence of the hybridization complex can be analyzed, for example by detecting the complexes.

Detecting a hybridized complex in an array of oligonucleotide probes has been previously described (see U.S. Pat. No. 5,985,567). In one example, detection includes detecting one or more labels present on the oligonucleotides, the sequences obtained from the subject, or both. In particular examples, developing includes applying a buffer. In one example, the buffer is or includes sodium saline citrate, sodium saline phosphate, tetramethylammonium chloride, sodium saline citrate in ethylenediaminetetra-acetic, sodium saline citrate in sodium dodecyl sulfate, sodium saline phosphate in ethylenediaminetetra-acetic, sodium saline phosphate in sodium dodecyl sulfate, tetramethylammonium chloride in ethylenediaminetetra-acetic, tetramethylammonium chloride in sodium dodecyl sulfate, or combinations thereof. However, other suitable buffer solutions can be used.

Detection can further include treating the hybridized complex with a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when fluorophores or radiolabels are used.

In particular examples, the method further includes quantification, for instance by determining the amount of hybridization or amount of amplicons produced following amplification (e.g., using PCR).

C. Protein Detection

Protein expression can be detected using any method known in the art, such as by detecting full-length proteins or portions thereof using antibodies or other specific binding agents such as aptamers or aptazymes, or using other methods such as mass spectrometry. The determination of increased or decreased liver fibrosis related protein levels, in comparison to such expression in a control (such as a subject who does not have liver fibrosis or has non-progressing liver fibrosis), is an alternative or supplemental approach to the direct determination of the expression level of liver fibrosis related nucleic acid sequences by the methods outlined above. The availability of antibodies and aptamers specific to liver fibrosis related protein(s) facilitates the detection and quantification of such protein(s) by one of a number of immunoassay methods that are well known in the art, such as those presented in Harlow and Lane (*Antibodies, A Laboratory Manual*, CSHL, New York, 1988). In addition, if such antibodies are not available, methods of constructing antibodies are routine in the art.

TABLE 7

Exemplary antibodies

| Protein | Source | Catalog Number(s) |
|---|---|---|
| F2 (Prothrombin) | Thermo Fisher Scientific Inc | PA1-74072, PA1-74070, PA1-74127 |
| C4A (Complement 4A) | Thermo Fisher Scientific Inc | PA5-16602, LF-MA0187, LF-MA0188, PA1-27058, PA1-28407 |
| QSOX (Sulfhydryl oxidase 1) | Thermo Fisher Scientific Inc | PA5-21578 |
| ECM1 | Thermo Fisher Scientific Inc | MA5-12004, MA1-19051 |
| LGALS3BP | Biorbyt | orb101823, orb102911 |

Any standard immunoassay format (such as ELISA, Western blot, RIA assay, or lateral flow device) can be used to measure liver fibrosis related protein levels. A comparison to control (e.g., subject who does not have liver fibrosis or who has non-progressing liver fibrosis) and an increase or decrease in liver fibrosis related protein expression levels (such as an increase or decrease in any combination of at least 4, at least 5, at least 6, at least 8, or at least 10 proteins or peptides listed in any of Tables 1, 2, 3, 5, 6 and 12, as well as any of SEQ ID NOS: 1-5544) is indicative of liver fibrosis. Immunohistochemical techniques can also be utilized for protein detection and quantification. For example, a sample can be obtained from a subject, and stained for the presence of a liver fibrosis related protein using the appropriate protein specific binding agents and any standard detection system (such as one that includes a secondary antibody conjugated to horseradish peroxidase). General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying liver fibrosis related proteins, a biological sample of the subject that includes cellular proteins can be used. Quantification of a liver fibrosis related protein can be achieved by immunoassay and the amount compared to levels of the protein found in cells from a subject who does not have liver fibrosis or has non-progressing liver fibrosis.

In one example, a spectrometric method is utilized to detect or quantify an expression level of a target protein (such as those in any of Tables 1, 2, 3, 5, 6 and 12, as well as any of SEQ ID NOS: 1-5544). Exemplary spectrometric methods include mass spectrometry, nuclear magnetic resonance spectrometry, and combinations thereof. In one example, mass spectrometry is used to detect the presence of a target protein (such as those in any of Tables 1-3, 5-6, 12-24) in a biological sample (see for example, Stemmann et al., Cell 107(6):715-26, 2001; Zhukov et al., "From Isolation to Identification: Using Surface Plasmon Resonance-Mass Spectrometry in Proteomics, PharmaGenomics, March/April 2002).

A target protein (such as a liver fibrosis related protein or peptide) also can be detected by mass spectrometry assays coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE) (Kiernan et al., *Anal. Biochem.*, 301: 49-56, 2002; Poutanen et al., *Mass Spectrom.*, 15: 1685-1692, 2001).

Quantitative mass spectroscopic methods, such as SELDI, can be used to analyze protein expression in a sample. In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). An Agilent 6224 TOF Mass Spectrometer, which may be upgraded to a 1.5 meter flight tube providing resolution of 25,000, can be used to detect protein expression. Similar methods are known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption. In one embodiment, mass spectrometry is coupled to ion mobility separation (IMS-MS) and optionally, liquid chromatography, for the detection of protein expression. In an embodiment, a single instrument couples ion mobility separation (IMS-MS) to mass spectrometry for the detection of liver fibrosis related protein expression. In one embodiment, the instrument couples 1-m ion mobility separation (IMS-MS) with a time-of-flight mass spectrometer such as the Agilent 6224 TOF MS which may optionally be upgraded to a 1.5 meter flight tube. In one embodiment, IMS separations that take place on the time scale of tens of milliseconds offer an additional separation stage and a way of reducing the need for extended LC separation times. In an IMS separation, ions subject to an electric field while traveling through a buffer gas separate quickly based on ion shape, e.g. compact species drift faster than those with extended structures [9, 10]. IMS can be coupled between LC and orthogonal acceleration time-of-flight (TOF) MS stages, and by combining the three orthogonal separations into a single LC-IMS-MS instrumentation platform, multidimensional high-resolution nested spectra are produced containing elution times, mass-to-charge ratios (m/z) and IMS drift times for all detectable ions in a sample [11, 12]

In one example, one or more of the liver fibrosis related proteins or peptides listed in any of Tables 1, 2, 3, 5, 6 and 12, as well as any of SEQ ID NOS: 1-5544 are detected using a tandem mass spectrometry technique, for example by spiking one or more stable isotope peptides to be detected (such as one or more of those in Tables 1, 2, 3, 5, 6 and 12, as well as any of SEQ ID NOS: 1-5544) into a test serum or plasma sample and detecting setting parameters for the specific detection and accurate quantification of the desired liver fibrosis related proteins.

Briefly, one version of SELDI uses a chromatographic surface with a chemistry that selectively captures analytes of interest, such as four or more those in any of Tables 1, 2, 3, 5, 6 and 12, as well as any of SEQ ID NOS: 1-5544. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as any of those in Tables 1, 2, 3, 5, 6 and 12, as well as any of SEQ ID NOS: 1-5544) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind a target protein (such as one or more of those in any of Tables 1, 2, 3, 5, 6 and 12, as well as any of SEQ ID NOS: 1-5544). In other examples, the chromatographic surface consists essentially of, or consists of, antibodies that specifically bind a target protein (such as those in any of Tables 1, 2, 3, 5, 6 and 12, as well as any of SEQ ID NOS: 1-5544). In some examples, the chromatographic surface includes antibodies that bind other molecules, such as housekeeping proteins.

In another example, antibodies are immobilized onto the surface using a bacterial Fc binding support. The chromatographic surface is incubated with a sample. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

Alternatively, the amount of a target protein (such as a liver fibrosis related protein) can be determined using fluorescent methods. In one embodiment, the activity of a fibrosis related protein is measured using a substrate which may emit fluorescence when cleaved by the fibrosis related protein. Alternatively, the activity of a fibrosis related protein may be measured using a fluorescent substrate whose fluorescence is quenched when cleaved by the fibrosis related protein.

To provide an example of a fluorescent method, Quantum dots (Qdots®) are useful, for example when using immunohistochemistry, flow cytometry, and plate-based assays, and may therefore be used in conjunction with this disclosure. Qdot® nanocrystals have unique optical properties including an extremely bright signal for sensitivity and quantitation; and high photostability for imaging and analysis. A single excitation source is needed, and a growing range of conjugates makes them useful in a wide range of cell-based applications. Qdot® Bioconjugates are characterized by quantum yields comparable to the brightest traditional dyes available. Additionally, these quantum dot-based fluorophores absorb 10-1000 times more light than traditional dyes. The emission from the underlying Qdot® quantum dots is narrow and symmetric, which means overlap with other colors is minimized, resulting in minimal bleed through into adjacent detection channels and attenuated crosstalk, in spite of the fact that many more colors can be used simultaneously. Standard fluorescence microscopes are an inexpensive tool for detecting Qdot® Bioconjugates. Since Qdot® conjugates are virtually photo-stable, time can be taken with the microscope to find regions of interest and adequately focus on the samples. Qdot® conjugates are useful any time bright photo-stable emission is required and are particularly useful in multicolor applications where only one excitation source/filter is available and minimal crosstalk among the colors is required.

For example, Qdot® Fluorescent IHC can be performed with secondary antibodies, where the detection substrates are streptavidin-conjugated Qdots®. Image analysis can be performed by initially capturing image cubes on a spectral imaging camera (Cambridge Research Instruments, Woburn, Mass.). Excitation can be conducted with a UV (mercury) light source. The image cubes can then analyze. Briefly, image cubes can be retrieved in the application and data can be extracted and reported based on the pixel intensities of Qdots® expected to emit at 605 nm and 655 nm.

As an example, fluorescence can be measured with the multispectral imaging system Nuance™ (Cambridge Research & Instrumentation, Woburn, Mass.). As another example, fluorescence can be measured with the spectral imaging system SpectrView™ (Applied Spectral Imaging, Vista, Calif.). Multispectral imaging is a technique in which spectroscopic information at each pixel of an image is gathered and the resulting data analyzed with spectral image-processing software. For example, the Nuance system can take a series of images at different wavelengths that are electronically and continuously selectable and then utilized with an analysis program designed for handling such data. The Nuance system is able to obtain quantitative information from multiple dyes simultaneously, even when the spectra of the dyes are highly overlapping or when they are co-localized, or occurring at the same point in the sample, provided that the spectral curves are different. Many biological materials autofluorescence, or emit lower-energy light when excited by higher-energy light. This signal can result in lower contrast images and data. High-sensitivity cameras without multispectral imaging capability only increase the autofluorescence signal along with the fluorescence signal. Multispectral imaging can unmix, or separate out, autofluorescence from the sample and, thereby, increase the achievable signal-to-noise ratio.

D. Solid Supports or Substrates

The described techniques for detecting liver fibrosis related molecules, including proteins and nucleic acids, may include a solid support or substrate which is insoluble or can be made insoluble by a subsequent reaction. Numerous and varied solid supports are known to those skilled in the art and include, without limitation, nitrocellulose, the walls of wells of a reaction tray, multi-well plates, test tubes, polystyrene beads, magnetic beads, membranes and microparticles (such as latex particles). Any suitable porous material with sufficient porosity to allow access by detector reagents and a suitable surface affinity to immobilize capture reagents (e.g., lectins or antibodies) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described herein can be in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support.

The surface of a solid support may be activated by chemical processes that cause covalent linkage of an agent (e.g., a capture reagent, such as an antibody) to the support. However, any other suitable method may be used for immobilizing an agent (e.g., a capture reagent) to a solid support including, without limitation, ionic interactions, hydrophobic interactions, covalent interactions and the like. The particular forces that result in immobilization of an agent on a solid phase are not important for the methods and devices described herein.

A solid phase can be chosen for its intrinsic ability to attract and immobilize an agent, such as a capture reagent (such as an antibody or oligonucleotide probe). Alternatively, the solid phase can possess a factor that has the ability to attract and immobilize an agent, such as a capture reagent. The factor can include a charged substance that is oppositely charged with respect to, for example, the capture reagent itself or to a charged substance conjugated to the capture reagent. In another embodiment, a specific binding member may be immobilized upon the solid phase to immobilize its binding partner (e.g., a capture reagent). In this example, therefore, the specific binding member enables the indirect binding of the capture reagent to a solid phase material.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

E. Lateral Flow Devices

The described techniques for detecting liver fibrosis related molecules, including proteins and nucleic acids, may include use of a lateral flow device. A lateral flow device may be an analytical device in the form of a test strip used in lateral flow chromatography, in which a sample fluid, such as one to be tested for the presence of liver fibrosis related molecules (such as four or more of those shown in any of Tables 1, 2, 3, 5, 6 and 12, as well as any of SEQ ID NOS: 1-5544), flows (for example by capillary action) through the strip (which is frequently made of bibulous materials such as paper, nitrocellulose, and cellulose). The test sample and any suspended target molecule(s) can flow along the strip to a detection zone to indicate a presence, absence and/or quantity of the target molecule(s)

Numerous lateral flow analytical devices are known, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,368,876; 7,799,554; EP 0810436; and WO 92/12428; WO 94/01775; WO 95/16207; and WO 97/06439.

Lateral flow devices can in one example be a one-step lateral flow assay in which a sample fluid is placed in a sample or wicking area on a bibulous strip (though, non-bibulous materials can be used, and rendered bibulous by applying a surfactant to the material), and allowed to migrate along the strip until the sample comes into contact with the detection mechanism. In one embodiment, the sample fluid can flow into an area of the lateral flow device housing oligonucleotide probes for the at least two (e.g., at least 3, at least 4, at least 5 or at least 10) liver fibrosis related nucleic acids. In another embodiment, the sample fluid can flow into an area of the lateral flow device housing antibodies specific for the at least two (e.g., at least 3, at least 4, at least 5 or at least 10) liver fibrosis related proteins and, optionally, labeled secondary antibodies specific for the antibodies which bind to the at least two (e.g., at least 3, at least 4, at least 5 or at least 10) liver fibrosis related proteins.

In some examples, the strip includes multiple regions for detecting different target proteins or other molecules in the sample (for example in parallel lines or as other separate portions of the device). For example, the device can include different regions, each containing antibodies or oligonucleotide probes specific for a different liver fibrosis-related proteins or nucleic acids, respectively. For example, the device can include at least 4, at least 10, at least 20, at least 50, or at least 100 different such regions. The test strips can also incorporate control indicators, which provide a signal that the test has adequately been performed, even if a positive signal indicating the presence (or absence) of a target is not achieved.

A lateral flow device can include a sample application area or wicking pad, which is where the fluid or liquid sample is introduced. In one example, the sample may be introduced to the sample application area by external application, as with a dropper or other applicator. In another example, the sample application area may be directly immersed in the sample, such as when a test strip is dipped into a container holding a sample. In yet another example, the sample may be applied, blotted, poured or expressed onto the sample application area.

A lateral flow device can include a reagent or conjugation pad, the region of a lateral flow device where reagents are immobilized, such as antibodies or aptamers for liver fibrosis-related proteins, which may be immobilized to magnetic beads or other materials. A lateral flow device may have more than one conjugation area, for example, a "primary conjugation area," a "secondary conjugation area," and so on. Often different reagents are immobilized in the primary, secondary, or other conjugation areas. Multiple conjugation areas may have any orientation with respect to each other on the lateral flow substrate; for example, a primary conjugation area may be distal or proximal to a secondary (or other) conjugation area and vice versa. Alternatively, a primary conjugation area and a conjugation (or other) area may be oriented perpendicularly to each other such that the two (or more) conjugation areas form a cross or a plus sign or other symbol. For example, Apilux et al. (*Anal. Chem.* 82:1727-32, 2010), Dungchai et al. (*Anal. Chem.* 81:5821-6, 2009), and Dungchai et al. (*Analytica Chemica Acta* 674:227-33, 2010), provide exemplary lateral flow devices with a central sample area and one or more conjugation areas distal to the sample area, which provide independent test zones where independent reactions can occur (e.g., each test zone has a different reagents for detecting a particular liver fibrosis-related molecule, and can further include one or more reaction pads where reactions can take place (for example interspersed between the reagent pads) and an absorption pad, for example that form a "Y", cloverleaf, or spoke-wheel pattern.

A lateral flow device can include one or more reaction pads, such as a membrane, that can be placed to allow desired reactions to occur, and an absorption pad that draws the sample across the conjugation pad(s) and membrane(s) by capillary action and collects it.

F. ELISA Plates

In the most common type of ELISA, the solid phase is coated with a member of the binding pair. Thus, ELISA plates containing a specific binding agent for each of the at least two liver fibrosis related molecules (e.g., at least 3, at least 4, at least 5 or at least 10) to be detected, each in different wells or different sections of the plate, can be used. For example, the solid phase can be coated with antibodies or aptamers specific for the liver fibrosis-related proteins to be detected, each on a different region of the solid phase. For example, ELISA plates can be coated with a specific antibody (or antigen). The microplate may be incubated for a period of time, during which time the antibodies or aptamers adhere to the walls of the microwells up to the fluid fill level. The microwells are then washed leaving a microplate having microwells whose walls are uniformly covered with antibodies or aptamers up to the fluid fill level. Similarly, the solid phase can be coated with oligonucleotides specific for the liver fibrosis-related nucleic acids to be detected, each on a different region of the solid phase.

In some examples, an aliquot of the sample to be examined is incubated with the solid coated solid phase and any liver fibrosis-related molecule that may be present is captured onto the solid phase. After washing to remove residual sample and any interfering materials it may contain, a second binding agent, specific for the liver fibrosis-related molecule and conjugated to label can be added to the solid phase to permit detection of any liver fibrosis-related molecule that bound to the agents immobilized on the solid phase. Alternatively, the liver fibrosis-related molecules in the sample are labeled prior to applying them to the solid phase, thus permitting their detection upon binding.

It will be realized that the above is a general procedure for bioassay and that many variations are known in the art including fluorogenic and luminogenic substrates for ELISA, direct labeling of the second member of the binding pair with a fluorescent or luminescent molecule and nucleic acids or other specific pairing agents instead of antibodies as the binding agent. Samples may be diluted prior to being dispensed into the solid phase or they may be dispensed into deep well microplates, diluted in situ and then the diluted analyte transferred to the functional solid phase.

The most common type of solid phase is a standard sample vessel known as a microplate which can be stored easily and which may be used with a variety of biological specimens. Microplates are available commercially and are made from e.g., polystyrene, PVC, Perspex or Lucite Known microplates comprise 96 wells (also commonly known as "microwells") which are symmetrically arranged in an 8×12 array. Microwells typically have a maximum volume capacity of approximately 350 µl. However, normally only 10-200 µl of fluid is dispensed into a microwell. In some arrangements of the microplate the microwells are arranged in strips of 8 or 12 wells that can be moved and combined in a carrier to give a complete plate having conventional dimensions. One skilled in the art will appreciate that other arrangements of microplates are known.

Positive and negative controls are generally supplied with commercial kits and are used for quality control and to provide a relative cut-off. After reading the processed microplate, the results of the controls are checked against the manufacturer's validated values to ensure that the analysis has operated correctly and then the value is used to distinguish positive from negative specimens and a cut-off value is calculated. Standards are usually provided for quantitative assays and are used to build a standard curve from which the concentration of analyte in a specimen may be interpolated.

It will be recognized that the ELISA procedure as outlined above involves multiple steps including pipetting, incubation, washing, transferring microplates between activities, reading and data analysis. These steps can be automated.

A laboratory can receive a number of sample tubes containing, for example, body fluid from a number of patients. A specified amount of fluid is then removed from the sample and is then dispensed into one or more microwells of a microplate containing the desired specific binding agents (e.g., antibodies, aptamers, oligonucleotide probes). To detect several different proteins, the sample is dispensed into a number of separate microplates or microwells, each coated with a different binding agent. Alternatively, a single microplate can contain a plurality of wells, each coated with the same specific binding agent (or having a few wells as controls), thus permitting analysis of a plurality of different patient samples. Each microplate or microwell can then be processed to detect the presence of a different liver fibrosis-related molecule. To analyze several different liver fibrosis-related molecules a multiplicity of microplates can be used and transfer of aliquots of the same specimen to the different microplates. Similarly, use of microplates with different binding agents in different microwells permits mutiplexing. For example, a single microwell may be used to determine whether a patient has antibodies to one of the at least two (e.g., at least 3, at least 4, at least 5 or at least 10) liver fibrosis related proteins.

Multiplexing enables multiple different tests to be performed simultaneously upon the same patient sample. One approach to multiplexing is to provide a microplate comprising 96 sample wells wherein an array of different capture antibodies is disposed in each sample well. The arrays comprise, for example, 20 nl spots each having a diameter of 350 µm. The spots are arranged with a pitch spacing of, for example, 650 µm. Each spot may correspond with a different capture antibody. Multiplexing enables a greater number of data points and more information per assay to be obtained compared with conventional ELISA techniques wherein each sample plate tests for a single analyte of interest.

VI. Treatment of Liver Fibrosis and Related Conditions

In certain embodiments, a therapy may be provided based on the diagnosis or prognosis of liver fibrosis or pre-fibrosis. Thus, in some examples the disclosed methods include treating a subject who has been diagnosed or prognosed with liver fibrosis. The disclosed therapeutic agents are administered at therapeutically effective amounts.

Treatment, as used herein, refers to any therapeutic intervention that ameliorates a sign or symptom of a pathological condition, such a sign or symptom of liver fibrosis, or interferes with an underlying pathological process implicated in the condition, such as inflammation in the liver, elevation of liver enzyme levels, and/or the formation of fibrotic structures within the liver. Treatment can also induce remission or cure of a condition, such as liver fibrosis. In particular examples, treatment includes preventing a disease, for example by inhibiting the full development of a disease, such as preventing liver fibrosis or preventing development of a disease or disorder that results from a liver fibrosis. Prevention of a disease does not require a total absence of disease. For example, a decrease of at least 20% or at least 50% can be sufficient.

Treatment of liver fibrosis may be directed toward treatment of liver fibrosis itself and/or treating an underlying cause of liver fibrosis. Recent evidence indicates that even advanced fibrosis is reversible. In experimentally induced fibrosis, cessation of liver injury results in fibrosis regression. In humans, spontaneous resolution of liver fibrosis can occur after successful treatment of the underlying disease. In one example, the antifibrotic therapy administered to the subject is liver-specific, well tolerated when administered for prolonged periods of time, and effective in attenuating excessive collagen deposition without affecting normal ECM synthesis. Exemplary therapies that can be administered in therapeutically effective amounts to a subject diagnosed or prognosed with liver fibrosis are shown in Table 8.

TABLE 8

Exemplary anti-fibrotic drugs for the treatment of liver fibrosis

| Agent | Mode of Administration |
| --- | --- |
| Angiotensin inhibitors | iv, oral |
| Colchicine | Iv, oral |
| Corticosteroids | iv, oral |
| Endothelin inhibitors | iv, oral |
| Interferon-alpha | iv, oral |
| Interleukin-10 | iv |
| Pentoxyfylline | iv, oral |
| Phosphatidylcholine | iv, oral |
| PPAR antagonists | iv, oral |
| S-adenosyl methionine | iv, oral |
| Sho-saiko-to | oral |
| TGF-β1 inhibitors | iv, oral |
| Tocopherol | iv, oral |

In one example, an antiinflammatory drug is used to treat or prevent the liver fibrosis. Corticosteroids can be administered to treat hepatic fibrosis in patients with autoimmune hepatitis and acute alcoholic hepatitis.

Inhibition of the accumulation of activated hepatic stellate cells (HSCs) by modulating either their activation and/or proliferation or promoting their apoptosis is another treatment method. Antioxidants such as vitamin E, silymarin, phosphatidylcholine, and S-adenosyl-L-methionine inhibit HSC activation, protect hepatocytes from undergoing apoptosis, and attenuate experimental liver fibrosis. Antioxidants exert beneficial effects in patients with liver fibrosis patients such as those with alcohol-induced liver disease and NASH. Cell-specific delivery to HSCs can be obtained using different carriers (e.g., cyclic peptides coupled to albumin recognizing collagen type VI receptor and/or PDGFR).

In one example, treatment or prevention of liver fibrosis includes administration of an agent that disrupts TGF-β synthesis and/or signaling pathways. In one example, treatment of prevention of liver fibrosis includes administration of a growth factor (e.g., IGF, hepatocyte growth factor, and cardiotrophin) to attenuate liver fibrosis. Substances that inhibit key signal transduction pathways involved in liver fibrogenesis, such as aspentoxifylline (phosphodiesterase inhibitor), amiloride ($Na^+/H^+$ pump inhibitor), and S-farnesylthiosalicylic acid (Ras antagonist), can be used. In addition, ligands of PPARα and/or PPARγ such as thiazolindiones can be used to treat liver fibrosis.

In one example, inhibition of the renin-angiotensin system is used to treat liver fibrosis.

The blockade of endothelin-1 type A receptors and the administration of vasodilators (prostaglandin E2 and nitric oxide donors) exert antifibrotic activity. Different herbal compounds, such as Sho-saiko-to, glycyrrhizin, and savia miltiorhiza, have antifibrotic effects. Another approach is the inhibition of collagen production and/or the promotion of its degradation. For example, inhibitors of prolyl-4 hydroxylase and halofuginone can prevent the development of cirrhosis by inhibiting collagen synthesis. MMP-8 and urokinase-type plasminogen activator can also stimulate collagen degradation. In one example, infusion of mesenchymal stem cells ameliorates fibrosis.

Antifibrotic therapy may differ depending on the type of liver disease. In patients with chronic HCV infection, antiviral treatments (e.g., pegylated IFN plus ribavirin) can improve liver fibrosis. Renin-angiotensin system inhibitors can be used for the treatment of liver fibrosis in patients with chronic HCV infection. In some examples, treatment of metabolic syndrome in patients with chronic hepatitis C may also decrease fibrosis progression. In patients with alcohol-induced liver disease, alcohol abstinence may be prescribed for prevention/treatment of liver fibrosis. Antioxidants (e.g., S-adenosyl-L-methionine and phosphatidylcholine) and hepatocyte protectors (e.g., silymarin) slow down the progression of liver fibrosis and can improve survival. In some examples, for example in patients with autoimmune hepatitis, immunosuppressant therapy exerts antifibrotic effects. Ursodeoxycholic acid can be administered to treat or prevent liver fibrosis. In patients with NASH, weight loss and specific treatments of the metabolic syndrome can reduce fibrosis development. Antioxidants and insulin sensitizers (e.g., thiazolindiones) can be used to exert antifibrogenic effects. Use of pluripotential stem cells in hepatic wound healing can be an effective treatment for liver fibrosis.

Autoimmune hepatitis may be treated with immunosuppressive glucocorticoids with or without azathioprine and thus prevent liver fibrosis development in these patients.

Budesonide can induce remission of autoimmune hepatitis with fewer adverse effects than, for example, prednisone. Subjects who do not respond to glucocorticoids and azathioprine may be given other immunosuppressives such as mycophenolate, cyclosporin, tacrolimus and methotrexate.

Kits

The present disclosure provides for kits that include reagents that can be used to diagnose or prognose liver fibrosis, for example to determine if a subject has liver fibrosis or has an increased predisposition to developing liver fibrosis. Such kits allow one to determine if a subject has a differential expression in four or more liver fibrosis related molecules, such as any of those listed in Tables 1, 2, 3, 5, 6 and 12, as well as any of SEQ ID NOS: 1-5544. In some examples, the kit includes a lateral flow device or ELISA plate containing binding agents specific for at least two (e.g., at least 3, at least 4, at least 5 or at least 10) different liver fibrosis-related molecules, such as antibodies, aptamers, or oligonucleotide probes.

In one example the disclosed kits include binding molecules such as oligonucleotide probes, oligonucleotide primers, antibodies, aptamers or aptazymes (or combinations thereof) that selectively hybridize or bind to liver fibrosis-related molecules that are the target of the kit. Such oligonucleotide probes, oligonucleotide primers, antibodies, aptamers or aptazymes can include a detectable label, such as a fluorophore. In addition, the oligonucleotide probes, oligonucleotide primers, antibodies, aptamers or aptazymes can be in separate vials or containers. In some examples, the oligonucleotide probes, oligonucleotide primers, antibodies, aptamers or aptazymes are part of a solid substrate, such as a lateral flow device or ELISA plate.

In one embodiment, the disclosed kits include oligonucleotide probes or primers (such as a pair of primers that permits amplification of a target liver fibrosis related nucleic acid) that can hybridize to at least two (e.g., at least 3, at least 4, at least 5 or at least 10) different liver fibrosis related nucleic acid molecules (such as mRNA or cDNA) under high stringency. In some examples such probes or primers are at least 10 nucleotides in length, such as at least 12, at least 15, at least 20, at least 30, or at least 50 nucleotides in length. In some examples, the kit includes both oligonucleotide primers for amplifying at least two (e.g., at least 3, at least 4, at least 5 or at least 10) different liver fibrosis related nucleic acid molecules, and corresponding oligonucleotide probes to detect the resulting amplicons. The disclosed kits may further include a substrate to which the oligonucleotide probes are attached.

In one embodiment, the disclosed kits include antibodies (or aptamers or aptazymes) that can specifically bind to at least two (e.g., at least 3, at least 4, at least 5 or at least 10) different liver fibrosis-related proteins. Such kits may additionally include labeled secondary antibodies specific for the primary antibodies which bind to one or more of the at least two (e.g., at least 3, at least 4, at least 5 or at least 10) liver fibrosis related proteins. The disclosed kits may further include a substrate to which the antibodies are attached.

In particular examples, the oligonucleotide probes or antibodies are attached to an array, such as a biochip, lateral flow device, or dipstick. Such an array can include other oligonucleotides or antibodies, for example to serve as negative or positive controls. In one example, the kit includes oligonucleotide probes or primers (or antibodies) that recognize any combination of at least two of the proteins or peptides in any of Tables 1, 2, 3, 5, 6 and 12, as well as any of SEQ ID NOS: 1-5544, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, or all 136 of the liver fibrosis related proteins listed in Tables 1. In various examples, the kit includes oligonucleotide probes or primers (or antibodies) that recognize at least two (e.g., at least 3, at least 4, at least 5 or at least 10) proteins or peptides listed in one of Table 2, Table 3, Table 5, or any of SEQ ID NOS: 1-5544.

In another example, the kit includes one or more of:

1) at least two stable isotope labeled liver fibrosis proteins listed in Table 1, such as at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 31, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, or all 136 of the stable isotope labeled liver fibrosis related proteins listed in Table 1. In one example, the kit includes at least two (e.g., at least 3, at least 4, at least 5 or at least 10) stable isotope labeled liver fibrosis proteins listed in one of Tables 2, 3, and 5, as well as any of SEQ ID NOS: 1-5544;

2) a suitable HPLC column; and 3) materials for quantifying these peptides using, for example, IMS-MS (see Examples).

Such a kit can be used to detect the at least two (e.g., at least 3, at least 4, at least 5 or at least 10) liver fibrosis related peptides, for example by spiking stable isotope peptides into a test serum or plasma sample and detecting setting parameters for their specific detection and accurate quantification by, for example, using IMS-MS, MRM mass spectrometry or tandem mass spectrometry. The kit can further include one or more of a buffer solution, a conjugating solution for developing the signal of interest, or a detection reagent for detecting the signal of interest, each in separate packaging, such as a container. Kits can include instructions, for instance instructions that provide calibration curves or charts to compare with the determined (such as experimentally measured) values. For example, instructions can permit the tester to determine whether liver fibrosis related protein/peptide expression levels are elevated, reduced, or unchanged in comparison to a control sample. In some examples kits include materials for obtaining a sample, such as vials, cotton swabs, and needles.

In one example, the kits can include a lateral flow device containing antibodies specific for at least two (e.g., at least 3, at least 4, at least 5 or at least 10) different liver fibrosis related-peptides and a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain, for example, one or more biological samples to be tested, positive and/or negative control samples or solutions (such as, a positive control sample containing the target agent), diluents (such as, phosphate buffers, or saline buffers), and/or wash solutions (such as Tris buffers, saline buffer, or distilled water).

Such kits can include other components, such as a buffer, a chart for correlating detected liver fibrosis related protein or nucleic acid level and amount of liver fibrosis related molecule present, or combinations thereof.

Other kit embodiments include syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain implements useful for introducing samples onto a lateral flow device, including, for example, droppers, Dispo-pipettes, capillary tubes, rubber bulbs (e.g., for capillary tubes), and the like. Still other kit embodiments may include disposal means for discarding a used device and/or other items used with the device (such as patient samples, etc.). Such disposal means can include, without limitation, containers that are capable of containing leakage from discarded materials, such as plastic, metal or other impermeable bags, boxes or containers.

In some examples, a kit will include instructions for the use of materials contained therein. The instructions may provide direction on how to apply sample to the components of the kit, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify liver fibrosis related molecules.

A kit may further comprise an alarm which indicates the presence of liver fibrosis, wherein the alarm is activated if the at least two (e.g., at least 3, at least 4, at least 5 or at least 10) proteins are detected with elevated amounts relative to control levels such as control levels for a subject without liver fibrosis. In various embodiments, the alarm is activated if at least 70%, 75%, 80%, 85%, 90%, 95% or 100% of the at least two (e.g., at least 3, at least 4, at least 5 or at least 10) proteins have levels of expression that are elevated relative to control levels such as control levels for a subject without liver fibrosis. A kit may further comprise an interface which may be configured to accept input of a criterion for diagnosis or prognosis of liver fibrosis. For example, a user may select the proteins for which differential expression is detected and/or used to determine whether a subject has liver fibrosis. A user can also use the interface to provide criterion for a clinical judgment such as to select what percentage of the at least two (e.g., at least 3, at least 4, at least 5 or at least 10) proteins must have differential expression to allow for a diagnosis or prognosis of liver fibrosis. In one embodiment, the alarm is a visual alarm which may be a written or digital display such as a number, word, symbolic indicator (e.g., +/−, Y, N), or combinations thereof. In an embodiment, the visual or other alarm is integrated into the interface.

EXAMPLES

Example 1

Methods and Materials

This example provides technical details and procedures, including relevant instrument settings and materials, used to obtain the protein expression data from transplant and non-transplant patients discussed in the Examples below.
Identification of Liver Fibrosis-Related Proteins in Liver Transplant Subjects Liver transplant subjects were categorized as slow-, fast- and non-progressors depending on the rate of fibrosis in the new liver. Each slow and fast progressor had a matched non-progressor subject. Specimen samples were matched for the most important clinical variables known to influence the risk of fibrosis progression associated with recurrent hepatitis C after liver transplantation: donor age and cold ischemia time. These pairs were also matched based on patient sex and age. Matching was also performed to time to biopsy so that there were not discordant times to assessment of the degree of fibrosis, as well as days post-transplant. Patients were excluded from consideration with any known confounders including biliary problems, recurrent CMV infection, and more than one episode of rejection. Although there were minor variations in the doses of immunosuppression each patient received, each patient was part of the same immunosuppression protocol, which included induction therapy, followed by tacrolimus and mycophenelate, with gradual transition to tacrolimus monotherapy after 12 months. No patient received more than one bolus of corticosteroids for treatment of rejection and no patient received monoclonal antibodies (such as OKT3 or ATG) for treatment of rejection.

Comparisons were performed across all slow progressors and fast progressors compared to all their matched controls.

Figure 4A:
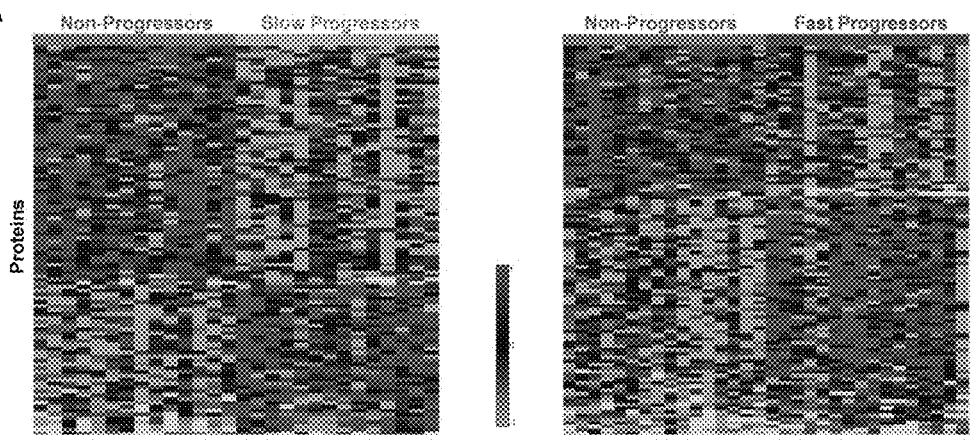
FIG. 4A provides heat maps illustrating the relative log 2 intensity change for proteins with significant differential expression showing up in at least 21 datasets by peptides when non-progressors are compared to either slow progressors (left) or fast progressors (right). Each column represents one of the 60 patients and each row one of the 136 proteins shown in Table 1. Trends between the patient groups are clearly observed, but biodiversity in the human population is also discerned.

Identification and quantification of the detected peptide peaks was performed utilizing the Accurate Mass and Time (AMT) Tag approach (Zimmer et al., *Mass Spectrometry Reviews*, 2006. 25(3):450-482). Briefly, multiple in-house developed/publicly available informatics tools were used to process LC-MS data and correlate the resulting LC-MS features to an AMT tag database containing accurate mass and LC separation elution time information for peptide tags generated from tandem MS Thermo LTQ Orbitrap Velos analyses of human plasma proteins. The AMT tag database only contained peptides which passed a MS-GF cutoff of $1 \times 10^{-9}$ (Sangtae, et al., *J. Proteome Res.*, 7 (8), 3354-3363, 2008). Among the tools used were algorithms for peak-picking and for determining isotopic distributions and charge states (Jaitly et al., *BMC Bioinformatics*, 2009. 10(1):87). Further downstream data analysis incorporated all of the possible detected peptides into a visualization program VIPER (Monroe, *Bioinformatics*, 2007. 23(15):2021-3) to correlate LC-MS features to the peptide identifications in the AMT tag database. The Viper results were matched and refined to give a median mass tolerance of ±2.05 ppm and a median normalized elution tolerance (NET) of ±0.75%. VIPER provided an intensity report for all detected features, normalized LC elution times via alignment to the database, and feature identification. A representative protein was chosen for redundant peptides (see SEQ ID NOS: 1-2633). If a protein was identified with only one significant non-unique peptide it was removed. In DAnTE software, peptide peak intensity values were converted to a log 2 scale statistically compared utilizing ANOVA (performed as a t-test with only two data types in each comparisons) (Polpitiya et al., *Bioinformatics*, 2008. 24(13):1556-8). The analysis only focused on significantly changing peptides (p-values and q-values<0.05). The q-value of a test measures the proportion of false positives incurred (called the false discovery rate) when that particular test is called significant. Significantly changing peptides were assessed at a protein level using DAnTE's Rollup parameters (reference peptide based scaling, where peptides were excluded from scaling if they were not seen in at least 3 datasets and no minimum peptide presence was required). Statistically comparisons were also done at the protein level. Only significantly changing proteins were retained, i.e. some peptides were significant but they were in opposing directions, so the proteins were not significant when the peptides were rolled up (these opposing peptides have grey colored cells in the peptide tables). The three instrument analyses for each same sample were averaged together to create the heatmaps depicted in FIGS. 4A and 4B. FIG. 4A contains all proteins that had at least 21 datapoints and 2 peptides. All 136 significantly changing proteins identified by at least two peptides are listed in Table 1 where 34 proteins increased in the slow progressors (SP) and fast progressors (FP) compared to their matched controls, 37 proteins decreased in the SP and FP compared to their matched controls, 5 proteins only increased in the SP compared to their matched controls, 30 proteins only increased in the FP, 19 proteins only decreased in the SP, 5 proteins only decreased in the FP and 6 proteins increased in the FP and decreased in the SP.

A summary is provided in Table 4 above.

Identification of Liver Fibrosis-Related Proteins in Non-Transplant Subjects

In this study liver transplant patients were categorized by fibrosis level.

Identification and quantification of the detected peptide peaks was performed utilizing the Accurate Mass and Time (AMT) Tag approach (Zimmer et al., Mass Spectrometry Reviews, 2006. 25(3):450-482). Briefly, multiple in-house developed/publicly available informatics tools were used to process LC-MS data and correlate the resulting LC-MS features to an AMT tag database containing accurate mass and LC separation elution time information for peptide tags generated from tandem MS Thermo LTQ Orbitrap Velos analyses of human plasma proteins. The AMT tag database only contained peptides which passed a MS-GF cutoff of $1 \times 10^{-9}$ (Sangtae, et al., J. Proteome Res., 7 (8), 3354-3363, 2008). Among the tools used were algorithms for peak-picking and for determining isotopic distributions and charge states (Jaitly et al., BMC Bioinformatics, 2009. 10(1):87). Further downstream data analysis incorporated all of the possible detected peptides into a visualization program VIPER (Monroe, Bioinformatics, 2007. 23(15):2021-3) to correlate LC-MS features to the peptide identifications in the AMT tag database.

Detected peptides are shown in SEQ ID NOS: 2634-5544. Significant proteins had to have 2 unique peptides to be used for rollup, 78 proteins passed the criteria (these values were used to create the heatmap in FIG. 5). Table 12 contains the 78 significantly changing proteins and denotes if they were also observed to be differentially expressed in the transplant model data.

Sample Preparation for Liver Fibrosis Samples

Human Serum Samples.

Initial blood serum samples were chosen from 60 HCV+ patients following liver transplantation. Additional 60 non-transplant blood serum samples were obtained from HCV+ patients through the Alaska Native Tribal Health Consortium (ANTHC). Non-transplant ANTHC samples were selected based upon biopsy phase (non-fibrosis, 0-1 Ishak score, versus extensive fibrosis/bridging, 4-6 Ishak score), and availability and condition of serum specimen (non-thawed specimen within 6 months of a diagnostic biopsy). All subjects were recruited and samples were collected under institutional review board-approved protocols.

Serum Depletion and Protein Digestion.

Individual human serum samples were partitioned and depleted of 14 highly abundant proteins using a ProteomeLab™ 12.7×79.0-mm IgY14 LC10 affinity LC column (Beckman Coulter, Fullerton, Calif.). The unbound, flow-through fraction containing low- and medium-abundance proteins was collected, directly concentrated in urea buffer (8M urea, 10 mM Tris-HCl, pH 7.4, 150 mM NaCl) by filter centrifugation, then denatured for 1 hour at 37° C. All processing steps following depletion were carried out in a 96-well plate to minimize batch effects associated with processing, utilizing automated protocols on a Biomek FX liquid handling robot (Beckman Coulter). 100 µL aliquots of depleted, concentrated plasma were taken for digestion, giving a starting amount of approximately 100 µg total protein. Aliquots were transferred to a 96-well plate pre-loaded with urea to give a concentration of 8M. Dithiothreitol (DTT) was then added to a final concentration of 10 µM. Samples were incubated for 1 h at 37° C. to denature and reduce. Samples were then diluted 5-fold with 50 mM ammonium bicarbonate prior to the addition of sequence grade trypsin (Promega) in a 1:50 enzyme to protein ratio. Enzymatic digestion was carried out for 6 h at 37° C. Peptides were desalted using an automated protocol utilizing C18 SPEC tips (Varian). Peptides were eluted in 200 µl 80% ACN/0.1% TFA and lyophilized. Desalted peptides were rehydrated in 25 mM Ammonium bicarbonate and concentrations were determined by BCA assay. Final peptide concentrations were normalized to a final concentration of 0.3 µg/µL prior to storage at −80° C. until LC-MS analysis.

Sample Preparation for Spiked Serum Sample

Eight non-plasma peptides (Table 9) from Sigma-Aldrich were used without further purification. A final concentration of 0.25 mg/mL was desired for the tryptically-digested human serum sample to avoid undesirable clogging effects. The serum sample was diluted to 1 mg/mL with water and the 8 non-plasma peptides were added to specific final concentrations from 100 pg/mL to 100 ng/mL (noted in Table 9). An additional standard sample consisting of the eight peptides spiked into water at the same concentrations as in the serum sample was prepared to determine the elution times of the spiked peptides and to compare the dynamic range of detection with the serum sample.

TABLE 9

Non-serum peptides spiked into human serum

| Spiking Level | Peptide |
|---|---|
| 100 pg/mL | Melittin, Dynorphin A Porcine Fragment 1-13 |
| 1 ng/mL | Des Pro Ala Bradykinin, Leucine Enkephalin |
| 10 ng/mL | 3X FLAG Peptide, Substance P |
| 100 ng/mL | Methionine Enkephalin, [D-Ala2]-Deltorphin II |

Instrumental Analysis

Analysis of the 120human serum samples was performed on an in-house built instrument that couples a 1-m ion mobility separation (IMS-MS) with an Agilent 6224 TOF MS upgraded to a 1.5 meter flight tube providing resolution of 25,000 [42]. The analysis of the spiked peptide samples and a small subset of the human serum samples was performed on both a Thermo Fisher Scientific LTQ Orbitrap Velos MS (Velos) (San Jose, Calif., USA) operated in tandem MS (MS/MS) mode and the in-house built IMS-MS instrument. A fully automated in-house built 4-column HPLC system equipped with in-house packed capillary columns was used for both instruments with mobile phase A consisting of 0.1% formic acid in water and phase B comprised of 0.1% formic acid in acetonitrile [43]. A 100-min LC gradient was performed on the Velos MS (using 60 cm long columns with an o.d. of 360 µm, i.d. of 75 µm, and 3-µm C18 packing material), while only a 60-min gradient with shorter columns (30 cm long with same dimensions and packing) was used with the IMS-MS. Both gradients linearly increased mobile phase B from 0 to 60% until the final 2-min of the run when B was purged at 95%. 5 µL of each sample was injected for both analyses and the HPLC was operated under a constant flow rate of 0.4 µL/min for the 100-min gradient and 1 µL/min for the 60-min gradient. The Velos MS data were collected from 400-2000 m/z at a resolution of 60,000 (automatic gain control (AGC) target: $1\times10^6$) followed by data dependent ion trap MS/MS spectra (AGC target: $1\times10^4$) of the ten most abundant ions using a collision energy setting of 35%. A dynamic exclusion time of 60 sec was used to discriminate against previously analyzed ions. IMS-MS data were collected from 100-3200 m/z.

Informatics Approach and Statistical Analysis

Identification and quantification of the detected peptide peaks were performed utilizing the Accurate Mass and Time (AMT) tag approach (Zimmer et al., *Mass Spectrom Rev*, 2006. 25(3):450-82). Briefly, Velos MS/MS data were searched by SEQUEST (Thermo Scientific), and the resulting 13,448 peptides which had a MS-GF score greater than or equal to 1E-9 were used to populate an AMT tag database (Eng et al., *J. Am. Soc. Mass Spec.*, 1994. 5(11):976-989; Kim et al., *J Proteome Res*, 2008. 7(8):3354-63). Multiple in-house developed informatics tools (publicly available ncrr.pnnl.gov/software) were used to process the LC-MS data and correlate the resulting LC-MS features to this AMT tag database that contained accurate mass and LC separation elution time information for peptide tags generated from serum proteins. Among the tools used were algorithms for peak-picking and for determining isotopic distributions and charge states (Jaitly et al., *BMC Bioinformatics*, 2009. 10(1):87). Further downstream data analysis incorporated all possible detected peptides into a visualization program, VIPER, to correlate LC-MS features to the peptide identifications in the AMT tag database (Monroe et al., *Bioinformatics*, 2007. 23(15):2021-3). VIPER provided an intensity report for all detected features, normalized LC elution times via alignment to the database, and featured identification.

For the initial transplant data, a representative protein was chosen for redundant peptides. If a protein was identified with only one significant non-unique peptide it was removed. In DAnTE software, peptide peak intensity values were converted to a log 2 scale statistically compared utilizing ANOVA (performed as a t-test with only two data types in each comparison) (Polpitiya et al., *Bioinformatics*, 2008. 24(13):1556-8). The analysis only focused on significantly changing peptides (p-values and q-values<0.05). The q-value of a test measures the proportion of false positives incurred (called the false discovery rate) when that particular test is called significant. Significantly changing peptides were assessed at a protein level using DAnTE's Rollup parameters (reference peptide based scaling, where peptides were excluded from scaling if they were not seen in at least 3 datasets and no minimum peptide presence was required). Statistically comparisons were also done at the protein level. Only significantly changing proteins were retained (some peptides were significant but they were in opposing directions, so the proteins were not significant when the peptides were rolled up). Final significant proteins identified required at least two significant peptide identifications.

Figure 7:
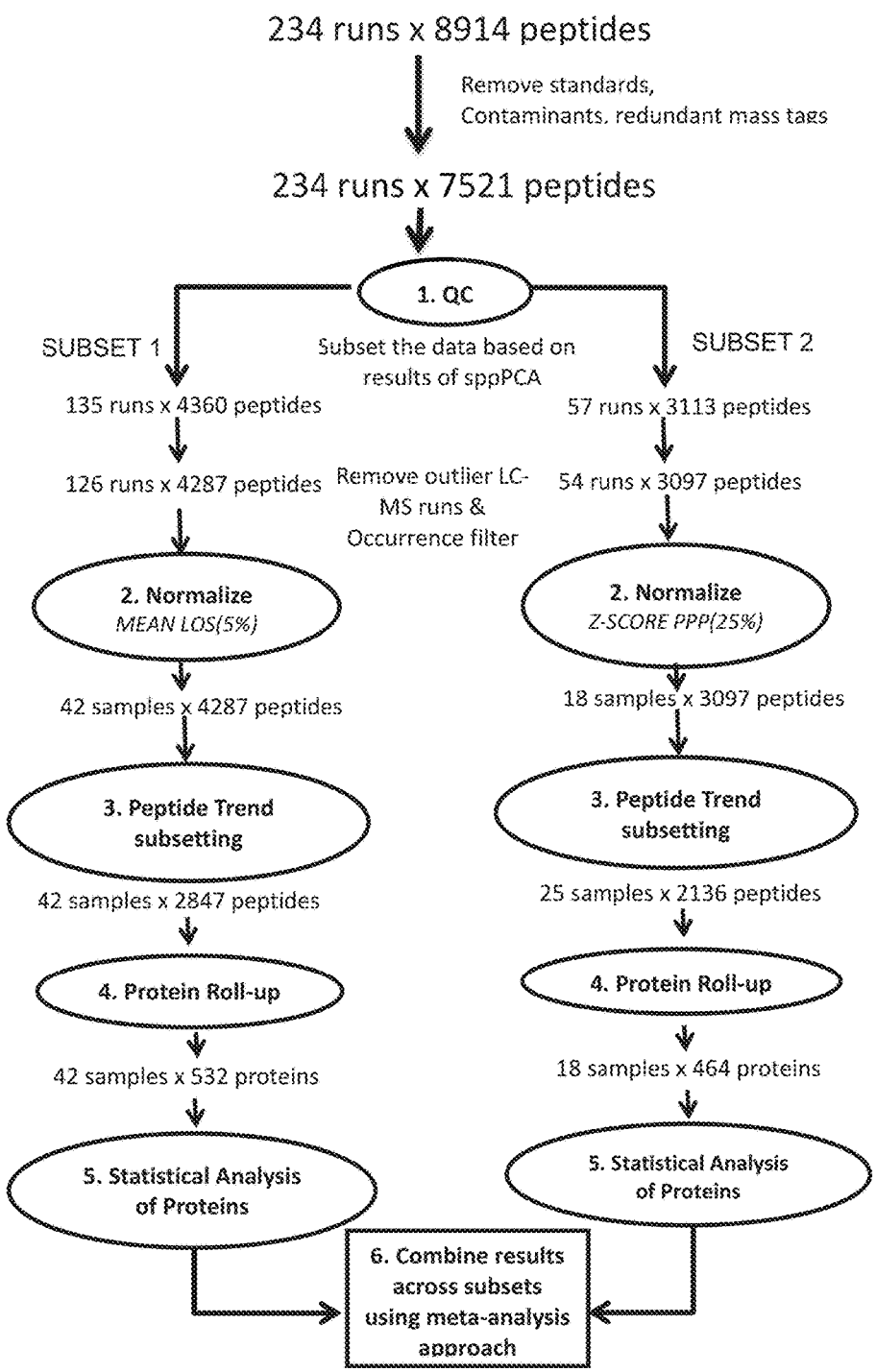
FIG. 7 is a schematic drawing showing the statistical processing pipeline for the verification non-transplant generated data.
Figure 8:
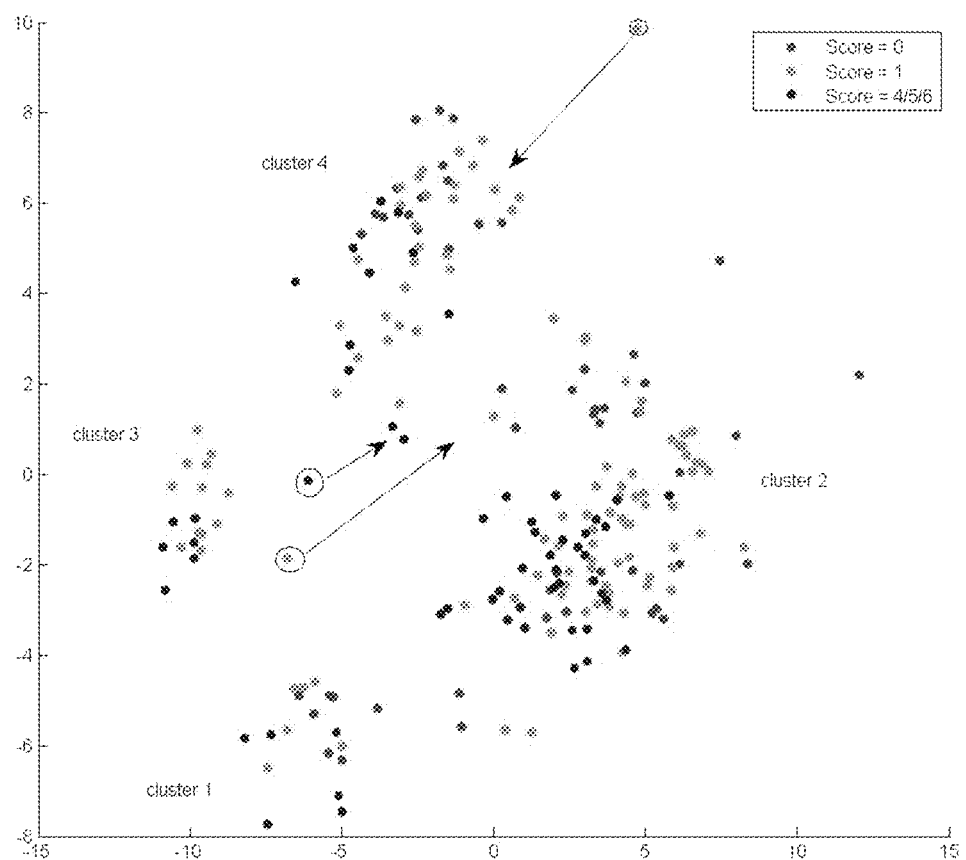
FIG. 8 is a scores plot of the raw peptide abundance values. A sppPCA analysis results in four distinct clusters of data based upon sample preparation and instrument analysis batching. Clusters 4 and 2 were used for further statistical analysis.
Figure 9A:
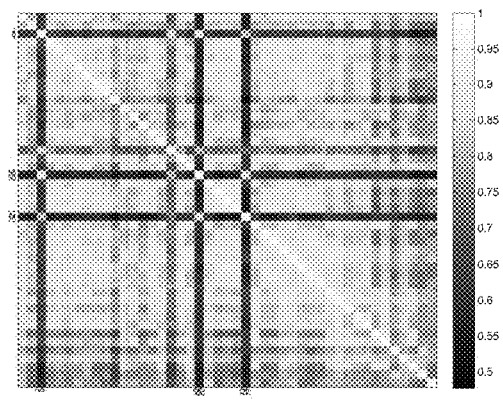
FIG. 9A shows quality control processing. The correlation coefficient of $\log_{10}$ peptide abundance values across LC-MS analyses
Figure 9B:
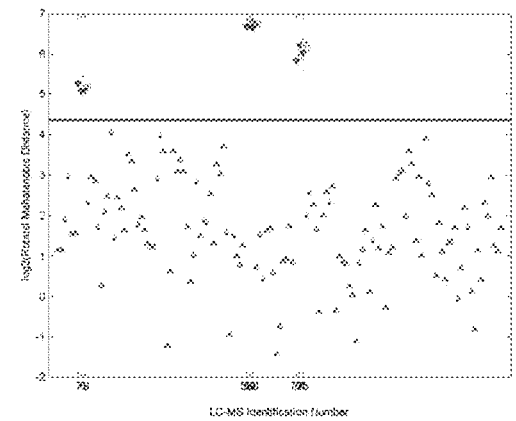
FIG. 9B shows quality control processing. The statistical analysis of the log 2 robust Mahalanobis distances (rMd) to determine if an LC-MS run should be removed from the dataset. The red horizontal line represents a critical value associated with a significance level of 0.0001. Blue downward triangles represent single technical replicates and red triangles, if present, are for replicates where all associated technical replicates are above the line.
Figure 9C:
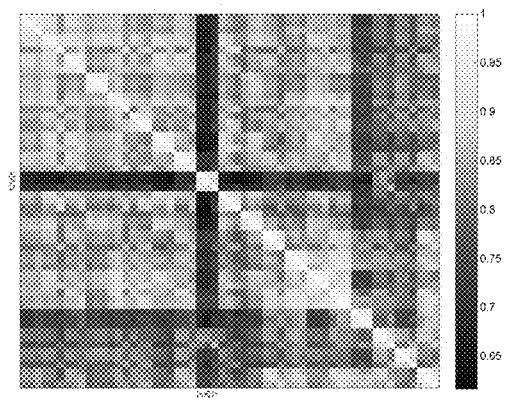
FIG. 9C shows quality control processing. The correlation coefficient of $\log_{10}$ peptide abundance values across LC-MS analyses.
Figure 9D:
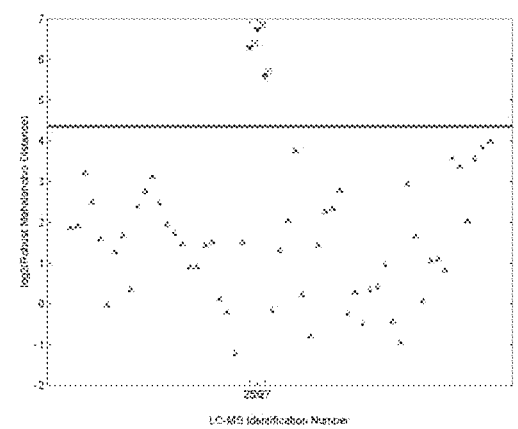
FIG. 9D shows quality control processing. The statistical analysis of the log 2 robust Mahalanobis distances (rMd) to determine if an LC-MS run should be removed from the dataset. The red horizontal line represents a critical value associated with a significance level of 0.0001. Blue downward triangles represent single technical replicates and red triangles, if present, are for replicates where all associated technical replicates are above the line.

For the verification non-transplant generated data, the final quantitative peptide identifications were independently processed through a series of steps including quality control, normalization, protein quantification, and comparative statistical analyses (FIG. 7). Peptide abundances were transformed to the $\log_{10}$ scale, and fibrosis severity categories were defined as fibrosis score=0; fibrosis score=1; and, fibrosis score=4, 5 or 6. Quality control processing was performed as previously described (Webb-Robertson et al., *J Proteome Res*, 2010. 9(11):5748-56; Matzke et al., *Bioinformatics*, 2011. 27(20): 2866-72). Two main data subsets (clusters) were identified using sppPCA due to batch differences throughout the analysis which resulted in 2 unique "subsets" within the non-transplant data (Webb-Roberston et al., *Sequential Projection Pursuit PCA-dealing with missing data associated with new Omics technologies*. Biotechniques, 2013. in press; FIG. 8). The two subsets were processed independently, starting with a quality check to identify LC-MS runs that have significantly different peptide abundance distributions (FIGS. 9A-9D), and peptide normalization using a statistical procedure for the analysis of proteomic normalization strategies (SPANS) that identifies the peptide selection method and data scaling factor which introduces the least amount of bias into the dataset (Webb-Robertson et al., *Proteomics*, 2011. 11(24):4736-41). For each subset, the peptide abundance values were normalized across the technical replicates. Subset 1 data were normalized with mean scaling using L order statistics (5%) peptide subset; subset 2 data were normalized with z-score scaling using percentage of peptides present. Normalized $\log_{10}$ abundance values were averaged across the technical replicates within each biological sample. For each subset, peptide abundance values were evaluated with a Tukey adjusted t-test to identify quantitative and qualitative significance patterns, respectively.

A total of 532 proteins in subset 1 and 464 proteins in subset 2 were estimated using a peptide signature vector approach to protein quantitation. Peptide level significance patterns were used for protein roll-up to select peptides within a protein that follow the same significance trends to estimate protein abundance. Protein abundance values were estimated using a standard R-rollup method as previously described (Polpitiya et al., *Bioinformatics*, 2008. 24(13):1556-8). Comparative statistical analyses between the 3 fibrosis severity categories (fibrosis score=0; fibrosis score=1; fibrosis score=4, 5 or 6) were performed using a Tukey adjusted t-test to assess differences in protein average abundance.

A meta-analysis of protein significance from subsets 1 and 2 was performed using Fisher's Inverse Score. The meta-analysis approach provides a mechanism that allows inference be made to proteins using data across many experiments. Fisher's Inverse Score approach considers the p-values resulting from the comparative statistical analysis of proteins. The Fisher's Inverse statistic is defined as, $$s_{Fisher} = -2\ln\left(\prod_i pvalue_i\right)$$

The statistic $s_{Fisher}$ follows a $\chi 2$ distribution with degrees of freedom (df) equal to 2 times the number of datasets. When a protein was observed in both experiments the df=2*2, otherwise df=2*1. Significance is based on a p-value threshold of 0.05.

There are a combined total of 581 unique proteins and 415 in common across subsets 1 and 2. The results of the meta-analysis approach can be summarized in 4 parts, of which parts 1-3 are associated with proteins that are present in both subsets (p=415) and thus statistics can be compared between the two subsets, and part 4 shows the counts for the proteins that are unique to each subset (Table 10, Tukey adjusted t-test).

TABLE 10

Meta-analysis of protein significance using Tukey adjusted p-values.
The number in meta-analysis results column (A/B) is the protein significance
after the p-values have been combined using the Fishers Inverse $\chi 2$ test
where A is the number significant and B is the number non-significant.

| Significance Indicator[1] | | Comparison (Score i vs. Score j) | | | | | |
|---|---|---|---|---|---|---|---|
| | | Fibrosis Score = 0 vs. Fibrosis Score = 1 | | Fibrosis Score = 0 vs. Fibrosis Score = 4/5/6 | | Fibrosis Score = 1 vs. Fibrosis Score = 4/5/6 | |
| Subset 1 (N = 42) | Subset 2 (N = 18) | Meta-Combined | analysis | Meta-Combined | analysis | Meta-Combined | analysis |
| Part 1. (df = 4) | | | | | | | |
| 1 | −1 | 0 | (0/0) | 0 | (0/0) | 0 | (0/0) |
| −1 | 1 | 0 | (0/0) | 0 | (0/0) | 0 | (0/0) |
| Part 2. (df = 4) | | | | | | | |
| +1 | +1 | 0 | (0/0) | 4 | (4/0) | 9 | (9/0) |
| −1 | −1 | 3 | (3/0) | 15 | (15/0) | 17 | (17/0) |
| 0 | 0 | 304 | (0/304) | 184 | (1/183) | 187 | (4/183) |
| Part 3. (df = 4) | | | | | | | |
| 1 | 0 | 17 | (13/4) | 23 | (20/3) | 17 | (11/6) |
| 0 | 1 | 2 | (2/0) | 10 | (5/5) | 11 | (9/2) |
| −1 | 0 | 13 | (5/8) | 37 | (23/7) | 22 | (18/4) |
| 0 | −1 | 10 | (4/6) | 26 | (16/10) | 21 | (14/7) |
| Part 4. (df = 2) | | | | | | | |
| +1 | NaN | 2 | (2/0) | 3 | (3/0) | 2 | (2/0) |
| NaN | +1 | 0 | (0/0) | 1 | (1/0) | 3 | (3/0) |
| −1 | NaN | 11 | (11/0) | 2 | (2/0) | 3 | (3/0) |
| NaN | −1 | 3 | (3/0) | 0 | (0/0) | 0 | (0/0) |
| 0 | NaN | 82 | (0/82) | 68 | (0/68) | 66 | (0/66) |
| NaN | 0 | 35 | (0/35) | 19 | (0/19) | 16 | (0/16) |

[1]Significance indicator value (+1) indicates the protein is statistically significant in favor of Score j; (−1) indicates the protein is statistically significant in favor of Score i; (0) indicates there is no evidence of a statistical difference between Scores i & j; and, (NaN) indicates the protein was not present in a subset.

In Part 1 of Table 10, proteins are demonstrated that have conflicting "significance" information across the two subsets. That is, those proteins which were found to have a statistically significant difference in favor of one score groups but in favor of the other score group for the other subset. For the Tukey adjusted t-tests comparing protein abundances, no proteins were found with conflicting information.

In Part 2 of Table 10, proteins are demonstrated with consistent significance information across the two subsets. For a small number of proteins that are non-significant for both subsets, there is a gain in significance after the merging due to an increase in power.

In Part 3 of Table 10, proteins are demonstrated that are significant in one subset and non-significant in the other subset. There are proteins for which the combination of the p-values does not give evidence of significance, but others for which the combination of the significant with the non-significant p-value again increases the power and identifies significance.

In Part 4 of Table 10, proteins are demonstrated that are unique to one subset or the other. A value of "NaN" means that the protein is not present in that subset. To combine p-values, the p-value for the missing protein is set to 1.0 so that to achieve significance a protein would need to have a p-value of less than 0.009. A balance is observed between the number of proteins that are still identified as significant and those for which the p-value increases to a non-significant level.

Figure 10:
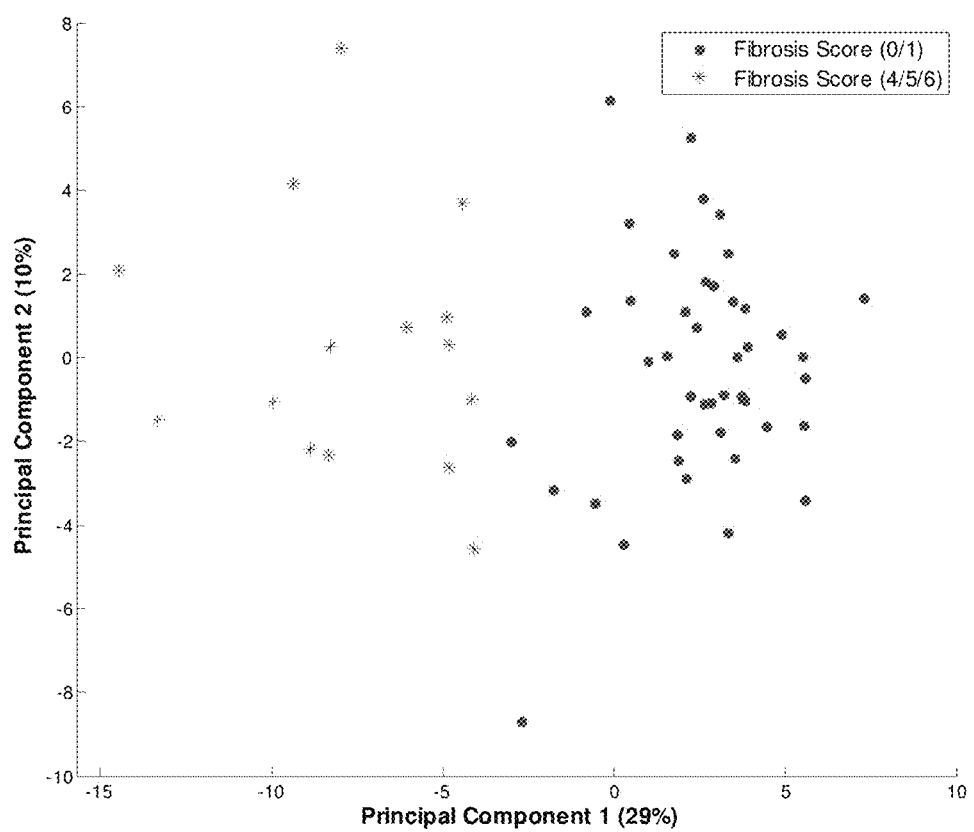
FIG. 10 is a plot showing the principal component analysis of the final protein candidate list. The first principal component explains 29% of the total variation in the protein abundance data, and discriminates the fibrosis categories.

The meta-analysis resulted in a non-redundant candidate list of 118 proteins which differentiate between 0, 1 fibrosis and >4 fibrosis. After implementing similar coverage requirements as the transplant sample results (minimum 2 significant peptides per protein), the final candidate list consisted of 78 proteins. To further explore these proteins, within each subset, missing values were imputed using a regularized EM algorithm (Schneider, *J. Climate*, 2001. 14(5):853-871), then standardized across subsets using a z-score. A principal component analysis (PCA) based on the combination of the two subsets was used to determine a linear combination of the 75 proteins that discriminates fibrosis categories such that category 1 are those patients with a 0 or 1 fibrosis score and category 2 are those patients with a 4, 5 or 6 fibrosis score. The first principal component (pc) explained 26% of the total variation in the imputed and standardized protein abundance dataset. In addition, when the PCA scores are labeled by fibrosis category membership, a separation of the fibrosis categories is evident (FIG. 10).

A receiver operator characteristic (ROC) analysis was performed to assess and compare various biological metrics for their sensitivity to discriminate the fibrosis categories. The metrics included are (1) the 75 individual protein abundances (n=60), (2) the scores of the linear combination of the 75 proteins resulting in the first pc (n=60), (3) the APRI score (n=55), and (4) the FBS score (n=17). The scores of first pc, APRI scores and FBS scores all performed well in the discrimination problem resulting in area under the curve (AUC) values of 1.0, 0.93 and 0.98, respectively.

Western Blot Analyses

Aliquots of depleted serum samples (see above) from selected pairs of fibrosis and non-fibrosis patients were used.

Briefly, 5 μg of each sample were electrophoresed using NuPage® Novex® 4-12% Bis-Tris SDS-PAGE gels (Life Technologies), alongside 5 μL SeeBlue® Plus2 Pre-stained Standard and 5 μL MagicMark™ XP Western Protein Standard (Life Technologies). Proteins were transferred to PVDF membranes followed by blocking with 5% non-fat dry milk in PBS containing 0.1% Triton X-100. Membranes were incubated overnight at 4° C. with primary antibodies at dilutions of 1:1000 or 1:500. Anti-QSOX1 was used at a 1:200 dilution for 1 h at room temperature. Secondary antibody incubations (1:5500) were carried out for 1 h at room temperature. All antibodies were from Santa Cruz biotechnology. SuperSignal West Femto Chemiluminescent Substrate (Thermo Scientific) was used for detection.

Example 2

IMS-MS Developments and Improvements to Increase Sensitivity and Duty Cycle

This example describes methods that were used to improve the sensitivity of protein detection by MS.

Practical use of IMS-MS was initially impeded by its low sensitivity due to significant ion losses at the IMS drift cell termini. This problem was solved by re-focusing both the ions exiting the source (prior to injection in the IMS drift cell) and those leaving the drift cell with ion funnels (FIG. 1A), making the addition of the IMS stage essentially lossless [13].

Another limitation that hindered widespread use of IMS-MS was its low duty cycle. Traditionally ions are only pulsed into the drift cell after all ions from the previous packet have exited, resulting in utilization of only a small percentage of the ions created in the source. To address this constraint, a multiplexing approach based on the Hadamard transform [14] was developed so that discreet packets of ions could co-exist in the drift cell as long as they did not overlap due to diffusional broadening (FIGS. 1B and 1C). This approach allows for much higher IMS duty cycle and has led to a significant increase in measurement sensitivity. Deconvolution of the pseudorandom sequence utilized in the multiplexing approach has also been shown to greatly reduce the noise in the spectra allowing a much higher signal to noise ratio for the resulting ions [15]. These improvements in addition to the reduced spectral congestion from the IMS separation have enabled faster gradient times when combined with LC, thereby increasing the throughput of sample analyses [12]. To take advantage of the faster sample analyses and higher sensitivity measurements, a LC-IMS-MS analytical platform was developed with the above sensitivity improvements for application to clinically focused large-scale proteomic measurements.

Example 3

LC-IMS-MS Platform Evaluation and Validation

This example shows application of the protein detection methods of Example 2 to detect expression of liver fibrosis related proteins.

In an initial evaluation of the new LC-IMS-MS platform, its performance was compared to an LC-MS platform (comprised of a commercially available LTQ Orbitrap Velos). Nine blood serum samples were analyzed on each platform, and a 100-min LC gradient was used for LC-MS, while a 60-min LC gradient was used for LC-IMS-MS. Even with the shorter analysis time, >20% more deisotoped spectral features (putative peptides) were detected with the LC-IMS-MS platform compared to the LC-MS platform (FIG. 2A), an observation attributed to the reduced spectral congestion from the additional IMS separation and the higher signal to noise ratios from multiplexing. These attributes allow additional coverage and confidence for the peptides observed with significant differential abundance in the LC-IMS-MS analyses and the detection of additional proteins not seen in the LC-MS experiments. To determine why more features were observed in the LC-IMS-MS platform even with a reduced LC gradient, a follow-up limit of detection study was performed and involved both platforms analyzing three technical replicates of a normal human serum sample spiked with eight non-human peptides ranging in concentrations from 100 pg/mL to 100 ng/mL. Overall, the LC-IMS-MS platform detected peptides at concentrations ~100× lower than the LC-MS platform with a linear correlation to concentrations, lower coefficient of variation (CV) values and modestly higher throughput (60-min vs. 100-min) as shown by Table 11 and FIG. 2B. These advantages illustrate the gains in enhanced dynamic range, proteome coverage, and increased speed for the LC-IMS-MS platform. To allow direct comparison of the TOF MS (60-min LC separation) to the LTQ Orbitrap Velos (100-min separation), the IMS drift cell was removed. The similarities in limits of detection for these two platforms (Table 11) showed that the increased measurement sensitivity observed with LC-IMS-MS can be attributed specifically to the IMS separation.

TABLE 11

Scaled abundance and coefficient of variation (CV) values for 8 non-human peptides spiked into human serum for 60-min LC-IMS-TOF MS, 60-min LC-TOF MS and 100-min LC-LTQ Orbitrap Velos analyses

| | | Peptide Scaled Abundance[a] and CV Values [b, c] | | |
|---|---|---|---|---|
| Spiking Level | Peptide | 60-min LC-IMS-TOFMS | 60-min LC-TOFMS | 100-min LC-LTQ Orbitrap Velos |
| 100 pg/mL | Melittin | ND | ND | ND |
| 100 pg/mL | Dynorphin A Porcine | 1.7 (18) | ND | ND |
| 1 ng/mL | Des Pro Ala Bradykinin | 21 (12) | ND | ND |
| 1 ng/mL | Leucine Enkephalin | 23 (10) | ND | ND |
| 10 ng/mL | 3X FLAG Peptide | 115 (8) | 125 (20) | ND |
| 10 ng/mL | Substance P | 126 (7) | 138 (18) | 112 (19) |
| 100 ng/mL | [Ala92]-Peptide 6 | 868 (4) | 848 (11) | 841 (12) |
| 100 ng/mL | Methionine Enkephalin | 1000 (3) | 1000 (9) | 1000 (10) |

[a] Peptide abundance values from 3 datasets were averaged and re-scaled to a range of 0 to 1000 for direct instrument comparison (by dividing the most abundant peptide value in each instrument and multiplying by 1000)
[b] CV values are in parenthesis
[c] ND = not detected Example 4

Statistical Trends for Proteins with Significant Differential Abundance Discriminating Between Fibrosis Conditions This example shows assessment of the statistical significance of data obtained using the protein detection methods of the preceding Examples towards detection of liver fibrosis related proteins.

To fully evaluate its applicability, the LC-IMS-MS platform was utilized in a study involving chronic liver disease, which is associated with a variety of origins, including viral hepatitis, alcohol abuse, nonalcoholic fatty liver disease and hepatic metabolic and immune disorder. Specifically matched blood serum samples chosen from 60 HCV patients following liver transplantation were initially utilized to evaluate the LC-IMS-MS platform for clinical use. These 60 samples represented 30 patients termed non-progressors (NP) who showed no or mild return of fibrosis over a range of times post-liver transplant (2 to 4 years), compared with 30 patients who developed "stage 3 to 4" fibrosis over a similar period of time and were stratified into either slow progressors (SP; stage 3-4 fibrosis at 3-4 years post-transplant) or fast progressors (FP; stage 3-4 fibrosis within 2 years post-transplant) (FIG. 3). The serum samples were collected at specific time points post-transplant (ranging between 150 and 771 days with in depth information on the patient cohort available in Reference [21] and its Supporting Material). Using a multi-variant approach, the specimens were matched for the most important clinical variables known to influence the risk of fibrosis progression associated with recurrent HCV after liver transplantation: donor age and cold ischemia time of the transplanted organ. Time to biopsy was also matched and multiple inclusion and exclusion criteria were applied, specifically patients with known confounders for fibrosis, such as CMV infection, greater than 1 episode of rejection, etc. were excluded. The specimens were adequately found and matched for these confounders due to the extensive number of patient samples available through the University of Washington Tissue Repository. Final matching resulted in 30 patient pairs (progressor vs. non-progressor), across both slow (14) and fast (16) fibrosis progression outcomes. All serum samples were analyzed utilizing the LC-IMS-MS platform with technical replicates allowing for global proteome evaluation of each patient sample.

Following data acquisition of the 60 HCV liver transplant serum samples with LC-IMS-MS, overall statistical significance was assessed, first at the peptide level and then protein significance was evaluated after merging peptide with significant differential abundance values distinguishing NP, SP, and FP conditions. If a protein was identified with only one significant non-unique peptide it was removed. In DAnTE software, peptide peak intensity values were converted to a log 2 scale statistically compared utilizing ANOVA (performed as a t-test with only two data types in each comparison) [22]. The analysis only focused on significantly changing peptides (p-values and q-values<0.05). The q-value of a test measures the proportion of false positives incurred (called the false discovery rate) when that particular test is called significant. Significantly changing peptides were assessed at a protein level using DAnTE's Rollup parameters (reference peptide based scaling). Statistically comparisons were also done at the protein level. Only significantly changing proteins were retained (some peptides were significant but they were in opposing directions, so the proteins were not significant when the peptides were rolled up). Final significant proteins identified required at least two significant peptide identifications. Statistical analysis revealed 136 differentially abundant proteins in the serum of transplant patients, 112 proteins were observed to discriminate between the NP and FP patient groups and 101 proteins between NP and SP patient groups, with 77 proteins overlapping, illustrated in FIG. 4A.

Example 5

Functional Classification and Comparison with Previous Finding

This example shows contextual analysis of some of the liver fibrosis related proteins that show differential expression using the protein detection methods of the preceding Examples.

Figure 4B:
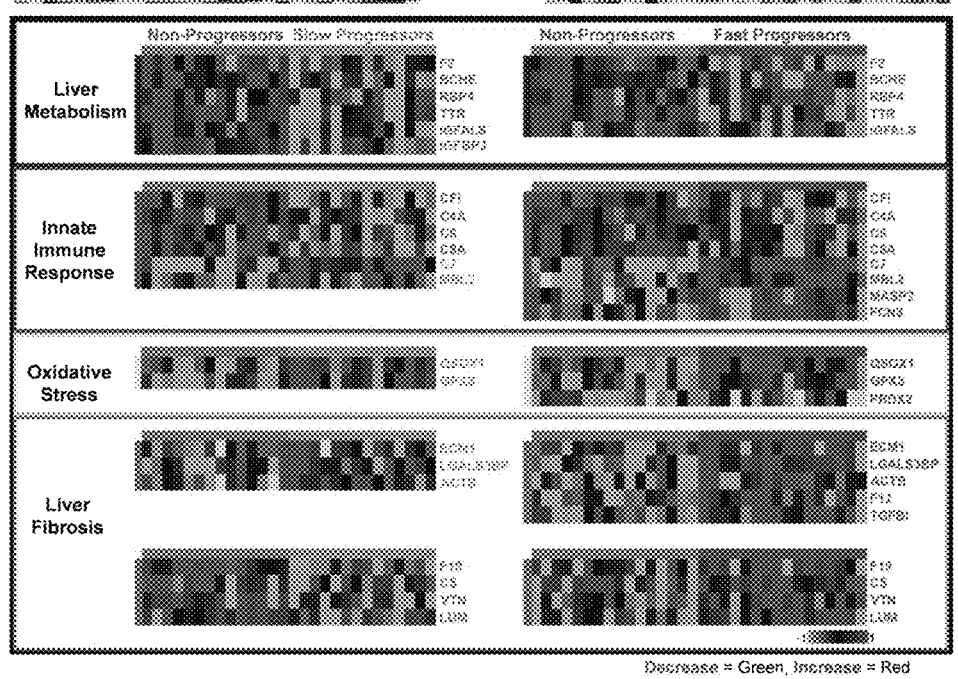
FIG. 4B provides heat maps illustrating the categorization of selected proteins with significant differential expression into four groups based on correlation with liver metabolism, innate immune response, oxidative stress or liver fibrosis. Gene names given in UniProtKB are used as abbreviated protein names. The twenty-five selected proteins are shown to illustrate the trend of each category. Decrease in relative expression is shown by green and increase in relative expression is shown by red (missing values are shown as grey).

Serum results were functionally classified, focusing on certain mechanisms relevant for comparison within liver function: liver metabolism, immune response (innate and adaptive), oxidative stress, architecture, and secreted effectors (Table 12, FIG. 4B). General trends reveal a decrease in serum level markers of liver metabolism for patients with developed fibrosis, while those related to oxidative stress increase (as seen in [23]). Mechanistically, this reflects a reduction in gross metabolism, in line with attenuation of liver function, but appears to do so under significant oxidative stress resulting in the production of stress response proteins. As with any comprehensive serum/plasma protein study, multiple signature immune proteins where also captured, including alterations in adaptive immunoglobulin responses, acute phase and inflammatory markers, and the complement pathway. Though likely not specific as markers of fibrosis progression, these signatures still reflect the gross alterations visible in this biofluid as a direct result of liver injury. Of specific relevance to HCV infection however, complement C4-A exhibited lower abundance in the SP and FP patient groups. Recent papers [24, 25] have shown that complement C4 activity is significantly lower in HCV infected patients because it is transcriptionally repressed by HCV proteins, consistent with the data.

TABLE 12

| | Gene | Transplant Model Fast Progressors vs their matched controls | Transplant Model Slow Progressors vs their matched controls | Fibrosis Model >Stage 4 Fibriosis |
|---|---|---|---|---|
| Proteins significantly increasing in the Slow and Fast Progressors (SP & FP) compared to their matched controls | | | | |
| Oxidative Stress | QSOX1 | ↑ | ↑ | ↑ |
| | IGLC1 | ↑ | ↑ | ↑ |
| | FCGR3A | ↑ | ↑ | ↑ |
| | A2M | ↑ | ↑ | ↑ |
| | AFM | ↑ | ↑ | ↑ |
| | ALCAM | ↑ | ↑ | ↑ |
| | APOB | ↑ | ↑ | ↓ |
| | C7 | ↑ | ↑ | ↑ |
| | CLU | ↑ | ↑ | ↓ |

TABLE 12-continued

| | Gene | Transplant Model Fast Progressors vs their matched controls | Transplant Model Slow Progressors vs their matched controls | Fibrosis Model >Stage 4 Fibriosis |
|---|---|---|---|---|
| Liver Architecture | ECM1 | ↑ | ↑ | ↑ |
| | ITIH3 | ↑ | ↑ | ↑ |
| Liver Architecture | LGALS3BP | ↑ | ↑ | ↑ |
| | VCAM1 | ↑ | ↑ | ↑ |
| | VWF | ↑ | ↑ | ↑ |

Proteins significantly decreasing in the Slow and Fast Progressors (SP & FP) compared to their matched controls

| | Gene | | | |
|---|---|---|---|---|
| Liver Metabolism | F2 | ↓ | ↓ | ↓ |
| | CFI | ↓ | ↓ | ↓ |
| | KLKB1 | ↓ | ↓ | ↓ |
| | F11 | ↓ | ↓ | ↓ |
| | CNDP1 | ↓ | ↓ | ↓ |
| Liver Metabolism | BCHE | ↓ | ↓ | ↓ |
| | APCS | ↓ | ↓ | ↓ |
| | APOH | ↓ | ↓ | ↓ |
| | AZGP1 | ↓ | ↓ | ↓ |
| Immune | C4A | ↓ | ↓ | ↓ |
| | C6 | ↓ | ↓ | ↓ |
| | C8A | ↓ | ↓ | ↓ |
| | C8B | ↓ | ↓ | ↓ |
| | C8G | ↓ | ↓ | ↓ |
| | HPX | ↓ | ↓ | ↓ |
| Liver Metabolism | IGFALS | ↓ | ↓ | ↓ |
| | ITIH1 | ↓ | ↓ | ↓ |
| | ITIH2 | ↓ | ↓ | ↓ |
| | ITIH4 | ↓ | ↓ | ↓ |
| | PRG4 | ↓ | ↓ | ↓ |
| Liver Metabolism | RBP4 | ↓ | ↓ | ↓ |
| | SERPINC1 | ↓ | ↓ | ↓ |
| | SERPIND1 | ↓ | ↓ | ↓ |
| Liver Metabolism | TTR | ↓ | ↓ | ↓ |
| | APOC3 | ↓ | ↓ | ↓ |

Proteins showing differentaly abundance changes in the Slow and Fast Progressors (SP & FP) compared to their matched controls - Up in FP/Down in SP

| | Gene | | | |
|---|---|---|---|---|
| Liver Architecture | F10 | ↑ | ↓ | ↓ |
| | SERPINA4 | ↑ | ↓ | ↓ |
| Liver Architecture | VTN | ↑ | ↓ | ↑ |
| Liver Architecture | LUM | ↑ | ↓ | ↑ |

Proteins significantly increasing/decreasing only in the Slow Progressors (SP) compared to their matched controls

| | Gene | | | |
|---|---|---|---|---|
| | SERPING1 | | ↑ | ↑ |
| | BTD | | ↓ | ↓ |
| | PLG | | ↓ | ↓ |
| | PROC | | ↓ | ↓ |
| | CPN1 | | ↓ | ↓ |
| | CPB2 | | ↓ | ↓ |
| | GC | | ↓ | ↓ |
| | GP5 | | ↓ | ↓ |

Proteins significantly increasing/decreasing in the Fast Progressors (FP) compared to their matched controls

| | Gene | | | |
|---|---|---|---|---|
| | C2 | ↑ | | ↓ |
| Liver Architecture | F12 | ↑ | | ↓ |
| | ANPEP | ↑ | | ↑ |
| | CP | ↑ | | ↑ |
| Liver Architecture | TGFBI | ↑ | | ↑ |
| | FCGBP | ↑ | | ↓ |
| | SERPINA7 | ↑ | | ↓ |
| | PVR | ↑ | | ↑ |
| | AGT | ↓ | | ↓ |
| | H6PD | ↓ | | ↓ |
| | PROCR | ↑ | | ↑ |
| | VASN | ↑ | | ↑ |

Proteins significantly increasing/decreasing only in AK dataset

| | Gene | | | |
|---|---|---|---|---|
| | Ig lambda chain V-I region NEWM | | | ↑ |
| | APOC1 | | | ↑ |
| | ICAM1 | | | ↑ |
| | CSF1R | | | ↑ |

TABLE 12-continued

| Gene | Transplant Model Fast Progressors vs their matched controls | Transplant Model Slow Progressors vs their matched controls | Fibrosis Model >Stage 4 Fibrosis |
|---|---|---|---|
| DBH | | | ↑ |
| COL6A3 | | | ↑ |
| COMP | | | ↑ |
| CD163 | | | ↑ |
| LYVE1 | | | ↑ |
| LCAT | | | ↓ |
| CPN2 | | | ↓ |
| PROZ | | | ↓ |
| MASP1 | | | ↓ |
| SEPP1 | | | ↓ |
| RARRES2 | | | ↓ |

Trends were observed in the panel of liver architecture proteins allowing for differentiation of the NP, SP, and FP patient groups. Extracellular matrix proteins such as ECM1 and galectin-3-binding proteins, which contribute to the collagenous matrix of the fibrotic tissue in chronic hepatic fibrosis, both increased in SP and FP patient groups, as well as cytoskeletal β-actin (ACTB) which increases in a radiation-induced skin and muscular fibrosis study [26]. A significant increase was observed in FP patients for transforming growth factor-β-induced protein ig-h3 (TGFBI) and coagulation factor XII (F12). Finally, differential responses were observed in some protein markers such as vitronectin (VTN), lumican (LUM), coagulation factor X (F10) and complement factor 5 (C5), which decrease in SP, but increase in FP.

Recent efforts report complementary mRNA and protein level characterization of liver-transplant biopsy tissue collected from a patient population which overlaps, in part, with the current serum samples [30, 31]. Previous tissue studies were longitudinal in nature, including early and late post-transplant, and accurately describe the gene and protein expression patterns and networks that differentially distinguish severity of fibrosis progression post-transplant. When comparing the liver tissue and serum results a strong oxidative stress environment and response directly linked to liver injury is reflected in both liver tissue and through protein serum levels. This is confirmed through metabolite analysis performed on the same serum samples, showing a unique metabolic profile categorized by metabolite alterations in glutathione hemostasis and oxidative stress [30], consistent with previous finding [32, 33]. Alterations in both adaptive and innate immune responses are also in common and consistent with other HCV-associated fibrosis transplant studies [30, 34]. Finally, indications of liver function attenuation (reduction in metabolism and secretion of effectors), were also reflected in both the serum and tissue findings and correlated with fibrosis progression [30].

This initial application of the LC-IMS-MS platform demonstrates a robust characterization of potential differentiating serum proteins, with faster throughput (40% gain) while maintaining or exceeding sensitivity compared to current conventional platforms (Table 11).

Example 6

Non-Transplant Patient Serum Verification Analysis and Comparison

This example shows validation of results obtained on transplant patients with liver fibrosis using protein detection methods of the preceding Examples against results obtained using the methods on non-transplant liver fibrosis subjects.

Figure 5A:
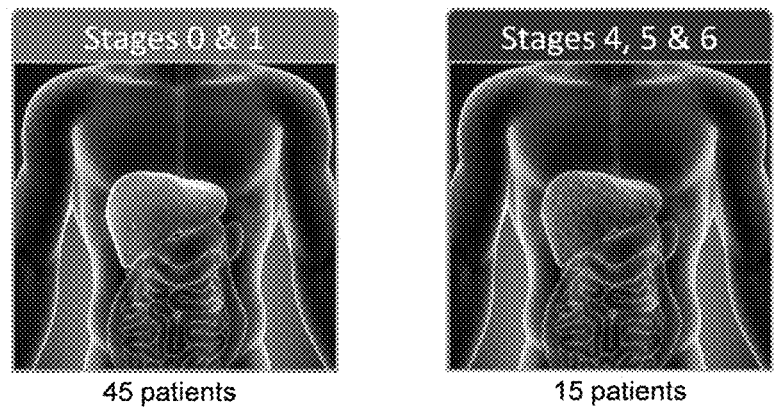
FIG. 5A illustrates the categorization of 60 HCV infected non-transplant patients into two categories, Stages 0 & 1 and Stages 4, 5 & 6. Blood samples from the 60 HCV infected non-transplant patients were utilized for comparison and validation of the transplant patient results.

Investigations utilizing a liver transplant patient population confer multiple advantages in studies involving fibrosis progression (part of which is the rapidity with which fibrosis develops post-transplant), but it is recognized that such studies also introduce clinical confounders and variables not mechanistically linked to progression of liver fibrosis but directly related to the transplantation itself and immunosuppressive environments. These factors likely add analytical complexity to an already dynamic clinical investigation. To provide clarity towards significant findings from the transplant model and at the same time verify the subset of detected serum proteins which are directly related to fibrosis progression, the LC-IMS-MS platform described above was utilized to survey a completely independent HCV-infected but non-transplant patient cohort). A total of 60 patient serum samples were identified and analyzed based upon fibrosis stratification of Ishak score 0-1 versus 4-6, with timeframe of sampling within 6 months of a diagnostic biopsy as shown in FIG. 5A.

Figure 5B:
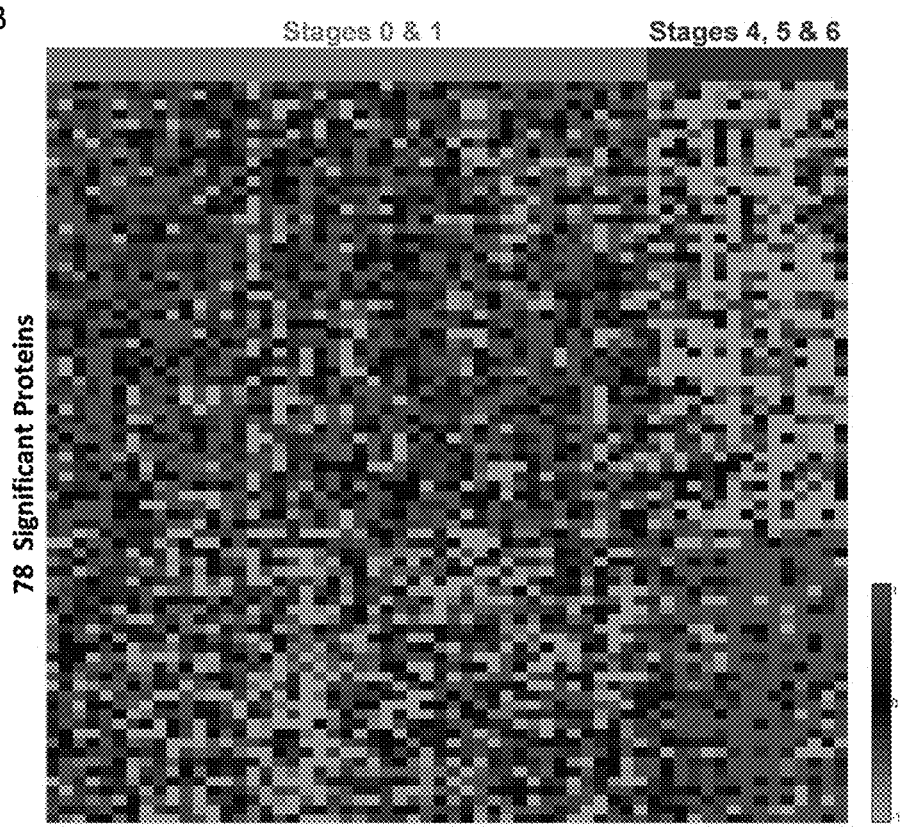
FIG. 5B provides heat maps illustrating the relative log 2 intensity change for proteins showing significant differential expression in the non-transplant patient groups. Each column represents one of the 60 patients and each row one of the 78 significant proteins shown in Table 5. Trends between the patient groups are clearly observed, but biodiversity in the human population is also discerned. Decrease in relative abundance is shown by green and increase by red.

Statistical analysis of the subsequent peptide and protein results was performed using an independent analysis pipeline (See Example 1 for details) which resulted in the orthogonal identification of 78 proteins (see Table 5) which differentiate between the fibrosis classes (FIG. 5B). Notably, 81% of these proteins (63) overlap with those that significantly differentiate fibrosis progression in the initial transplant patient results, with the majority (43) overlapping with those in common between SP and FP. Additionally, after excluding 4 proteins which decrease in SP, but increase in FP, >91% are observed with common abundance directionality, providing a strong orthogonal validation of core proteins based upon both transplant and non-transplant studies. Furthermore, of the 14 proteins uniquely significant in the non-transplant data, half have supporting significant peptides in the transplant data, but were initially excluded due to lack of multiple peptides per protein. (See Table 12 for protein overlap information)

Beyond validation purposes, comparison of the transplant and non-transplant results provides evidence concerning the liver fibrosis specificity of serum protein levels, and aids in identifying signatures which may be more driven by the transplant environment. The core observations previously observed with the transplant study still hold in the non-transplant results. Specifically, as seen in the proteins depicted in FIG. 4B, decreases are still consistent in liver metabolism, proteins F2, BCHE, RBP4, TTHY and IGFALS; decreasing immune response protein CO4A; increasing oxidative stress protein QSOX1; and increasing liver architecture proteins ECM1, LGALS3BP and TGFBI. Other verified proteins previously described include HPX, AGT, PROC and A2M. Thus, in some examples the disclosed methods and systems use at least (a) F2, BCHE, RBP4, TTHY, IGFALS, CO4A, QSOX1, ECM1, LGALS3BP and TGFBI, or (b) F2, BCHE, RBP4, TTHY, IGFALS, CO4A, QSOX1, ECM1, LGALS3BP, TGFBI, HPX, AGT, PROC and A2M. With regard to the subset of serum markers found only with transplant results, a much more robust adaptive immune response is seen, in both the number and magnitude of immunoglobulin related serum identifications, which is partially observed in the non-transplant results (Table 12). Additionally, a number of general hepatic classical serum/plasma proteins, ALB, ORM2, ORM1, A1AT, HBB, HP, APOA1, APOA2 and CO3, were also uniquely significant in the transplant model but not verified in the non-transplant results. Interestingly most of these proteins were immunoaffinity depleted prior to platform analysis, so their initial differential abundance was based upon either detection of an altered protein state (confirmation change, denature or degraded form), or their protein abundance was altered enough to overwhelm capture on the affinity column.

Example 7

Comparison with Current Metrics of Fibrosis Progression

This example compares fibrosis tracking performance obtainable using the LC-IMS-MS improved sensitivity protein detection method against current metrics for fibrosis progression. This example also validates results from the LC-IMS-MS platform for five proteins showing differential expression in both the transplant and non-transplant patient groups using Western blot immunoassays.

There are several current clinically applied tests and measures to track fibrosis progression in patients, two of which, APRI calculation [39] and FIBROSpect score [40], where measured herein and were compared with the identified protein signatures. Using the non-transplant results, a receiver operator characteristic (ROC) comparative analysis was performed comparing 75 identified and quantified protein values (78 minus the removal of immunoglobulin IDs) with measured FIBROSpect scores (n=17) and the calculated APRI score (n=60).

The set of 75 serum proteins detected by LC-IMS-MS was able to achieve a full discrimination of patients, area under the curve (AUC)=1, compared to FIBROSpect AUC=0.98 and APRI AUC=0.93. FIBROSpect results are in line with previous studies which showed its clear utility to discrimination between advanced and mild disease (0, 1 Ishak versus >4 Ishak) [41]. However there are limitations for both sensitivity and selectivity when reporting the FIBROSpect middle test range (correlation to Ishak 2-3) [41]. The current protein markers performed as well as FIBROSpect scores in discrimination of mild versus advanced disease, and a comprehensive list of markers, as presented, may perform well in middle disease determination, which would be a significant benefit over currently available measures.

Figure 6:
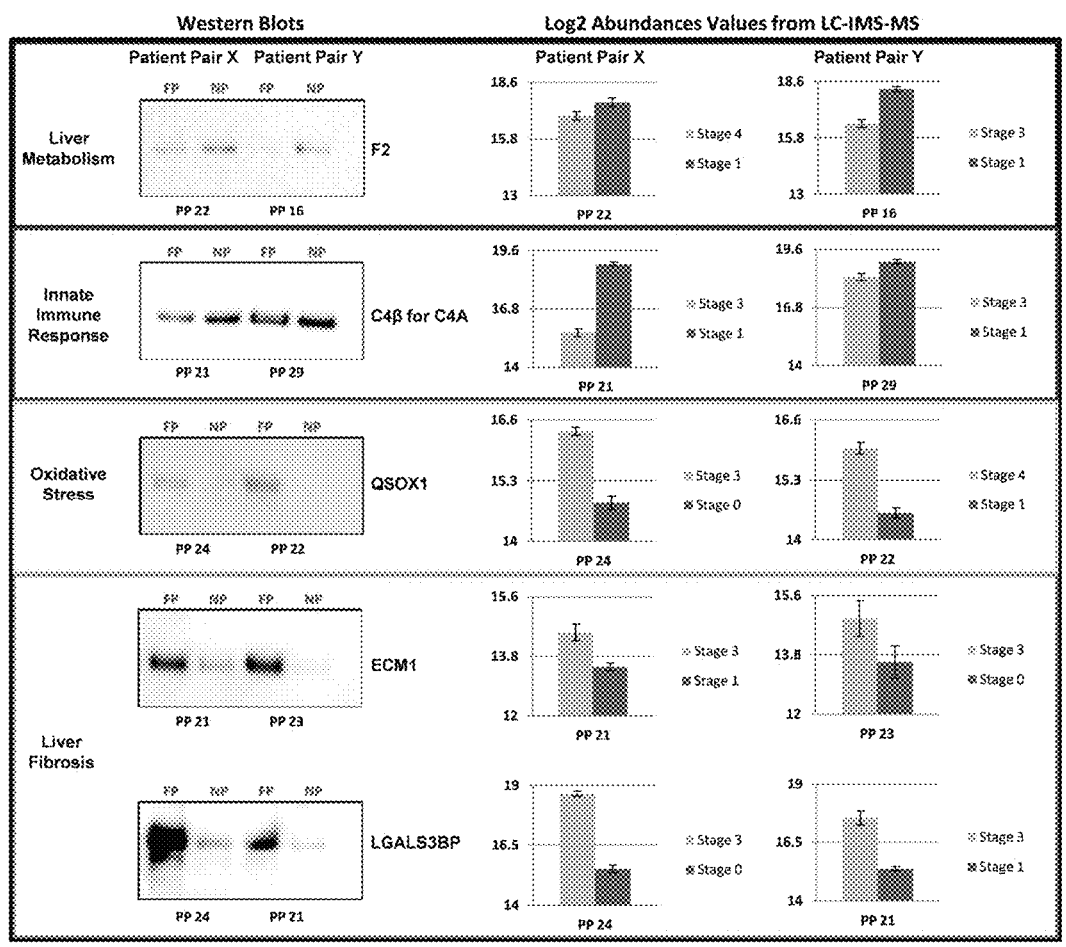
FIG. 6 illustrates Western blot (left) and LC-IMS-MS abundance (right) analyses of certain liver fibrosis patients where fast progressors (FP) were analyzed against their matched controls (NP). Patient fibrosis stage is noted on the bar graphs for the LC-IMS-MS abundance data. Patient pair is abbreviated as PP for clarity. For the Western blots an equal amount (5 µg) of each serum protein sample was loaded. Targets were proteins involved in liver metabolism (F2: patient pairs 22 and 16), the innate immune system (C4A: patient pairs 21 and 29 (the Western targeted C4 β-chain, a cleavage product of C4A), oxidative stress (QSOX1: patient pairs 24 and 22) and liver fibrosis (ECM1: patient pairs 21 and 23 and LGALS3BP: patient pairs 24 and 21).

To provide a more traditional validation of the results from the LC-IMS-MS platform, a limited subset of Western blot immunoassays were performed on five proteins with significant differential abundance in both the transplant and non-transplant patients groups (F2, C4A, QSOX1, ECM1 and LGALS3BP). Within the LC-IMS-MS studies, F2 and C4A both decrease in patients with fibrosis while QSOX1, ECM1 and LGALS3BP increase. These results were essentially mirrored in the immunoassay blot results where two transplant NP-FP patient pair serum samples were blotted for each protein as shown in FIG. 6. The corresponding bar graphs represent the LC-IMS-MS measured protein values, providing an orthogonal validation of LC-IMS-MS platform.

REFERENCES

1. Picotti P, Rinner O, Stallmach R, Dautel F, Farrah T, Domon B, et al. High-throughput generation of selected reaction-monitoring assays for proteins and proteomes. Nat Methods. 2010; 7(1):43-6.
2. Addona T A, Abbatiello S E, Schilling B, Skates S J, Mani D R, Bunk D M, et al. Multi-site assessment of the precision and reproducibility of multiple reaction monitoring-based measurements of proteins in plasma. Nat Biotechnol. 2009; 27(7):633-41. PMCID: 2855883.
3. Roschinger W, Olgemoller B, Fingerhut R, Liebl B, Roscher A A. Advances in analytical mass spectrometry to improve screening for inherited metabolic diseases. Eur J Pediatr. 2003; 162 Suppl 1:S67-76.
4. Gallien S, Duriez E, Domon B. Selected reaction monitoring applied to proteomics. J Mass Spectrom. 2011; 46(3):298-312.
5. Woodcock J. The prospects for "personalized medicine" in drug development and drug therapy. Clin Pharmacol Ther. 2007; 81(2):164-9.
6. Chan I S, Ginsburg G S. Personalized medicine: progress and promise. Annu Rev Genomics Hum Genet. 2011; 12:217-44.
7. Hutchinson L. Personalized cancer medicine: era of promise and progress. Nat Rev Clin Oncol. 2011; 8(3): 121.
8. Shen Y F, Zhao R, Berger S J, Anderson G A, Rodriguez N, Smith R D. High-efficiency nanoscale liquid chromatography coupled on-line with mass spectrometry using nanoelectrospray ionization for proteomics. Analytical Chemistry. 2002; 74(16):4235-49.
9. Mason E, McDaniel E. Transport Properties of Ions in Gases. New York: Wiley; 1988.
10. Guevremont R, Siu K W, Wang J, Ding L. Combined Ion Mobility/Time-of-Flight Mass Spectrometry Study of Electrospray-Generated Ions. Anal Chem. 1997; 69(19): 3959-65.
11. Sowell R A, Koeniger S L, Valentine S J, Moon M H, Clemmer D E. Nanoflow LC/IMS-MS and LC/IMS-CID/MS of protein mixtures. J Am Soc Mass Spectrom. 2004; 15(9):1341-53.
12. Baker E S, Livesay E A, Orton D J, Moore R J, Danielson W F, 3rd, Prior D C, et al. An LC-IMS-MS platform providing increased dynamic range for high-throughput proteomic studies. J Proteome Res. 2010; 9(2):997-1006. PMCID: 2819092.
13. Tang K, Shvartsburg A A, Lee H N, Prior D C, Buschbach M A, Li F, et al. High-sensitivity ion mobility spectrometry/mass spectrometry using electrodynamic ion funnel interfaces. Anal Chem. 2005; 77(10):3330-9. PMCID: 1829302.
14. Belov M E, Buschbach M A, Prior D C, Tang K, Smith R D. Multiplexed ion mobility spectrometry-orthogonal time-of-flight mass spectrometry. Anal Chem. 2007; 79(6):2451-62. PMCID: 3302721.
15. Clowers B H, Belov M E, Prior D C, Danielson W F, 3rd, Ibrahim Y, Smith R D. Pseudorandom sequence modifi- 16. Llovet J M, Burroughs A, Bruix J. Hepatocellular carcinoma. Lancet. 2003; 362:1907-17.
17. Charlton M, Ruppert K, Belle S H, Bass N, Schafer D, Wiesner R H, et al. Long-term results and modeling to predict outcomes in recipients with HCV infection: results of the NIDDK liver transplantation database. Liver Transpl. 2004; 10:1120-30.
18. Thomson B J, Finch R G. Hepatitis C virus infection. Clin Microbiol Infect. 2005; 11:86-94.
19. Mukherjee S, Sorrell M F. Noninvasive tests for liver fibrosis. Semin Liver Dis. 2006; 26(4):337-47.
20. Plebani M, Basso D. Non-invasive assessment of chronic liver and gastric diseases. Clin Chim Acta. 2007; 381(1):39-49.
21. Diamond D L, Krasnoselsky A L, Burnum K E, Monroe M E, Webb-Robertson B J, McDermott J E, et al. Proteome and computational analyses reveal new insights into the mechanisms of hepatitis C virus-mediated liver disease posttransplantation. Hepatology. 2012; 56(1):28-38. PMCID: 3387320.
22. Polpitiya A D, Qian W J, Jaitly N, Petyuk V A, Adkins J N, Camp D G, 2nd, et al. DAnTE: a statistical tool for quantitative analysis of -omics data. Bioinformatics. 2008; 24(13):1556-8. PMCID: 2692489.
23. Diamond D L, Jacobs J M, Paeper B, Proll S C, Gritsenko M A, Carithers R L, Jr., et al. Proteomic profiling of human liver biopsies: hepatitis C virus-induced fibrosis and mitochondrial dysfunction. Hepatology. 2007; 46(3):649-57.
24. Imakiire K, Uto H, Sato Y, Sasaki F, Mawatari S, Ido A, et al. Difference in serum complement component C4a levels between hepatitis C virus carriers with persistently normal alanine aminotransferase levels or chronic hepatitis C. Mol Med Report. 2012; 6(2):259-64.
25. Banerjee A, Mazumdar B, Meyer K, Di Bisceglie A M, Ray R B, Ray R. Transcriptional repression of C4 complement by hepatitis C virus proteins. J Virol. 2011; 85(9): 4157-66. PMCID: 3126272.
26. Martin M, Lefaix J L, Pinton P, Crechet F, Daburon F. Temporal modulation of TGF-beta 1 and beta-actin gene expression in pig skin and muscular fibrosis after ionizing radiation. Radiat Res. 1993; 134(1):63-70.
27. Jablonska E, Markart P, Zakrzewicz D, Preissner K T, Wygrecka M. Transforming growth factor-beta1 induces expression of human coagulation factor XII via Smad3 and JNK signaling pathways in human lung fibroblasts. J Biol Chem. 2010; 285(15):11638-51. PMCID: 2857041.
28. Scotton C J, Krupiczojc M A, Konigshoff M, Mercer P F, Lee Y C, Kaminski N, et al. Increased local expression of coagulation factor X contributes to the fibrotic response in human and murine lung injury. J Clin Invest. 2009; 119(9):2550-63. PMCID: 2735922.
29. Hillebrandt S, Wasmuth H E, Weiskirchen R, Hellerbrand C, Keppeler H, Werth A, et al. Complement factor 5 is a quantitative trait gene that modifies liver fibrogenesis in mice and humans. Nat Genet. 2005; 37(8):835-43.
30. Diamond D L, Krasnoselski A, Burnum K E, Susnow N, Webb-Robertson B J, McDermott J E, et al. Proteome and Computational Analyses Reveal New Insights into the Mechanisms of Hepatitis C Virus Mediated Liver Disease Post-Transplantation. Hepatology. 2012; in press.
31. Rasmussen A L, Tchitchek N, Susnow N J, Krasnoselsky A L, Diamond D L, Yeh M M, et al. Early transcriptional programming links progression to hepatitis C virus-induced severe liver disease in transplant patients. Hepatology. 2012; 56(1):17-27. PMCID: 3349763.
32. Soga T, Sugimoto M, Honma M, Mori M, Igarashi K, Kashikura K, et al. Serum metabolomics reveals gamma-glutamyl dipeptides as biomarkers for discrimination among different forms of liver disease. Journal of hepatology. 2011; 55(4):896-905.
33. Roe B, Kensicki E, Mohney R, Hall W W. Metabolomic profile of hepatitis C virus-infected hepatocytes. PloS one. 2011; 6(8):e23641. PMCID: 3154941.
34. Smith M W, Walters K A, Korth M J, Fitzgibbon M, Proll S, Thompson J C, et al. Gene expression patterns that correlate with hepatitis C and early progression to fibrosis in liver transplant recipients. Gastroenterology. 2006; 130(1):179-87.
35. Qin S, Zhou Y, Lok A S, Tsodikov A, Yan X, Gray L, et al. SRM targeted proteomics in search for biomarkers of HCV-induced progression of fibrosis to cirrhosis in HALT-C patients. Proteomics. 2012; 12(8):1244-52.
36. Cheung K J, Libbrecht L, Tilleman K, Deforce D, Colle I, Van Vlierberghe H. Galectin-3-binding protein: a serological and histological assessment in accordance with hepatitis C-related liver fibrosis. Eur J Gastroenterol Hepatol. 2010; 22(9):1066-73.
37. Cheung K J, Tilleman K, Deforce D, Colle I, Moreno C, Gustot T, et al. Usefulness of a novel serum proteome-derived index FI-PRO (fibrosis-protein) in the prediction of fibrosis in chronic hepatitis C. Eur J Gastroenterol Hepatol. 2011; 23(8):701-10.
38. Bell L N, Theodorakis J L, Vuppalanchi R, Saxena R, Bemis K G, Wang M, et al. Serum proteomics and biomarker discovery across the spectrum of nonalcoholic fatty liver disease. Hepatology. 2010; 51(1):111-20. PMCID: 2903216.
39. Borsoi Viana M S, Takei K, Collarile Yamaguti D C, Guz B, Strauss E. Use of AST platelet ratio index (APRI Score) as an alternative to liver biopsy for treatment indication in chronic hepatitis C. Annals of hepatology. 2009; 8(1):26-31.
40. Patel K, Gordon S C, Jacobson I, Hezode C, Oh E, Smith K M, et al. Evaluation of a panel of non-invasive serum markers to differentiate mild from moderate-to-advanced liver fibrosis in chronic hepatitis C patients. Journal of hepatology. 2004; 41(6):935-42.
41. Christensen C, Bruden D, Livingston S, Deubner H, Homan C, Smith K, et al. Diagnostic accuracy of a fibrosis serum panel (FIBROSpect II) compared with Knodell and Ishak liver biopsy scores in chronic hepatitis C patients. Journal of viral hepatitis. 2006; 13(10):652-8.
42. Baker E S, Clowers B H, Li F, Tang K, Tolmachev A V, Prior D C, et al. Ion mobility spectrometry-mass spectrometry performance using electrodynamic ion funnels and elevated drift gas pressures. J Am Soc Mass Spectrom. 2007; 18(7):1176-87. PMCID: 3292285.
43. Livesay E A, Tang K, Taylor B K, Buschbach M A, Hopkins D F, LaMarche B L, et al. Fully Automated Four-Column Capillary LC-MS System for Maximizing Throughput in Proteomic Analyses. Analytical Chemistry. 2007; 80(1):294-302.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09651563B2). An electronic copy of the "Sequence Listing" will also be available from the USPTO upon request and payment of the fee set forth in 37 CFR 1.19(b)(3).

We claim:

1. A kit for the diagnosis or prognosis of liver fibrosis in a subject, comprising:
   labeled antibodies for detecting at least two liver fibrosis-related molecules,
   labeled nucleic acid probes for detecting at least two liver fibrosis-related molecules,
   labeled nucleic acid primers for detecting at least two liver fibrosis-related molecules, or combinations thereof,
   wherein the at least two liver fibrosis-related molecules comprise at least two of: receptor-type tyrosine-protein phosphatase gamma (PTPRG); sulfhydryl oxidase 1 (QSOX1); glutathione peroxidase 3 (GPX3); Ig kappa chain V-III region VG; Ig kappa chain V-III region HAH; Ig lambda chain V-III region LOI; Ig alpha-1 chain C region (IGHA1); Ig gamma-1 chain C region (IGHG1); Ig gamma-2 chain C region (IGHG2); Ig mu chain C region (IGHM); Ig kappa chain C region (IGKC); Ig kappa chain V-I region HK102 (IGKV1-5); Ig lambda chain C regions (IGLC1); low affinity immunoglobulin gamma Fc region receptor III-A (FCGR3A); alpha-2-macroglobulin (A2M); actin, cytoplasmic 1 (ACTB); afamin (AFM); Alpha-2-HS-glycoprotein (AHSG); CD166 antigen (ALCAM); apolipoprotein B-100 (APOB); apolipoprotein E (APOE); complement component C7; clusterin (CLU); extracellular matrix protein 1 (ECM1); hemoglobin subunit beta; inter-alpha-trypsin inhibitor heavy chain H3 (ITIH3); galectin-3-binding protein (LGALS3BP); mannose-binding protein C (MBL2); L-selectin; alpha-1-antitrypsin (SERPINA1); corticosteroid-binding globulin (SERPINA6); sex hormone-binding globulin (SHBG); vascular cell adhesion protein 1 (VCAM1); von Willebrand factor (VWF); prothrombin (F2); complement factor B (CFB); complement factor I (CFI); complement C1s subcomponent (C1S); complement C1r subcomponent (C1R); plasma kallikrein (KLKB1); coagulation factor XI (F11); coagulation factor IX (F9); Beta-Ala-His dipeptidase (CNDP1); cholinesterase (BCHE); serum albumin (ALB); serum amyloid P-component (APCS); apolipoprotein A-IV (APOA4); apolipoprotein C-III (APOC3); Beta-2-glycoprotein 1 (APOH); zinc-alpha-2-glycoprotein (AZGP1); complement C4-A (C4A); complement component C6 (C6); complement component C8 alpha chain (C8A); complement component C8 beta chain (C8B); complement component C8 gamma chain (C8G); complement component C9 (C9); fibrinogen alpha chain (FGA); hemopexin (HPX); histidine-rich glycoprotein (HRG); insulin-like growth factor-binding protein complex acid labile subunit (IGFALS); inter-alpha-trypsin inhibitor heavy chain H1 (ITIH1); inter-alpha-trypsin inhibitor heavy chain H2 (ITIH2); inter-alpha-trypsin inhibitor heavy chain H4 (ITIH4); alpha-1-acid glycoprotein 1 (ORM1); alpha-1-acid glycoprotein 2 (ORM2); proteoglycan 4 (PRG4); retinol-binding protein 4 (RBP4); alpha-1-antichymotrypsin (SERPINA3); antithrombin-III (SERPINC1); heparin cofactor 2 (SERPIND1); transthyretin (TTR); coagulation factor X (F10); fibronectin (FN1); complement C5 (C5); kallistatin (SERPINA4); vitronectin (VTN); lumican (LUM); hemoglobin subunit alpha (HBA1); plasma protease C1 inhibitor (SERPING1); Ig kappa chain V-I region AU; Ig kappa chain V-II region Cum Ig kappa chain V-IV region; N-acetylmuramoyl-L-alanine amidase (PGLYRP2); biotinidase (BTD); plasminogen (PLG); vitamin K-dependent protein C (PROC); complement C1r subcomponent-like protein (C1RL); carboxypeptidase N catalytic chain (CPN1); carboxypeptidase B2 (CPB2); apolipoprotein A-I (APOA1); complement C4-B (C4B); vitamin D-binding protein (GC); platelet glycoprotein V (GP5); haptoglobin (HP); insulin-like growth factor-binding protein 3 (IGFBP3); kininogen-1 (KNG1); vitamin K-dependent protein S (PROS 1); protein Z-dependent protease inhibitor (SERPINA10); pigment epithelium-derived factor (SERPINF1); alpha-2-antiplasmin (SERPINF2); thrombospondin-1 (THBS1); prostaglandin-H2 D-isomerase (PTGDS); carbonic anhydrase 1 (CA1); fructose-bisphosphate aldolase B (ALDOB); complement C2 (C2); coagulation factor XII (F12); mannan-binding lectin serine protease 2 (MASP2); hyaluronan-binding protein 2 (HABP2); aminopeptidase N (ANPEP); ectonucleotide pyrophosphatase/phosphodiesterase family member 2 (ENPP2); ceruloplasmin (CP); peroxiredoxin-2 (PRDX2); alpha-1B-glycoprotein (A1BG); transforming growth factor-beta-induced protein ig-h3 (TGFB1); monocyte differentiation antigen CD14 (CD14); complement C3 (C3); endoglin (ENG); endothelial protein C receptor (PROCR); IgGFc-binding protein (FCGBP); ficolin-3 (FCN3); fetuin-B (FETUB); hepatocyte growth factor-like protein (MST1); cell surface glycoprotein MUC18 (MCAM); neuropilin-1 (NRP1); secreted phosphoprotein 24 (SPP2); thyroxine-binding globulin (SERPINA7); vasorin (VASN); collagen alpha-1(XVIII) chain (COL18A1); poliovirus receptor (PVR); apolipoprotein A-II (APOA2); Peptidase inhibitor 16 (PI16); GDH/6PGL endoplasmic bifunctional protein (H6PD); angiotensinogen (AGT); complement factor H (CFH); c-reactive protein (CRP); gelsolin (GSN); apolipoprotein C-I (APOC1); macrophage colony-stimulating factor 1 receptor (CSF1R); dopamine beta-hydroxylase (DBH); collagen alpha-3(VI) chain (COL6A3); cartilage oligomeric matrix protein (COMP); Ig lambda chain V-I region NEWM; intercellular adhesion molecule 1 (ICAM1); scavenger receptor cysteine-rich type 1 protein M130 (CD163); lymphatic vessel endothelial hyaluronic acid receptor 1 (LYVE1); phosphatidylcholine-sterol acyltransferase (LCAT); carboxypeptidase N subunit 2 (CPN2); vitamin K-dependent protein Z (PROZ); mannan-binding lectin serine protease 1 (MASP1); selenoprotein P (SEPP1); and retinoic acid receptor responder protein 2 (RARRES2), or any of SEQ ID NOS: 1-5544, wherein the labeled antibodies, labeled nucleic acid probes, and labeled nucleic acid primers comprise a fluorophore, chemiluminescent agent, enzyme, hapten, metal complex, or radioactive isotope.

2. The kit of claim 1, wherein the kit comprises labeled antibodies specific for the at least two liver fibrosis-related molecules.

3. The kit of claim 2, wherein the kit further comprises:
labeled secondary antibodies specific for the antibodies specific for the at least two liver fibrosis-related molecules;
a substrate, to which the labeled antibodies specific for the at least two liver fibrosis-related molecules are attached;
an alarm which indicates the presence of liver fibrosis, wherein the alarm is activated if at least two liver fibrosis-related molecules are detected with differential expression relative to control levels for a subject without liver fibrosis, wherein differential expression comprises an increase or decrease of at least 10%;
an alarm which indicates the presence of liver fibrosis, wherein the alarm is activated if at least 80% of the at least two liver-fibrosis molecules are detected with differential expression relative to control levels for a subject without liver fibrosis or with non-progressing liver fibrosis, wherein differential expression comprises an increase or decrease of at least 10%;
an interface configured to accept input of a criterion for diagnosis or prognosis of liver fibrosis;
an interface configured to accept input of a selection of the at least two liver fibrosis-related molecules; or
combinations thereof.

4. The kit of claim 1, wherein the kit comprises labeled nucleic acid probes specific for the at least two liver fibrosis-related molecules or any of SEQ ID NOS: 1-5544.

5. The kit of claim 1, wherein the kit comprises labeled nucleic acid primers specific for the at least two liver fibrosis-related molecules.

6. The kit of claim 1, wherein the kit comprises:
labeled antibodies for detecting at least three of the liver fibrosis-related molecules,
labeled nucleic acid probes for detecting at least three of the liver fibrosis-related molecules,
labeled nucleic acid primers for detecting at least three of the liver fibrosis-related molecules, or
combinations thereof.

7. The kit of claim 1, wherein the kit comprises:
labeled antibodies for detecting at least four of the liver fibrosis-related molecules,
labeled nucleic acid probes for detecting at least four of the liver fibrosis-related molecules,
labeled nucleic acid primers for detecting at least four of the liver fibrosis-related molecules, or
combinations thereof.

8. The kit of claim 1, wherein the kit comprises:
labeled antibodies for detecting at least five of the liver fibrosis-related molecules,
labeled nucleic acid probes for detecting at least five of the liver fibrosis-related molecules,
labeled nucleic acid primers for detecting at least five of the liver fibrosis-related molecules, or
combinations thereof.

9. The kit of claim 1, wherein the kit comprises labeled antibodies for detecting at least 10 of the liver fibrosis-related molecules, each in a separate container.

10. The kit of claim 1, wherein the kit comprises:
labeled antibodies for detecting at least five of the liver fibrosis-related molecules,
labeled nucleic acid probes for detecting at least five of the liver fibrosis-related molecules,
labeled nucleic acid primers for detecting at least five of the liver fibrosis-related molecules, or
combinations thereof
wherein the at least five liver fibrosis-related molecules comprise at least five of: sulfhydryl oxidase 1 (QSOX1), Ig lambda chain C regions (IGLC1); low affinity immunoglobulin gamma Fc region receptor III-A (FCGR3A); alpha-2-macroglobulin (A2M); afamin (AFM); CD166 antigen (ALCAM); apolipoprotein B-100 (APOB); complement component C7; clusterin (CLU); extracellular matrix protein 1 (ECM1); inter-alpha-trypsin inhibitor heavy chain H3 (ITIH3); galectin-3-binding protein (LGALS3BP); vascular cell adhesion protein 1 (VCAM1); von Willebrand factor (VWF); prothrombin (F2); complement factor I (CFI); plasma kallikrein (KLKB1); coagulation factor XI (F11); beta-Ala-His dipeptidase (CNDP1); cholinesterase (BCHE); serum amyloid P-component (APCS); Beta-2-glycoprotein 1 (APOH); zinc-alpha-2-glycoprotein (AZGP1); complement C4-A (C4A); complement component C6 (C6); complement component C8 alpha chain (C8A); complement component C8 beta chain (C8B); complement component C8 gamma chain (C8G); hemopexin (HPX); insulin-like growth factor-binding protein complex acid labile subunit (IGFALS); inter-alpha-trypsin inhibitor heavy chain H1 (ITIH1); inter-alpha-trypsin inhibitor heavy chain H2 (ITIH2); inter-alpha-trypsin inhibitor heavy chain H4 (ITIH4); proteoglycan 4 (PRG4); retinol-binding protein 4 (RBP4); antithrombin-III (SERPINC1); heparin cofactor 2 (SERPIND1); transthyretin (TTR); apolipoprotein C-III (APOC3); coagulation factor X (F10); kallistatin (SERPINA4); vitronectin (VTN); lumican (LUM); plasma protease C1 inhibitor (SERPING1); biotinidase (BTD); plasminogen (PLG); vitamin K-dependent protein C (PROC); carboxypeptidase N catalytic chain (CPN1); carboxypeptidase B2 (CPB2); vitamin D-binding protein (GC); platelet glycoprotein V (GP5); complement C2 (C2); coagulation factor XII (F12); aminopeptidase N (ANPEP); ceruloplasmin (CP); transforming growth factor-beta-induced protein ig-h3 (TGFB1); IgGFc-binding protein (FCGBP); thyroxine-binding globulin (SERPINA7); poliovirus receptor (PVR); GDH/6PGL endoplasmic bifunctional protein (H6PD); angiotensinogen (AGT); endothelial protein C receptor (PROCR); vasorin (VASN); apolipoprotein C-I (APOC1); intercellular adhesion molecule 1 (ICAM1); macrophage colony-stimulating factor 1 receptor (CSF1R); dopamine beta-hydroxylase (DBH); collagen alpha-3(VI) chain (COL6A3); cartilage oligomeric matrix protein (COMP); scavenger receptor cysteine-rich type 1 protein M130 (CD163); lymphatic vessel endothelial hyaluronic acid receptor 1 (LYVE1); phosphatidylcholine-sterol acyltransferase (LCAT);

carboxypeptidase N subunit 2 (CPN2); vitamin K-dependent protein Z (PROZ); mannan-binding lectin serine protease 1 (MASP1); selenoprotein P (SEPP1); and retinoic acid receptor responder protein 2 (RARRES2).

11. The kit of claim 1, wherein the kit comprises:
labeled antibodies for detecting at least 10 of the liver fibrosis-related molecules,
labeled nucleic acid probes for detecting at least 10 of the liver fibrosis-related molecules,
labeled nucleic acid primers for detecting at least 10 of the liver fibrosis-related molecules, or
combinations thereof
wherein the at least 10 liver fibrosis-related molecules comprise at least 10 of: sulfhydryl oxidase 1 (QSOX1), Ig lambda chain C regions (IGLC1), low affinity immunoglobulin gamma Fc region receptor III-A (FCGR3A); alpha-2-macroglobulin (A2M); afamin (AFM); CD166 antigen (ALCAM); apolipoprotein B-100 (APOB); complement component C7; clusterin (CLU); extracellular matrix protein 1 (ECM1); inter-alpha-trypsin inhibitor heavy chain H3 (ITIH3); galectin-3-binding protein (LGALS3BP); vascular cell adhesion protein 1 (VCAM1); von Willebrand factor (VWF); prothrombin (F2); complement factor I (CFI); plasma kallikrein (KLKB1); coagulation factor XI (F11); beta-Ala-His dipeptidase (CNDP1); cholinesterase (BCHE); serum amyloid P-component (APCS); Beta-2-glycoprotein 1 (APOH); zinc-alpha-2-glycoprotein (AZGP1); complement C4-A (C4A); complement component C6 (C6); complement component C8 alpha chain (C8A); complement component C8 beta chain (C8B); complement component C8 gamma chain (C8G); hemopexin (HPX); insulin-like growth factor-binding protein complex acid labile subunit (IGFALS); inter-alpha-trypsin inhibitor heavy chain H1 (ITIH1); inter-alpha-trypsin inhibitor heavy chain H2 (ITIH2); inter-alpha-trypsin inhibitor heavy chain H4 (ITIH4); proteoglycan 4 (PRG4); retinol-binding protein 4 (RBP4); antithrombin-III (SERPINC1); heparin cofactor 2 (SERPIND1); transthyretin (TTR); apolipoprotein C-III (APOC3); coagulation factor X (F10); kallistatin (SERPINA4); vitronectin (VTN); lumican (LUM); plasma protease C1 inhibitor (SERPING1); biotinidase (BTD); plasminogen (PLG); vitamin K-dependent protein C (PROC); carboxypeptidase N catalytic chain (CPN1); carboxypeptidase B2 (CPB2); vitamin D-binding protein (GC); platelet glycoprotein V (GP5); complement C2 (C2); coagulation factor XII (F12); aminopeptidase N (ANPEP); ceruloplasmin (CP); transforming growth factor-beta-induced protein ig-h3 (TGFB1); IgGFc-binding protein (FCGBP); thyroxine-binding globulin (SERPINA7); poliovirus receptor (PVR); GDH/6PGL endoplasmic bifunctional protein (H6PD); angiotensinogen (AGT); endothelial protein C receptor (PROCR); vasorin (VASN); apolipoprotein C-I (APOC1); intercellular adhesion molecule 1 (ICAM1); macrophage colony-stimulating factor 1 receptor (CSF1R); dopamine beta-hydroxylase (DBH); collagen alpha-3(VI) chain (COL6A3); cartilage oligomeric matrix protein (COMP); scavenger receptor cysteine-rich type 1 protein M130 (CD163); lymphatic vessel endothelial hyaluronic acid receptor 1 (LYVE1); phosphatidylcholine-sterol acyltransferase (LCAT); carboxypeptidase N subunit 2 (CPN2); vitamin K-dependent protein Z (PROZ); mannan-binding lectin serine protease 1 (MASP1); selenoprotein P (SEPP1); and retinoic acid receptor responder protein 2 (RARRES2).

12. The kit of claim 11, wherein the at least 10 liver fibrosis-related molecules comprise: sulfhydryl oxidase 1 (QSOX1), extracellular matrix protein 1 (ECM1), galectin-3-binding protein (LGALS3BP), lumican (LUM), vitronectin (VTN), dopamine beta-hydroxylase (DBH), transthyretin (TTR), cholinesterase (BCHE), retinol-binding protein (RBP4), and insulin-like growth factor binding protein, acid labile subunit (IGFALS).

13. The kit of claim 1, wherein the at least two of the liver fibrosis-related molecules comprise
any of SEQ ID NOS: 1-5544, or
the group consisting of QSOX1, ECM1, LGALS3BP, LUM, VTN, DBH, TTR, BCHE, RBP4, and IGFALS.

14. The kit of claim 1, wherein the kit further comprises a syringe and/or finger-prick device.

15. The kit of claim 1, wherein the kit further comprises a diluent and/or a wash solution.

16. A kit comprising:
at least two stable isotope-labeled liver fibrosis-related proteins, wherein in the at least two liver fibrosis-related proteins comprise at least two of: receptor-type tyrosine-protein phosphatase gamma (PTPRG); sulfhydryl oxidase 1 (QSOX1); glutathione peroxidase 3 (GPX3); Ig kappa chain V-III region VG; Ig kappa chain V-III region HAH; Ig lambda chain V-III region LOI; Ig alpha-1 chain C region (IGHA1); Ig gamma-1 chain C region (IGHG1); Ig gamma-2 chain C region (IGHG2); Ig mu chain C region (IGHM); Ig kappa chain C region (IGKC); Ig kappa chain V-I region HK102 (IGKV1-5); Ig lambda chain C regions (IGLC1); low affinity immunoglobulin gamma Fc region receptor III-A (FCGR3A); alpha-2-macroglobulin (A2M); actin, cytoplasmic 1 (ACTB); afamin (AFM); Alpha-2-HS-glycoprotein (AHSG); CD166 antigen (ALCAM); apolipoprotein B-100 (APOB); apolipoprotein E (APOE); complement component C7; clusterin (CLU); extracellular matrix protein 1 (ECM1); hemoglobin subunit beta; inter-alpha-trypsin inhibitor heavy chain H3 (ITIH3); galectin-3-binding protein (LGALS3BP); mannose-binding protein C (MBL2); L-selectin; alpha-1-antitrypsin (SERPINA1); corticosteroid-binding globulin (SERPINA6); sex hormone-binding globulin (SHBG); vascular cell adhesion protein 1 (VCAM1); von Willebrand factor (VWF); prothrombin (F2); complement factor B (CFB); complement factor I (CFI); complement C1s subcomponent (C1S); complement C1r subcomponent (C1R); plasma kallikrein (KLKB1); coagulation factor XI (F11); coagulation factor IX (F9); Beta-Ala-His dipeptidase (CNDP1); cholinesterase (BCHE); serum albumin (ALB); serum amyloid P-component (APCS); apolipoprotein A-IV (APOA4); apolipoprotein C-III (APOC3); Beta-2-glycoprotein 1 (APOH); zinc-alpha-2-glycoprotein (AZGP1); complement C4-A (C4A); complement component C6 (C6); complement component C8 alpha chain (C8A); complement component C8 beta chain (C8B); complement component C8 gamma chain (C8G); complement component C9 (C9); fibrinogen alpha chain (FGA); hemopexin (HPX); histidine-rich glycoprotein (HRG); insulin-like growth factor-binding protein complex acid labile subunit (IGFALS); inter-alpha-trypsin inhibitor heavy chain H1 (ITIH1); inter-alpha-trypsin inhibitor heavy chain H2 (ITIH2); inter-alpha-trypsin inhibitor heavy chain H4 (ITIH4); alpha-1-acid glycoprotein 1 (ORM1); alpha-1-acid glycoprotein 2 (ORM2); proteoglycan 4 (PRG4); retinol-binding protein 4 (RBP4); alpha-1- antichymotrypsin (SERPINA3); antithrombin-III (SERPINC1); heparin cofactor 2 (SERPIND1); transthyretin (TTR); coagulation factor X (F10); fibronectin (FN1); complement C5 (C5); kallistatin (SERPINA4); vitronectin (VTN); lumican (LUM); hemoglobin subunit alpha (HBA1); plasma protease C1 inhibitor (SERPING1); Ig kappa chain V-I region AU; Ig kappa chain V-II region Cum Ig kappa chain V-IV region; N-acetylmuramoyl-L-alanine amidase (PGLYRP2); biotinidase (BTD); plasminogen (PLG); vitamin K-dependent protein C (PROC); complement C1r subcomponent-like protein (C1RL); carboxypeptidase N catalytic chain (CPN1); carboxypeptidase B2 (CPB2); apolipoprotein A-I (APOA1); complement C4-B (C4B); vitamin D-binding protein (GC); platelet glycoprotein V (GP5); haptoglobin (HP); insulin-like growth factor-binding protein 3 (IGFBP3); kininogen-1 (KNG1); vitamin K-dependent protein S (PROS 1); protein Z-dependent protease inhibitor (SERPINA10); pigment epithelium-derived factor (SERPINF1); alpha-2-antiplasmin (SERPINF2); thrombospondin-1 (THBS1); prostaglandin-H2 D-isomerase (PTGDS); carbonic anhydrase 1 (CA1); fructose-bisphosphate aldolase B (ALDOB); complement C2 (C2); coagulation factor XII (F12); mannan-binding lectin serine protease 2 (MASP2); hyaluronan-binding protein 2 (HABP2); aminopeptidase N (ANPEP); ectonucleotide pyrophosphatase/phosphodiesterase family member 2 (ENPP2); ceruloplasmin (CP); peroxiredoxin-2 (PRDX2); alpha-1B-glycoprotein (A1BG); transforming growth factor-beta-induced protein ig-h3 (TGFB1); monocyte differentiation antigen CD14 (CD14); complement C3 (C3); endoglin (ENG); endothelial protein C receptor (PROCR); IgGFc-binding protein (FCGBP); ficolin-3 (FCN3); fetuin-B (FETUB); hepatocyte growth factor-like protein (MST1); cell surface glycoprotein MUC18 (MCAM); neuropilin-1 (NRP1); secreted phosphoprotein 24 (SPP2); thyroxine-binding globulin (SERPINA7); vasorin (VASN); collagen alpha-1(XVIII) chain (COL18A1); poliovirus receptor (PVR); apolipoprotein A-II (APOA2); Peptidase inhibitor 16 (PI16); GDH/6PGL endoplasmic bifunctional protein (H6PD); angiotensinogen (AGT); complement factor H (CFH); c-reactive protein (CRP); gelsolin (GSN); apolipoprotein C-I (APOC1); macrophage colony-stimulating factor 1 receptor (CSF1R); dopamine beta-hydroxylase (DBH); collagen alpha-3 (VI) chain (COL6A3); cartilage oligomeric matrix protein (COMP); Ig lambda chain V-I region NEWM; intercellular adhesion molecule 1 (ICAM1); scavenger receptor cysteine-rich type 1 protein M130 (CD163); lymphatic vessel endothelial hyaluronic acid receptor 1 (LYVE1); phosphatidylcholine-sterol acyltransferase (LCAT); carboxypeptidase N subunit 2 (CPN2); vitamin K-dependent protein Z (PROZ); mannan-binding lectin serine protease 1 (MASP1); selenoprotein P (SEPP1); and retinoic acid receptor responder protein 2 (RARRES2), or any of SEQ ID NOS: 1-5544.

17. The kit of claim 16, wherein the kit comprises at least ten stable isotope-labeled liver fibrosis-related proteins, wherein the at least ten stable isotope-labeled liver fibrosis-related proteins comprise at least ten of: sulfhydryl oxidase 1 (QSOX1), Ig lambda chain C regions (IGLC1), low affinity immunoglobulin gamma Fc region receptor III-A (FCGR3A); alpha-2-macroglobulin (A2M); afamin (AFM); CD166 antigen (ALCAM); apolipoprotein B-100 (APOB); complement component C7; clusterin (CLU); extracellular matrix protein 1 (ECM1); inter-alpha-trypsin inhibitor heavy chain H3 (ITIH3); galectin-3-binding protein (LGALS3BP); vascular cell adhesion protein 1 (VCAM1); von Willebrand factor (VWF); prothrombin (F2); complement factor I (CFI); plasma kallikrein (KLKB1); coagulation factor XI (F11); beta-Ala-His dipeptidase (CNDP1); cholinesterase (BCHE); serum amyloid P-component (APCS); Beta-2-glycoprotein 1 (APOH); zinc-alpha-2-glycoprotein (AZGP1); complement C4-A (C4A); complement component C6 (C6); complement component C8 alpha chain (C8A); complement component C8 beta chain (C8B); complement component C8 gamma chain (C8G); hemopexin (HPX); insulin-like growth factor-binding protein complex acid labile subunit (IGFALS); inter-alpha-trypsin inhibitor heavy chain H1 (ITIH1); inter-alpha-trypsin inhibitor heavy chain H2 (ITIH2); inter-alpha-trypsin inhibitor heavy chain H4 (ITIH4); proteoglycan 4 (PRG4); retinol-binding protein 4 (RBP4); antithrombin-III (SERPINC1); heparin cofactor 2 (SERPIND1); transthyretin (TTR); apolipoprotein C-III (APOC3); coagulation factor X (F10); kallistatin (SERPINA4); vitronectin (VTN); lumican (LUM); plasma protease C1 inhibitor (SERPING1); biotinidase (BTD); plasminogen (PLG); vitamin K-dependent protein C (PROC); carboxypeptidase N catalytic chain (CPN1); carboxypeptidase B2 (CPB2); vitamin D-binding protein (GC); platelet glycoprotein V (GP5); complement C2 (C2); coagulation factor XII (F12); aminopeptidase N (ANPEP); ceruloplasmin (CP); transforming growth factor-beta-induced protein ig-h3 (TGFB1); IgGFc-binding protein (FCGBP); thyroxine-binding globulin (SERPINA7); poliovirus receptor (PVR); GDH/6PGL endoplasmic bifunctional protein (H6PD); angiotensinogen (AGT); endothelial protein C receptor (PROCR); vasorin (VASN); apolipoprotein C-I (APOC1); intercellular adhesion molecule 1 (ICAM1); macrophage colony-stimulating factor 1 receptor (CSF1R); dopamine beta-hydroxylase (DBH); collagen alpha-3(VI) chain (COL6A3); cartilage oligomeric matrix protein (COMP); scavenger receptor cysteine-rich type 1 protein M130 (CD163); lymphatic vessel endothelial hyaluronic acid receptor 1 (LYVE1); phosphatidylcholine-sterol acyltransferase (LCAT); carboxypeptidase N subunit 2 (CPN2); vitamin K-dependent protein Z (PROZ); mannan-binding lectin serine protease 1 (MASP1); selenoprotein P (SEPP1); and retinoic acid receptor responder protein 2 (RARRES2) listed in Table 12.

18. The kit of claim 17, wherein the at least 10 stable isotope-labeled liver fibrosis-related proteins comprise: sulfhydryl oxidase 1 (QSOX1), extracellular matrix protein 1 (ECM1), galectin-3-binding protein (LGALS3BP), lumican (LUM), vitronectin (VTN), dopamine beta-hydroxylase (DBH), transthyretin (TTR), cholinesterase (BCHE), retinol-binding protein (RBP4), and insulin-like growth factor binding protein, acid labile subunit (IGFALS).

19. The kit of claim 16, wherein the kit further comprises an HPLC column.

20. The kit of claim 16, wherein the kit further comprises a diluent and/or a wash solution.

* * * * *